(12) United States Patent
Snow et al.

(10) Patent No.: US 7,745,490 B2
(45) Date of Patent: Jun. 29, 2010

(54) SUBSTITUTED N-ARYL BENZAMIDES AND RELATED COMPOUNDS FOR TREATMENT OF AMYLOID DISEASES AND SYNUCLEINOPATHIES

(75) Inventors: Alan D. Snow, Lynwood, WA (US); Beth P. Nguyen, Bothell, WA (US); Thomas P. Lake, Snohomish, WA (US); Gerardo M. Castillo, Bothell, WA (US); Manfred Weigele, Cambridge, MA (US)

(73) Assignee: Proteotech, Inc., Kirkland, WA (US)

( * ) Notice: Subject to any disclaimer, the term of this patent is extended or adjusted under 35 U.S.C. 154(b) by 0 days.

(21) Appl. No.: 11/328,748

(22) Filed: Jan. 9, 2006

(65) Prior Publication Data

US 2006/0199838 A1 Sep. 7, 2006

Related U.S. Application Data

(63) Continuation of application No. 11/129,771, filed on May 12, 2005, now abandoned.

(60) Provisional application No. 60/570,669, filed on May 12, 2004, provisional application No. 60/629,525, filed on Nov. 18, 2004.

(51) Int. Cl.
*C07C 303/00* (2006.01)
*A01N 41/06* (2006.01)

(52) U.S. Cl. .................... 514/605; 564/97

(58) Field of Classification Search .......... None
See application file for complete search history.

(56) References Cited

OTHER PUBLICATIONS

Chawla et al., "Challenges in Polymorphism of pharmaceuticals", CRIPS vol. 5, No. 1, Jan.-Mar. 2004, p. 9-12.*
Chandra et al, "Design, synthesis, and structure-activity relationship of novel thiophene derivatives for b-amyloid plaque imaging", Bioorganic&medicinal chemistry letters 16 (2006), 1350-1352.*
http://en.wikipedia.org/wiki/Prodrug (1 Page Double-Sided).*
Han et al., "Targeted prodrug design to optimize drug delivery", The aaps journal, (p. 1-17) of 17.*
http://en.wikipedia.org/wiki/Levodopa (2 Pages Double-Sided).*
Neve et al, "The cell cycle as a therapeutic target for Alzheimer's disease", Pharmacology&Therapeutics, 111 (2006), 99-113.*
Snow et al., CAPLUS AN 2003:972023 (3 Pages).*
Walker et al., Biochem. Pharm., 69 (2005), 1001-1008.*
CNSS Spectrums, www.cnsspectrums.com/aspx/articledetail.aspx?articleid=972.*
Yamashita et al., caplus an 2000:12674.*
Soto, "Protein misfolding and disease; protein refolding and therapy", *FEBS Letters*: 498 204-207 (2001).
Porat et al., "Inhibition of amyloid fibril formation by polyphenols: structural similarities and aromatic interactions as a common inhibition mechanism", Chem Biol Drug Des: 67: 27-37 (2006).
Ono et al., Potent anti-amyloidogenic and fibril destabilizing effects of polyphenols in vitro: implications for the prevention and therapeutics of Alzheimer's disease, *Journal of Neurochemistry*: 87, 172-181 (2003).
Dauer, W., and Przedborski, S. 2003. Parkinson's Disease: Mechanisms and Models. *Neurons*, vol. 39:889-909, (2003).
Polymeropoulos et al., Mapping of a gene for Parkinson's disease to chromosome 4q21-q23, *Science*, 276:1197-1199, (1997).
Papadimitriou et al., Mutated alpha-synuclein gene in two Greek kindreds with familial PD: incomplete penetrance?, *Neurology*, 52:651-654, (1999).
Lee et al., Mechanisms of Parkinson's Disease Linked to Pathological a-Synuclein: New Targets for Drug Discovery, *Neuron* 52, 33-38, (2006).
James, et al., Aβ peptide immunization reduces. behavioural impairment and plaques in a model of Alzheimer's disease, *Nature*, 408:979-982 (2000).
Morgan, et al., Aβ peptide vaccination prevents memory loss in an animal model of Alzheimer's disease, *Nature*, 408:982-985 (2000).

* cited by examiner

*Primary Examiner*—Golam M. M. Shameem
*Assistant Examiner*—Sun Jae Y Loewe
(74) *Attorney, Agent, or Firm*—Rebecca Eagen

(57) ABSTRACT

Substituted n-aryl benzamides, related compounds and their pharmaceutically acceptable derivatives, their synthesis, pharmaceutical compositions containing them, and their use in the treatment of amyloid diseases, including Aβ amyloidosis, such as observed in Alzheimer's disease, IAPP amyloidosis, such as observed in type 2 diabetes, and synucleinopathies, such as observed in Parkinson's disease, and the manufacture of medicaments for such treatment are provided.

8 Claims, No Drawings

SUBSTITUTED N-ARYL BENZAMIDES AND RELATED COMPOUNDS FOR TREATMENT OF AMYLOID DISEASES AND SYNUCLEINOPATHIES

RELATED APPLICATIONS

This application is a continuation of U.S. application Ser. No. 11/129,771, filed May 12, 2005, now abandoned entitled "Substituted N-Aryl Benzamides and Related Compounds for Treatment of Amyloid Diseases and Synucleinopathies." U.S. application Ser. No. 11/129,771 claims priority under 35 U.S.C. §119(e) to U.S. provisional application Ser. Nos. 60/570,669, entitled "Substituted N-Aryl Benzamides and Related Compounds for Treatment of Amyloid Diseases and Synucleinopathies" to Snow et al., filed May 12, 2004 and 60/629,525, entitled "Substituted N-Aryl Benzamides and Related Compounds for Treatment of Amyloid Diseases and Synucleinopathies" to Snow et al., filed Nov. 18, 2004. The contents of the above-referenced applications are incorporated by reference herein.

TECHNICAL FIELD

Provided herein are substituted N-aryl benzamides and related compounds, pharmaceutical compositions and methods for treatment of amyloid diseases, including beta-amyloid protein (Aβ), such as observed in Alzheimer's disease and Down's syndrome, islet amyloid polypeptide (IAPP), such as observed in type 2 diabetes, and alpha-synuclein, such as observed in Parkinson's disease.

BACKGROUND

Alzheimer's disease is characterized by the accumulation of a 39-43 amino acid peptide termed the β-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid, and more specifically, the formation, deposition, accumulation and/or persistence of Aβ fibrils, as a major causative factor of Alzheimer's disease pathogenesis. In addition, besides Alzheimer's disease, a number of other amyloid diseases involve formation, deposition, accumulation and persistence of Aβ fibrils, including Down's syndrome, disorders involving congophilic angiopathy, such as but not limited to, hereditary cerebral hemorrhage of the Dutch type, inclusion body myositosis, dementia pugilistica, cerebral β-amyloid angiopathy, dementia associated with progressive supranuclear palsy, dementia associated with cortical basal degeneration and mild cognitive impairment.

Parkinson's disease is another human disorder characterized by the formation, deposition, accumulation and/or persistence of abnormal fibrillar protein deposits that demonstrate many of the characteristics of amyloid. In Parkinson's disease, an accumulation of cytoplasmic Lewy bodies consisting of filaments of α-synuclein/NAC (non-Aβ component) are believed important in the pathogenesis and as therapeutic targets. New agents or compounds able to inhibit α-synuclein and/or NAC formation, deposition, accumulation and/or persistence, or disrupt pre-formed α-synuclein/NAC fibrils (or portions thereof) are regarded as potential therapeutics for the treatment of Parkinson's and related synucleinopathies. NAC is a 35 amino acid fragment of α-synuclein that has the ability to form amyloid-like fibrils either in vitro or as observed in the brains of patients with Parkinson's disease. The NAC fragment of α-synuclein is a relative important therapeutic target as this portion of α-synuclein is believed crucial for formation of Lewy bodies as observed in all patients with Parkinson's disease, synucleinopathies and related disorders.

A variety of other human diseases also demonstrate amyloid deposition and usually involve systemic organs (i.e. organs or tissues lying outside the central nervous system), with the amyloid accumulation leading to organ dysfunction or failure. These amyloid diseases (discussed below) leading to marked amyloid accumulation in a number of different organs and tissues, are known as systemic amyloidoses. In other amyloid diseases, single organs may be affected such as the pancreas in 90% of patients with type 2 diabetes. In this type of amyloid disease, the beta-cells in the islets of Langerhans in pancreas are believed to be destroyed by the accumulation of fibrillar amyloid deposits consisting primarily of a protein known as islet amyloid polypeptide (IAPP). Inhibiting or reducing such IAPP amyloid fibril formation, deposition, accumulation and persistence is believed to lead to new effective treatments for type 2 diabetes. In Alzheimer's disease, Parkinson's and "systemic" amyloid diseases, there is currently no cure or effective treatment, and the patient usually dies within 3 to 10 years from disease onset.

The amyloid diseases (amyloidoses) are classified according to the type of amyloid protein present as well as the underlying disease. Amyloid diseases have a number of common characteristics including each amyloid consisting of a unique type of amyloid protein. The amyloid diseases include, but are not limited to, the amyloid associated with Alzheimer's disease, Down's syndrome, hereditary cerebral hemorrhage with amyloidosis of the Dutch type, dementia pugilistica, inclusion body myositosis (Askanas et al, *Ann. Neurol.* 43:521-560, 1993) and mild cognitive impairment (where the specific amyloid is referred to as beta-amyloid protein or Aβ), the amyloid associated with chronic inflammation, various forms of malignancy and Familial Mediterranean Fever (where the specific amyloid is referred to as AA amyloid or inflammation-associated amyloidosis), the amyloid associated with multiple myeloma and other B-cell dyscrasias (where the specific amyloid is referred to as AL amyloid), the amyloid associated with type 2 diabetes (where the specific amyloid protein is referred to as amylin or islet amyloid polypeptide or IAPP), the amyloid associated with the prion diseases including Creutzfeldt-Jakob disease, Gerstmann-Straussler syndrome, kuru and animal scrapie (where the specific amyloid is referred to as PrP amyloid), the amyloid associated with long-term hemodialysis and carpal tunnel syndrome (where the specific amyloid is referred to as $\alpha_2$-microglobulin amyloid), the amyloid associated with senile cardiac amyloidosis and Familial Amyloidotic Polyneuropathy (where the specific amyloid is referred to as transthyretin or prealbumin), and the amyloid associated with endocrine tumors such as medullary carcinoma of the thyroid (where the specific amyloid is referred to as variants of procalcitonin). In addition, the α-synuclein protein which forms amyloid-like fibrils, and is Congo red and Thioflavin S positive (specific stains used to detect amyloid fibrillar deposits), is found as part of Lewy bodies in the brains of patients with Parkinson's disease, Lewy body disease (Lewy in *Handbuch der Neurologie*, M. Lewandowski, ed., Springer, Berlin pp. 920-933, 1912; Pollanen et al, *J. Neuropath. Exp. Neurol.* 52:183-191, 1993; Spillantini et al, *Proc. Natl. Acad. Sci. USA* 95:6469-6473, 1998; Arai et al, *Neurosci. Lett.* 259:83-86, 1999), multiple system atrophy (Wakabayashi et al, *Acta*

Neuropath. 96:445-452, 1998), dementia with Lewy bodies, and the Lewy body variant of Alzheimer's disease. For purposes of this disclosure, Parkinson's disease, due to the fact that fibrils develop in the brains of patients with this disease (which are Congo red and Thioflavin S positive, and which contain predominant beta-pleated sheet secondary structure), is now regarded as a disease that also displays the characteristics of an amyloid-like disease.

Systemic amyloidoses which include the amyloid associated with chronic inflammation, various forms of malignancy and familial Mediterranean fever (i.e. AA amyloid or inflammation-associated amyloidosis) (Benson and Cohen, *Arth. Rheum.* 22:36-42, 1979; Kamei et al, *Acta Path. Jpn.* 32:123-133, 1982; McAdam et al., *Lancet* 2:572-573, 1975; Metaxas, *Kidney Int.* 20:676-685, 1981), and the amyloid associated with multiple myeloma and other B-cell dyscrasias (i.e. AL amyloid) (Harada et al., *J. Histochem. Cytochem.* 19:1-15, 1971), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs (Johnson et al, *N. Engl. J. Med.* 321:513-518, 1989). For most of these amyloidoses, there is no apparent cure or effective treatment and the consequences of amyloid deposition can be detrimental to the patient. For example, amyloid deposition in the kidney may lead to renal failure, whereas amyloid deposition in the heart may lead to heart failure. For these patients, amyloid accumulation in systemic organs leads to eventual death generally within 3-5 years. Other amyloidoses may affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (IAPP) deposits found in the islets of Langerhans in the pancreas of 90% of patients with type 2 diabetes (Johnson et al, *N. Engl. J. Med.* 321:513-518, 1989; *Lab. Invest.* 66:522 535, 1992); the $\alpha_2$-microglobulin amyloid deposits in the medial nerve leading to carpal tunnel syndrome as observed in patients undergoing long-term hemodialysis (Geyjo et al, *Biochem. Biophys. Res. Comm.* 129: 701-706, 1985; *Kidney Int.* 30:385-390, 1986); the prealbumin/transthyretin amyloid observed in the hearts of patients with senile cardiac amyloid; and the prealbumin/transthyretin amyloid observed in peripheral nerves of patients who have familial amyloidotic polyneuropathy (Skinner and Cohen, *Biochem. Biophys. Res. Comm.* 99:1326-1332, 1981; Saraiva et al, *J. Lab. Clin. Med.* 102: 590-603, 1983; *J. Clin. Invest.* 74:104-119, 1984; Tawara et al, *J. Lab. Clin. Med.* 98:811-822, 1989).

Alzheimer's disease also puts a heavy economic burden on society. A recent study estimated that the cost of caring for one Alzheimer's disease patient with severe cognitive impairments at home or in a nursing home, is more than $47,000 per year (*A Guide to Understanding Alzheimer's Disease and Related Disorders*). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (2003 *Progress Report on Alzheimer's Disease*).

Amyloid as a Therapeutic Target for Alzheimer's Disease

Alzheimer's disease is characterized by the deposition and accumulation of a 39-43 amino acid peptide termed the beta-amyloid protein, Aβ or β/A4 (Glenner and Wong, *Biochem. Biophys. Res. Comm.* 120:885-890, 1984; Masters et al., *Proc. Natl. Acad. Sci. USA* 82:4245-4249, 1985; Husby et al., *Bull. WHO* 71:105-108, 1993). Aβ is derived by protease cleavage from larger precursor proteins termed β-amyloid precursor proteins (APPs) of which there are several alternatively spliced variants. The most abundant forms of the APPs include proteins consisting of 695, 751 and 770 amino acids (Tanzi et al., *Nature* 31:528-530, 1988).

The small Aβ peptide is a major component that makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al., *Proc. Natl. Acad. Sci. USA* 83:4913-4917, 1986; Kosik et al., *Proc. Natl. Acad. Sci. USA* 83:4044-4048, 1986; Lee et al., *Science* 251:675-678, 1991). The pathological hallmark of Alzheimer's disease is therefore the presence of "plaques" and "tangles", with amyloid being deposited in the central core of the plaques. The other major type of lesion found in the Alzheimer's disease brain is the accumulation of amyloid in the walls of blood vessels, both within the brain parenchyma and in the walls of meningeal vessels that lie outside the brain. The amyloid deposits localized to the walls of blood vessels are referred to as cerebrovascular amyloid or congophilic angiopathy (Mandybur, *J. Neuropath. Exp. Neurol.* 45:79-90, 1986; Pardridge et al., *J. Neurochem.* 49:1394-1401, 1987)

For many years there has been an ongoing scientific debate as to the importance of "amyloid" in Alzheimer's disease, and whether the "plaques" and "tangles" characteristic of this disease were a cause or merely a consequence of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time (Pike et al., *Br. Res.* 563:311-314, 1991; *J. Neurochem.* 64:253-265, 1995). Studies suggest that it is the fibrillar structure (consisting of a predominant β-pleated sheet secondary structure), characteristic of all amyloids, that is responsible for the neurotoxic effects. Aβ has also been found to be neurotoxic in slice cultures of hippocampus (Harrigan et al., *Neurobiol. Aging* 16:779-789, 1995) and induces nerve cell death in transgenic mice (Games et al., *Nature* 373:523-527, 1995; Hsiao et al., *Science* 274:99-102, 1996). Injection of the Alzheimer's Aβ into rat brain also causes memory impairment and neuronal dysfunction (Flood et al., *Proc. Natl. Acad. Sci. USA* 88:3363-3366, 1991; *Br. Res.* 663:271-276, 1994).

Probably, the most convincing evidence that Aβ amyloid is directly involved in the pathogenesis of Alzheimer's disease comes from genetic studies. It was discovered that the production of Aβ can result from mutations in the gene encoding, its precursor, β-amyloid precursor protein (Van Broeckhoven et al., *Science* 248:1120-1122, 1990; Murrell et al., *Science* 254:97-99, 1991; Haass et al., *Nature Med.* 1:1291-1296, 1995). The identification of mutations in the beta-amyloid precursor protein gene that cause early onset familial Alzheimer's disease is the strongest argument that amyloid is central to the pathogenetic process underlying this disease. Four reported disease-causing mutations have been discovered which demonstrate the importance of Aβ in causing familial Alzheimer's disease (reviewed in Hardy, *Nature Genet.* 1:233-234, 1992). All of these studies suggest that providing a drug to reduce, eliminate or prevent fibrillar Aβ formation, deposition, accumulation and/or persistence in the brains of human patients will serve as an effective therapeutic.

Parkinson's Disease and Synucleinopathies

Parkinson's disease is a neurodegenerative disorder that is pathologically characterized by the presence of intracytoplasmic Lewy bodies (Lewy in *Handbuch der Neurologie*, M. Lewandowski, ed., Springer, Berlin, pp. 920-933, 1912; Pollanen et al., *J. Neuropath. Exp. Neurol.* 52:183-191, 1993), the major components of which are filaments consisting of α-synuclein (Spillantini et al., *Proc. Natl. Acad. Sci. USA* 95:6469-6473, 1998; Arai et al., *Neurosci. Lett.* 259:83-86, 1999), an 140-amino acid protein (Ueda et al., *Proc. Natl. Acad. Sci. USA* 90:11282-11286, 1993). Two dominant mutations in α-synuclein causing familial early onset Parkinson's disease have been described suggesting that Lewy bodies contribute mechanistically to the degeneration of neurons in Parkinson's disease and related disorders (Polymeropoulos et al., *Science* 276:2045-2047, 1997; Kruger et al., *Nature Genet.* 18:106-108, 1998). Recently, in vitro studies have demonstrated that recombinant α-synuclein can indeed form Lewy body-like fibrils (Conway et al., *Nature Med.* 4:1318-1320, 1998; Hashimoto et al., *Brain Res.* 799:301-306, 1998; Nahri et al., *J. Biol. Chem.* 274:9843-9846, 1999). Most importantly, both Parkinson's disease-linked α-synuclein mutations accelerate this aggregation process, demonstrating that such in vitro studies may have relevance for Parkinson's disease pathogenesis. Alpha-synuclein aggregation and fibril formation fulfills of the criteria of a nucleation-dependent polymerization process (Wood et al., *J. Biol. Chem.* 274: 19509-19512, 1999). In this regard α-synuclein fibril formation resembles that of Alzheimer's β-amyloid protein (Aβ) fibrils. Alpha-synuclein recombinant protein, and non-Aβ component (known as NAC), which is a 35-amino acid peptide fragment of α-synuclein, both have the ability to form fibrils when incubated at 37° C., and are positive with amyloid stains such as Congo red (demonstrating a red/green birefringence when viewed under polarized light) and Thioflavin S (demonstrating positive fluorescence) (Hashimoto et al., *Brain Res.* 799:301-306, 1998; Ueda et al., *Proc. Natl. Acad. Sci. USA* 90:11282-11286, 1993).

Synucleins are a family of small, presynaptic neuronal proteins composed of α-, β-, and γ-synucleins, of which only α-synuclein aggregates have been associated with several neurological diseases (Ian et al., *Clinical Neurosc. Res.* 1:445-455, 2001; Trojanowski and Lee, *Neurotoxicology* 23:457-460, 2002). The role of synucleins (and in particular, alpha-synuclein) in the etiology of a number of neurodegenerative and/or amyloid diseases has developed from several observations. Pathologically, synuclein was identified as a major component of Lewy bodies, the hallmark inclusions of Parkinson's disease, and a fragment thereof was isolated from amyloid plaques of a different neurological disease, Alzheimer's disease. Biochemically, recombinant α-synuclein was shown to form amyloid-like fibrils that recapitulated the ultra-structural features of alpha-synuclein isolated from patients with dementia with Lewy bodies, Parkinson's disease and multiple system atrophy. Additionally, the identification of mutations within the synuclein gene, albeit in rare cases of familial Parkinson's disease, demonstrated an unequivocal link between synuclein pathology and neurodegenerative diseases. The common involvement of α-synuclein in a spectrum of diseases such as Parkinson's disease, dementia with Lewy bodies, multiple system atrophy and the Lewy body variant of Alzheimer's disease has led to the classification of these diseases under the umbrella term of "synucleinopathies".

Parkinson's disease α-synuclein fibrils, like the Aβ fibrils of Alzheimer's disease, also consist of a predominantly β-pleated sheet structure. Therefore, compounds found to inhibit Alzheimer's disease Aβ amyloid fibril formation are also anticipated to be effective in the inhibition of α-synuclein/NAC fibril formation, as shown from Examples provided herein. These compounds would therefore also serve as therapeutics for Parkinson's disease and other synucleinopathies, in addition to having efficacy as a therapeutic for Alzheimer's disease, type 2 diabetes, and other amyloid disorders.

Discovery and identification of new compounds or agents as potential therapeutics to arrest amyloid formation, deposition, accumulation and/or persistence that occurs in Alzheimer's disease, Parkinson's disease, type II diabetes, and other amyloidoses are desperately sought.

SUMMARY

Provided herein are compounds and pharmaceutical compositions containing compounds having formula:

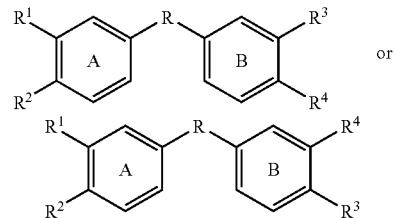

or a pharmaceutically acceptable derivative thereof, where R is selected from a 1) CONR' and 2) $C_1$-$C_{10}$ alkylene group, in which: (a) when the number of carbon atoms is at least 2, there are optionally 1 or 2 double bonds; (b) 1 to 3 non-adjacent methylene groups are optionally replaced by NR', O, or S; (c) 1 or 2 methylene groups are optionally replaced by a carbonyl or hydroxymethylene group; and (d) 1 or 2 methylene groups are optionally replaced by a cycloalkyl or heterocyclyl group that is optionally substituted with one or more substituents selected from lower alkyl, NR', O, or S;

R' is H, alkyl, or acyl;

$R^1$, $R^2$, $R^3$ and $R^4$ are each independently selected as follows:

i) $R^1$, $R^2$, $R^3$ and $R^4$ are each independently selected from OH, —$NR^5C(=O)R^6$, and —$NR^7S(O_2)R^8$, wherein $R^5$ and $R^7$ are each independently hydrogen, substituted or unsubstituted alkyl, substituted or unsubstituted aryl, substituted or unsubstituted aralkyl, substituted or unsubstituted heteroaryl, substituted or unsubstituted heteroaralkyl, substituted or unsubstituted heterocyclyl or substituted or unsubstituted heterocyclylalkyl; and $R^6$ and $R^8$ are each independently substituted or unsubstituted alkoxy, substituted or unsubstituted aralkoxy, substituted or unsubstituted alkyl, substituted or unsubstituted heteroaryl, substituted or unsubstituted heterocyclyl, substituted or unsubstituted aryl or —$NR^9R^{10}$ where $R^9$ and $R^{10}$ are each independently hydrogen, alkyl, aralkyl, aryl, heteroaryl, heteroaralkyl or heterocyclyl, with the proviso that at least one of $R^1$, $R^2$, $R^3$ and $R^4$ is not OH;

ii) $R^1$ and $R^2$ and/or $R^3$ and $R^4$ together are —NH—C(=O)—NH—, —NH—S(O_2)—NH—, —CH_2—C(=O)—NH— or —CH_2—S(O_2)—NH and together with the carbon atoms on which they are substituted form a 5 membered heterocyclic ring and the others of $R^1$, $R^2$, $R^3$ and $R^4$ are each independently selected as in i); or iii) at least one of $R^1$, $R^2$, $R^3$ and $R^4$ is —NH—$CR^a$=$CR^b$—, or —NH—$S(O_2)CR^cR^d$ and together with two adjacent carbon atoms of the phenyl ring forms a substituted or unsubstituted heterocyclic or substituted or unsubstituted heteroaromatic ring, and the others of $R^1$, $R^2$, $R^3$ and $R^4$ are each independently selected as in i) or ii); and wherein the rings A and B are substituted with one or more substitutents selected from electron withdrawing groups including, but not limited to halo, pseudohalo, nitro, $^+NH_3$, $SO_3H$, carboxy and haloalkyl.

In one embodiment, $R^1$ to $R^{10}$, $R^a$, $R^b$, $R^c$ and $R^d$ are appropriately selected to optimize physicochemical and/or biological properties such as, bioavailability, pharmacokinetics, blood-brain barrier penetration, optimized metabolism, and enhanced efficacy for treatment of amyloid diseases and synucleinopathies.

Also provided are any pharmaceutically-acceptable derivatives, including salts, esters, enol ethers or esters, acetals, ketals, orthoesters, hemiacetals, hemiketals, solvates, hydrates or prodrugs of the compounds. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine, tris(hydroxymethyl)aminomethane, alkali metal salts, such as but not limited to lithium, potassium and sodium, alkali earth metal salts, such as but not limited to barium, calcium and magnesium, transition metal salts, such as but not limited to zinc and other metal salts, such as but not limited to sodium hydrogen phosphate and disodium phosphate, and also including, but not limited to, salts of mineral acids, such as but not limited to hydrochlorides and sulfates, salts of organic acids, such as but not limited to acetates, lactates, malates, tartrates, citrates, ascorbates, succinates, butyrates, valerates and fumarates.

Pharmaceutical formulations for administration by an appropriate route and means containing effective concentrations of one or more of the compounds provided herein or pharmaceutically acceptable derivatives, such as salts, esters, enol ethers or esters, acetals, ketals, orthoesters, hemiacetals, hemiketals, solvates, hydrates or prodrugs, of the compounds that deliver amounts effective for the treatment of amyloid diseases, are also provided.

The formulations are compositions suitable for administration by any desired route and include solutions, suspensions, emulsions, tablets, dispersible tablets, pills, capsules, powders, dry powders for inhalation, sustained release formulations, aerosols for nasal and respiratory delivery, patches for transdermal delivery and any other suitable route. The compositions should be suitable for oral administration, parenteral administration by injection, including subcutaneously, intramuscularly or intravenously as an injectable aqueous or oily solution or emulsion, transdermal administration and other selected routes.

Methods using such compounds and compositions for disrupting, disaggregating and causing removal, reduction or clearance of amyloid or synuclein fibrils are provided thereby providing new treatments for amyloid diseases and synucleinopathies.

Also provided are methods for treatment, prevention or amelioration of one or more symptoms of amyloid diseases or amyloidoses, including but not limited to diseases associated with the formation, deposition, accumulation, or persistence of amyloid fibrils, for example, the fibrils of an amyloid protein selected from Aβ amyloid, AA amyloid, AL amyloid, IAPP amyloid, PrP amyloid, $\alpha_2$-microglobulin amyloid, transthyretin, prealbumin, and procalcitonin.

Methods for treatment of amyloid diseases, include, but are not limited to Alzheimer's disease, Down's syndrome, dementia pugilistica, multiple system atrophy, inclusion body myositosis, hereditary cerebral hemorrhage with amyloidosis of the Dutch type, Nieman-Pick disease type C, cerebral β-amyloid angiopathy, dementia associated with cortical basal degeneration, the amyloidosis of type 2 diabetes, the amyloidosis of chronic inflammation, the amyloidosis of malignancy and Familial Mediterranean Fever, the amyloidosis of multiple myeloma and B-cell dyscrasias, the amyloidosis of the prion diseases, Creutzfeldt-Jakob disease, Gerstmann-Straussler syndrome, kuru, scrapie, the amyloidosis associated with carpal tunnel syndrome, senile cardiac amyloidosis, familial amyloidotic polyneuropathy, and the amyloidosis associated with endocrine tumors.

Also provided are methods for treatment, prevention or amelioration of one or more symptoms of synuclein diseases or synucleinopathies. In one embodiment, the methods inhibit or prevent α-synuclein/NAC fibril formation, inhibit or prevent α-synuclein/NAC fibril growth, and/or cause disassembly, disruption, and/or disaggregation of preformed α-synuclein/NAC fibrils and α-synuclein/NAC-associated protein deposits. Synuclein diseases include, but are not limited to Parkinson's disease, familial Parkinson's disease, Lewy body disease, the Lewy body variant of Alzheimer's disease, dementia with Lewy bodies, multiple system atrophy, and the Parkinsonism-dementia complex of Guam.

DETAILED DESCRIPTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein "Amyloid diseases" or "amyloidoses" are diseases associated with the formation, deposition, accumulation, or persistence of amyloid fibrils, including but not limited to the fibrils of an amyloid protein selected from Aβ amyloid, AA amyloid, AL amyloid, IAPP amyloid, PrP amyloid, $\alpha_2$-microglobulin amyloid, transthyretin, prealbumin, and procalcitonin. Such diseases include, but are not limited to Alzheimer's disease, Down's syndrome, dementia pugilistica, multiple system atrophy, inclusion body myositosis, hereditary cerebral hemorrhage with amyloidosis of the Dutch type, Nieman-Pick disease type C, cerebral β-amyloid angiopathy, dementia associated with cortical basal degeneration, the amyloidosis of type 2 diabetes, the amyloidosis of chronic inflammation, the amyloidosis of malignancy and Familial Mediterranean Fever, the amyloidosis of multiple myeloma and B-cell dyscrasias, the amyloidosis of the prion diseases, Creutzfeldt-Jakob disease, Gerstmann-Straussler syndrome, kuru, scrapie, the amyloidosis associated with carpal tunnel syndrome, senile cardiac amyloidosis, familial amyloidotic polyneuropathy, and the amyloidosis associated with endocrine tumors.

As used herein, "Synuclein diseases" or "synucleinopathies" are diseases associated with the formation, deposition, accumulation, or persistence of synuclein fibrils, including, but not limited to α-synuclein fibrils. Such diseases include, but are not limited to Parkinson's disease, familial Parkinson's disease, Lewy body disease, the Lewy body variant of Alzheimer's disease, dementia with Lewy bodies, multiple system atrophy, and the Parkinsonism-dementia complex of Guam.

"Fibrillogenesis" refers to the formation, deposition, accumulation and/or persistence of amyloid fibrils, filaments, inclusions, deposits, as well as synuclein (usually involving α-synuclein) and/or NAC fibrils, filaments, inclusions, deposits or the like.

"Inhibition of fibrillogenesis" refers to the inhibition of formation, deposition, accumulation and/or persistence of such amyloid fibrils or synuclein fibril-like deposits.

"Disruption of fibrils or fibrillogenesis" refers to the disruption of pre-formed amyloid or synuclein fibrils, that usually exist in a pre-dominant β-pleated sheet secondary structure. Such disruption by compounds provided herein may involve marked reduction or disassembly of amyloid or synuclein fibrils as assessed by various methods such as Thioflavin T fluorometry, Congo red binding, SDS-PAGE/Western blotting, as demonstrated by the Examples presented in this application.

"Mammal" includes both humans and non-human mammals, such as companion animals (cats, dogs, and the like), laboratory animals (such as mice, rats, guinea pigs, and the like) and farm animals (cattle, horses, sheep, goats, swine, and the like).

"Pharmaceutically acceptable excipient" means an excipient that is conventionally useful in preparing a pharmaceutical composition that is generally safe, non-toxic, and desirable, and includes excipients that are acceptable for veterinary use or for human pharmaceutical use. Such excipients may be solid, liquid, semisolid, or, in the case of an aerosol composition, gaseous.

A "therapeutically effective amount" means the amount that, when administered to a subject or animal for treating a disease, is sufficient to affect the desired degree of treatment, prevention or symptom amelioration for the disease. A "therapeutically effective amount" or a "therapeutically effective dosage" in certain embodiments inhibits, reduces, disrupts, disassembles amyloid or synuclein fibril formation, deposition, accumulation and/or persistence, or treats, prevents, or ameliorates one or more symptoms of a disease associated with these conditions, such as an amyloid disease or a synucleinopathy, in a measurable amount in one embodiment, by at least 20%, in other embodiments, by at least 40%, in other embodiment by at least 60%, and in still other embodiment by at least 80%, relative to an untreated subject. Effective amounts of a compound provided herein or composition thereof for treatment of a mammalian subject are about 0.1 to about 1000 mg/Kg of body weight of the subject/day, such as from about 1 to about 100 mg/Kg/day, in other embodiment, from about 10 to about 100 mg/Kg/day. A broad range of disclosed composition dosages are believed to be both safe and effective.

The term "sustained release component" is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiologically solvents may be formulated for administration by inhalation or insufflation (either through the mouth or the nose) or oral, buccal, parenteral, or rectal administration, as examples.

As used herein, pharmaceutically acceptable derivatives of a compound include salts, esters, enol ethers, enol esters, acetals, ketals, orthoesters, hemiacetals, hemiketals, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris (hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment of a disease also includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease), such as by disruption of pre-formed amyloid or synuclein fibrils. One such preventive treatment may be use of the disclosed compounds for the treatment of Mild Cognitive impairment (MCI).

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, "NAC" (non-Aβ component) is a 35-amino acid peptide fragment of α-synuclein, which like α-synuclein, has the ability to form amyloid-like fibrils when incubated at 37° C., and is positive with amyloid stains such as Congo red (demonstrating a red/green birefringence when viewed under polarized light) and Thioflavin S (demonstrating positive fluorescence) (Hashimoto et al., Brain Res. 799: 301-306, 1998; Ueda et al., Proc. Natl. Acad. Sci. U.S.A. 90:11282-11286, 1993). Inhibition of NAC fibril formation, deposition, accumulation, aggregation, and/or persistence is believed to be effective treatment for a number of diseases involving α-synuclein, such as Parkinson's disease, Lewy body disease and multiple system atrophy.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_2$O—.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is alkyl, including lower alkyl. As used herein, "dialkylaminocarbonyl" refers to —C(O)NR'R in which R' and R are each independently alkyl, including lower alkyl; "carboxamide" refers to groups of formula —NR'COR in which R' and R are each independently alkyl, including lower alkyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(=O) and S(=O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR—(CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene" refers to —(CRR)$_n$—S—(CRR)$_m$—, —(CRR)$_n$—S(=O)—(CRR)$_m$—, and —(CRR)$_n$—S(=O)$_2$—(CRR)$_m$—, where n and m are each independently an integer from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH—CH=CH— and —CH=CH—CH$_2$—. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, —C=C—(CH$_2$)$_n$—C≡C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from $Q^1$.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylidene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the divalent group —SO$_2$NHNH—. "Hydrazide" refers to the divalent group —C(O)NHNH—. "Azo" refers to the divalent group —N=N—. "Hydrazinyl" refers to the divalent group —NH—NH—.

Where the number of any given substituent is not specified (e.g., haloalkyl), there may be one or more substituents present. For example, "haloalkyl" may include one or more of the same or different halogens. As another example, "$C_{1-3}$alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

Provided herein are compounds and pharmaceutical compositions containing compounds having formula:

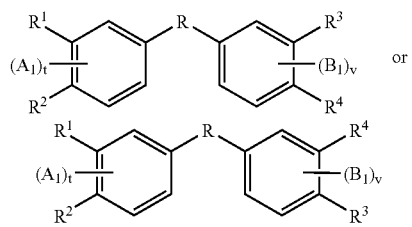

or a pharmaceutically acceptable derivative thereof, where R is selected as follows: 1) R is CONR' or 2) R is $C_1$-$C_{10}$ alkylene group, in which: (a) when the number of carbon atoms is at least 2, there are optionally 1 or 2 double bonds; (b) 1 to 3 non-adjacent methylene groups are optionally replaced by NR', O, or S; (c) 1 or 2 methylene groups are optionally replaced by a carbonyl or hydroxymethylene group; and (d) 1 or 2 methylene groups are optionally replaced by a cycloalkyl or heterocyclyl group that is optionally substituted with one or more substituents selected from lower alkyl, NR', O, or S;

R' is H, alkyl, or acyl;

$A_1$ and $B_1$ are each independently selected from halogen, pseudohalo, nitro, $^+NH_3$, $SO_3H$, carboxy and haloalkyl;

t and v are each independently 0 to 3;

$R^1$, $R^2$, $R^3$ and $R^4$ are each independently selected as follows:

i) $R^1$, $R^2$, $R^3$ and $R^4$ are each independently selected from OH, —NR$^5$C(=O)R$^6$ and —NR$^7$S(O$_2$)R$^8$, wherein R$^5$ and R$^7$ are each independently hydrogen, substituted or unsubstituted alkyl, substituted or unsubstituted aryl, substituted or unsubstituted aralkyl, substituted or unsubstituted heteroaryl, substituted or unsubstituted heteroaralkyl, substituted or unsubstituted heterocyclyl or substituted or unsubstituted heterocyclylalkyl; and R$^6$ and R$^8$ are each independently substituted or unsubstituted alkoxy, substituted or unsubstituted aralkoxy, substituted or unsubstituted alkyl, substituted or unsubstituted heteroaryl, substituted or unsubstituted heterocyclyl, substituted or unsubstituted aryl or —NR$^9$R$^{10}$ where R$^9$ and R$^{10}$ are each independently hydrogen, alkyl, aralkyl, aryl, heteroaryl, heteroaralkyl or heterocyclyl, with the proviso that at least one of R$^1$, R$^2$, R$^3$ and R$^4$ is not OH;

ii) $R^1$ and $R^2$ and/or $R^3$ and $R^4$ together are —NH—C(=O)—NH—, —NH—S(O$_2$)—NH—, —CH$_2$—C(=O)—NH— or —CH$_2$—S(O$_2$)—NH and together with the carbon atoms on which they are substituted form a 5 membered heterocyclic ring and the others of R$^1$, R$^2$, R$^3$ and R$^4$ are each independently selected as in i); or iii) at least one of $R^1$, $R^2$, $R^3$ and $R^4$ is —NH—$CR^a$=$CR^b$—, or —NH—$S(O_2)CR^cR^d$— and together with two adjacent carbon atoms of the phenyl ring forms a substituted or unsubstituted heterocyclic or substituted or unsubstituted heteroaromatic ring, and the others of $R^1$, $R^2$, $R^3$ and $R^4$ are each independently selected as in i) or ii); where $R^a$, $R^b$, $R^c$ and $R^d$ are each independently hydrogen or substituted or unsubstituted alkyl, wherein the substituents when present are selected from one or more substituents, in one embodiment one to three or four substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., —O—$(CH_2)_y$—O—), thioalkylenoxy (i.e., —S—$(CH_2)_y$—O—) or alkylenedithioxy (i.e., —S—$(CH_2)_y$—S—) where y is 1 or 2; or two $Q^1$ groups, which substitute the same atom, together form alkylene; wherein $R^{50}$ is hydroxy, alkoxy, aralkoxy, alkyl, heteroaryl, heterocyclyl, aryl or —$NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or —$NR^{70}R^{71}$.

In certain embodiments, the compounds provided herein have formula:

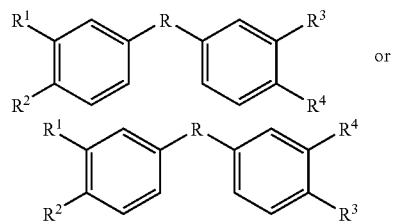

or a pharmaceutically acceptable derivative thereof, where R is selected from $C_1$-$C_{10}$ alkylene group, in which, (a) when the number of carbon atoms is at least 2, there are optionally 1 or 2 double bonds; (b) 1 to 3 non-adjacent methylene groups are optionally replaced by NR' (where R' is H, alkyl, or acyl), O, or S; (c) 1 or 2 methylene groups are optionally replaced by a carbonyl or hydroxymethylene group; and (d) 1 or 2 methylene groups are optionally replaced by a cycloalkyl or heterocyclyl group that is optionally substituted with one or more substituents selected from lower alkyl, NR' (where R' is H, alkyl, or acyl), O, or S, $R^1$, $R^2$, $R^3$ and $R^4$ are each independently selected as follows:
i) $R^1$, $R^2$, $R^3$ and $R^4$ are each independently selected from OH, —$NR^5C(=O)R^6$ and —$NR^7S(O_2)R^8$, wherein $R^5$ and $R^7$ are each independently hydrogen, substituted or unsubstituted alkyl, substituted or unsubstituted aryl, substituted or unsubstituted aralkyl, substituted or unsubstituted heteroaryl, substituted or unsubstituted heteroaralkyl, substituted or unsubstituted heterocyclyl or substituted or unsubstituted heterocyclylalkyl; and $R^6$ and $R^8$ are each independently substituted or unsubstituted alkoxy, substituted or unsubstituted aralkoxy, substituted or unsubstituted alkyl, substituted or unsubstituted heteroaryl, substituted or unsubstituted heterocyclyl, substituted or unsubstituted aryl or —$NR^9R^{10}$ where $R^9$ and $R^{10}$ are each independently hydrogen, alkyl, aralkyl, aryl, heteroaryl, heteroaralkyl or heterocyclyl, with the proviso that at least one of $R^1$, $R^2$, $R^3$ and $R^4$ is not OH;
ii) $R^1$ and $R^2$ and/or $R^3$ and $R^4$ together are —NH—C(=O)—NH—, —NH—$S(O_2)$—NH—, —$CH_2$—C(=O)—NH— or —$CH_2$—$S(O_2)$—NH and together with the carbon atoms on which they are substituted form a 5 membered heterocyclic ring and the others of $R^1$, $R^2$, $R^3$ and $R^4$ are each independently selected as in i); or iii) at least one of $R^1$, $R^2$, $R^3$ and $R^4$ is —NH—$CR^a$=$CR^b$—, or —NH—S(O$_2$)$CR^cR^d$— and together with two adjacent carbon atoms of the phenyl ring forms a substituted or unsubstituted heterocyclic or substituted or unsubstituted heteroaromatic ring, and the others of $R^1$, $R^2$, $R^3$ and $R^4$ are each independently selected as in i) or ii); where $R^a$, $R^b$, $R^c$ and $R^d$ are each independently hydrogen or substituted or unsubstituted alkyl, wherein the substituents when present are selected from one or more substituents, in one embodiment one to three or four substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{51}$R$^{52}$R$^{53}$, P(R$^{50}$)$_2$, P(=O)(R$^{50}$)$_2$, OP(=O)(R$^{50}$)$_2$, —NR$^{60}$C(=O)R$^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., —O—(CH$_2$)$_y$—O—), thioalkylenoxy (i.e., —S—(CH$_2$)$_y$—O—) or alkylenedithioxy (i.e., —S—(CH$_2$)$_y$—S—) where y is 1 or 2; or two $Q^1$ groups, which substitute the same atom, together form alkylene; wherein $R^{50}$ is hydroxy, alkoxy, aralkoxy, alkyl, heteroaryl, heterocyclyl, aryl or —NR$^{70}$R$^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or —NR$^{70}$R$^{71}$.

In certain embodiments, $Q^1$ is oxo, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl or heteroarylalkyl.

In certain embodiments, $Q^1$ is oxo or alkyl. In certain embodiments, $Q^1$ is oxo. In certain embodiments, $Q^1$ is alkyl. In certain embodiments, $Q^1$ is lower alkyl. In certain embodiments, $Q^1$ is methyl.

In certain embodiments, R' is H or alkyl. In other embodiments, R' is H.

In certain embodiments, t is 0, 1 or 2. In certain embodiments, t is 0 or 1. In certain embodiments, t is 1. In certain embodiments, v is 0, 1 or 2. In certain embodiments, v is 0 or 1. In certain embodiments, v is 1.

In one embodiment, R is —(CH$_2$)$_m$C(O)(CH$_2$)$_s$NH(CH$_2$)$_r$—, —(CH$_2$)$_p$— or —(CH$_2$)$_s$Y(CH$_2$)$_r$—, in which Y is a cycloalkyl or heterocyclyl group that is optionally substituted with one or more substituents selected from alkyl, NR', O, or S; p is 1 to 10; and m, s and r are each independently 0 to 6.

In one embodiment, R is —C(O)NH, CH$_2$CH$_2$—, or —(CH$_2$)Y(CH$_2$)—. In one embodiment, R is —C(O)NH—. In one embodiment, R is —CH$_2$CH$_2$—. In one embodiment, R is —(CH$_2$)Y(CH$_2$)—.

In one embodiment, Y is heterocyclyl, optionally substituted with one or more substituents selected from alkyl and oxo. In one embodiment, Y is bridged heterocyclyl, optionally substituted with one or more substituents selected from alkyl and oxo. In one embodiment, Y is bicycloheterocyclyl substituted with methyl and oxo. In one embodiment, Y is bicycloheterocyclyl where the heteroatom is N. In another embodiment, Y is

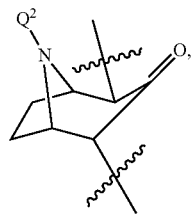

where $Q^2$ is alkyl.

In certain embodiments, Y is

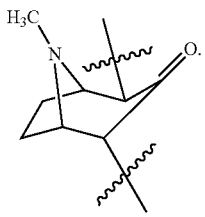

In certain embodiments, R is substituted with alkyl, alkenyl, alkynyl, cycloalkyl, cycloalkylalkyl, heterocyclyl, heterocyclylalkyl, aryl, heteroaryl, aralkyl or heteroaralkyl.

In certain embodiments, R is substituted with alkyl. In other embodiments, R substituted with lower alkyl. In certain embodiments, R is substituted with methyl.

In another embodiment, the compounds for use in the compositions and methods provided herein have formula:

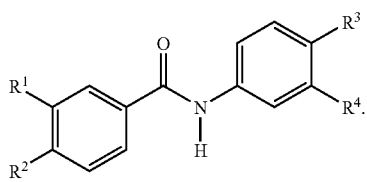

In another embodiment, the compounds for use in the compositions and methods provided herein have formula

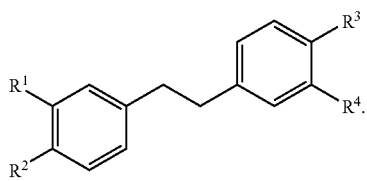

In certain embodiments, $R^1$, $R^2$, $R^3$ and $R^4$ are each independently selected from
  i) OH, formylamide, alkylamide, alkylarylamide, aralkylamide, arylamide, N-alkyl-N-alkylsulfonamide, alkylsulfonamide, alkylarylsulfonamide, arylsulfonamide or aralkylsulfonamide, with the proviso that at least one of $R^1$, $R^2$, $R^3$ and $R^4$ is not OH;
  ii) $R^1$ and $R^2$ and/or $R^3$ and $R^4$ together are —NH—C(=O)—NH—, —NH—S($O_2$)—NH—, —$CH_2$—C(=O)—NH— or —$CH_2$—S($O_2$)—NH and together with the carbon atoms on which they are substituted form a 5 membered heterocyclic ring and the others of $R^1$, $R^2$, $R^3$ and $R^4$ are each independently selected as in i); or
  iii) at least one of $R^1$, $R^2$, $R^3$ and $R^4$ is —NH—$CR^a$=$CR^b$—, or —NH—S($O_2$)$CR^cR^d$— and together with two adjacent carbon atoms of the phenyl ring forms a substituted or unsubstituted heterocyclic or substituted or unsubstituted heteroaromatic ring, and the others of $R^1$, $R^2$, $R^3$ and $R^4$ are each independently selected as in i) or ii); where $R^a$, $R^b$, $R^c$ and $R^d$ are each independently hydrogen or alkyl.

In one embodiment, $R^1$, $R^2$, $R^3$ and $R^4$ are each independently OH, formylamide, alkylamide, alkylarylamide, aralkylamide, arylamide, alkylsulfonamide, N-alkyl-N-alkylsulfonamide, alkylarylsulfonamide, arylsulfonamide or aralkylsulfonamide, with the proviso that at least one of $R^1$, $R^2$, $R^3$ and $R^4$ is not OH.

In another embodiment, $R^1$, $R^2$, $R^3$ and $R^4$ are each independently OH, formylamide or alkylsulfonamide, with the proviso that at least one of $R^1$, $R^2$, $R^3$ and $R^4$ is not OH.

In another embodiment, $R^1$, $R^2$, $R^3$ and $R^4$ are each independently OH, formylamide or methylsulfonamide, with the proviso that at least one of $R^1$, $R^2$, $R^3$ and $R^4$ is not OH.

In another embodiment, $R^1$ and $R^2$ and/or $R^3$ and $R^4$ together are —NH—C(=O)—NH— and the others of $R^1$, $R^2$, $R^3$ and $R^4$ are are each independently OH, formylamide, alkylsulfonamide. In another embodiment, $R^1$ and $R^2$ together are —NH—C(=O)—NH— and $R^3$ and $R^4$ are each independently OH, formylamide or methylsulfonamide.

In another embodiment, $R^3$ and $R^4$ together are —NH—C(=O)—NH— and $R^1$ and $R^2$ are each independently OH, formylamide or methylsulfonamide.

In another embodiment, at least one of $R^1$, $R^2$, $R^3$ or $R^4$ is —NH—$CR^a$=$CR^b$—, or —NH—S($O_2$)$CR^cR^d$— and together with two adjacent carbon atoms of the phenyl ring forms a substituted or unsubstituted heterocyclic or substituted or unsubstituted heteroaromatic ring, and the others of $R^1$, $R^2$, $R^3$ and $R^4$ are each independently selected as in i) or ii); where $R^a$, $R^b$, $R^c$ and $R^d$ are each independently hydrogen or alkyl, and the others of $R^1$, $R^2$, $R^3$ and $R^4$ are each independently selected from OH, formylamide, alkylamide, alkylarylamide, aralkylamide, arylamide, alkylsulfonamide, alkylarylsulfonamide, arylsulfonamide and aralkylsulfonamide.

In another embodiment, at least one of $R^1$, $R^2$, $R^3$ or $R^4$ is —NH—CH=CH—, and together with two adjacent carbon atoms of the phenyl ring forms an indole ring, and the others of $R^1$, $R^2$, $R^3$ and $R^4$ are each independently selected from OH, formylamide, alkylamide, alkylarylamide, aralkylamide, arylamide, alkylsulfonamide, alkylarylsulfonamide, arylsulfonamide and aralkylsulfonamide.

In another embodiment, at least one of $R^1$, $R^2$, $R^3$ or $R^4$ is —NH—CH=CH— and together with two adjacent carbon atoms of the phenyl ring forms an indole ring, and the others of $R^1$, $R^2$, $R^3$ and $R^4$ are each independently selected from OH, formylamide, and methylsulfonamide.

In another embodiment, at least one of of $R^1$, $R^2$, $R^3$ or $R^4$ is —NH—S($O_2$)$CH_2$— and together with two adjacent carbon atoms of the phenyl ring forms a benzisothiazole-1,1-dioxide and the others of $R^1$, $R^2$, $R^3$ and $R^4$ are each independently selected from OH, formylamide, and methylsulfonamide.

In certain embodiments, the compounds have formula selected from:

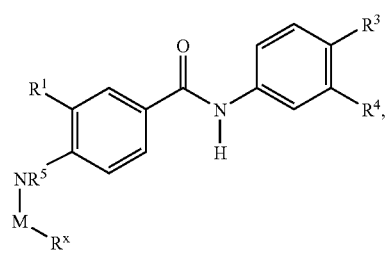

-continued

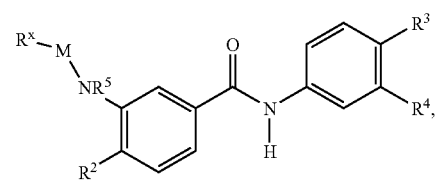

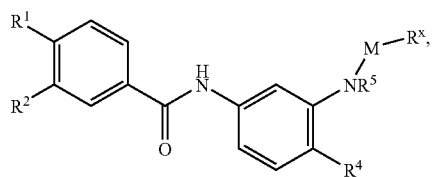

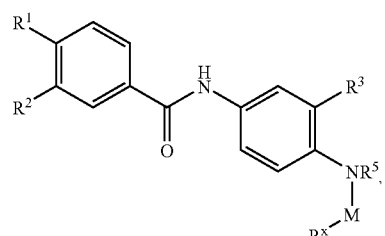

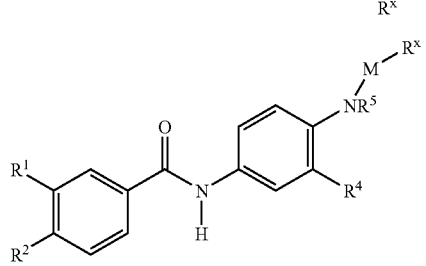

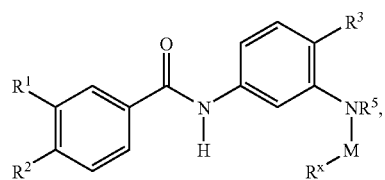

wherein i) when M is C(O), $R^x$ is hydrogen or alkyl and ii) when M is $S(O)_2$, $R^x$ is alkyl. In one embodiment, M is C(O) and $R^x$ is alkyl. In one embodiment, M is C(O) and $R^5$ is isopropyl. In one embodiment, M is $S(O)_2$ and $R^x$ is methyl.

In certain embodiments, the compounds have formula selected from:

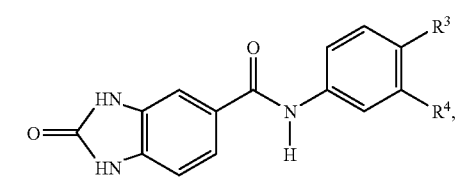

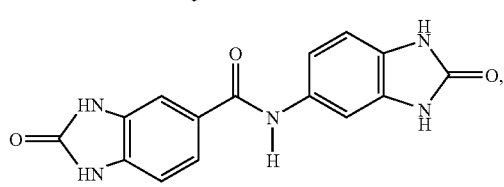

-continued

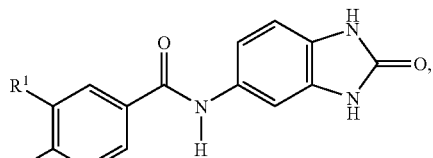

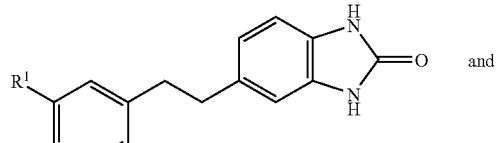

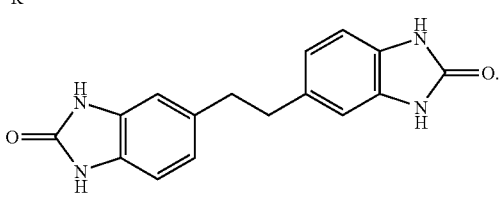

In certain embodiments, the compounds have formula selected from:

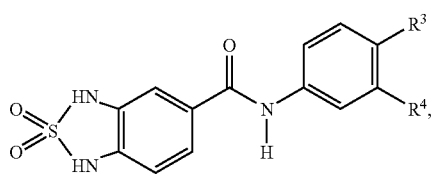

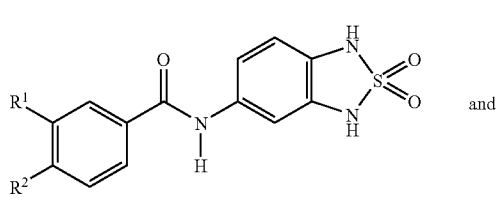

In other embodiments, the compounds are selected from formula:

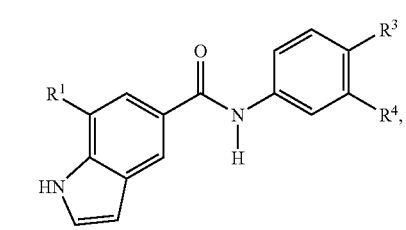

-continued

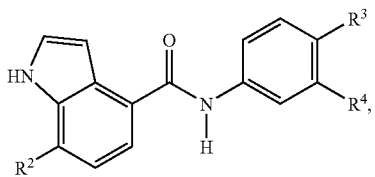

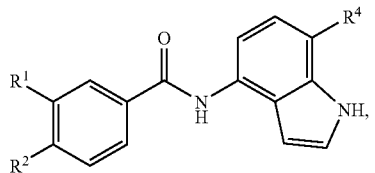

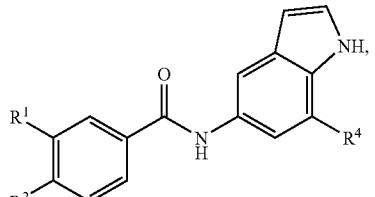

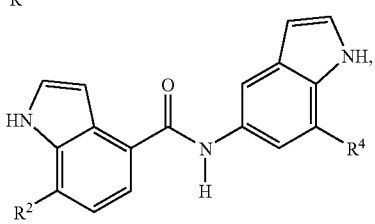

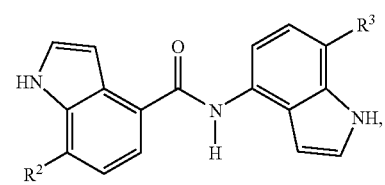

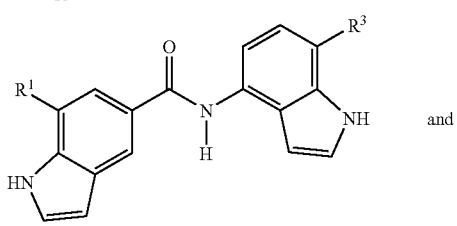 and

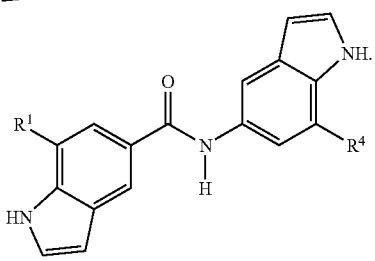

In certain embodiments, the compound has formula:

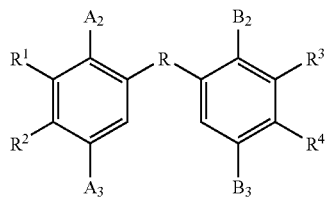 or

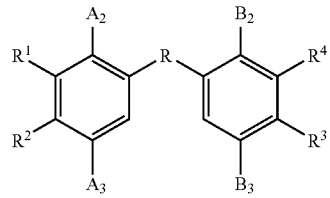

wherein $A_2$, $A_3$, $B_2$ and $B_3$ are each independently selected from halogen, cyanide, cyanate, thiocyanate, selenocyanate, trifluoromethoxy, azide, nitro and trifluoromethyl; $R^1$, $R^2$, $R^3$ and $R^4$ are selected as follows:

i) $R^1$ and $R^2$ are OH and $R^3$ and $R^4$ are each independently selected as described elsewhere herein or ii) $R^3$ and $R^4$ are OH and $R^1$ and $R^2$ are each independently selected as described elsewhere herein and the other variables are as described herein.

In certain embodiments, the compound has formula:

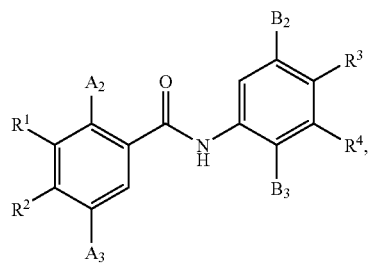

wherein $A_2$, $A_3$, $B_2$, and $B_3$ are each independently selected from halogen, pseudohalo, nitro, $^+NH_3$, $SO_3H$, carboxy and haloalkyl; and the other variables are as described elsewhere herein.

In certain embodiments, the compound has formula:

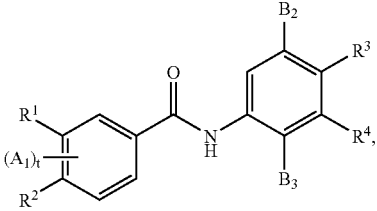

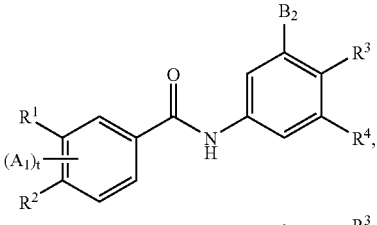

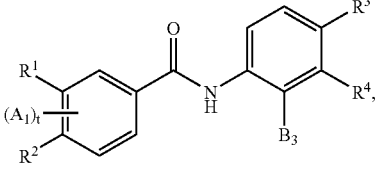

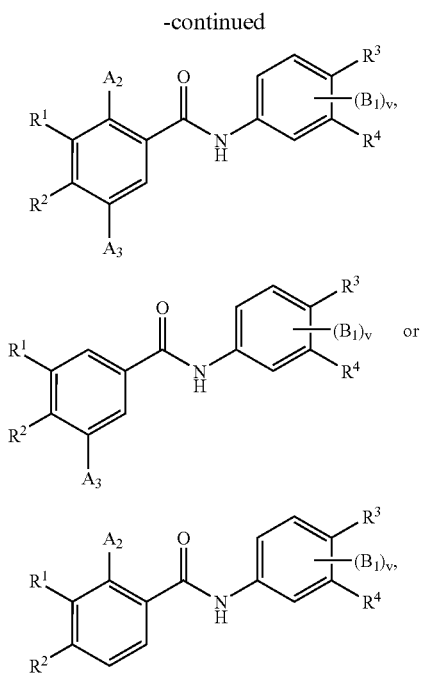

wherein the variables are as described elsewhere herein.

In certain embodiments, the compound has formula:

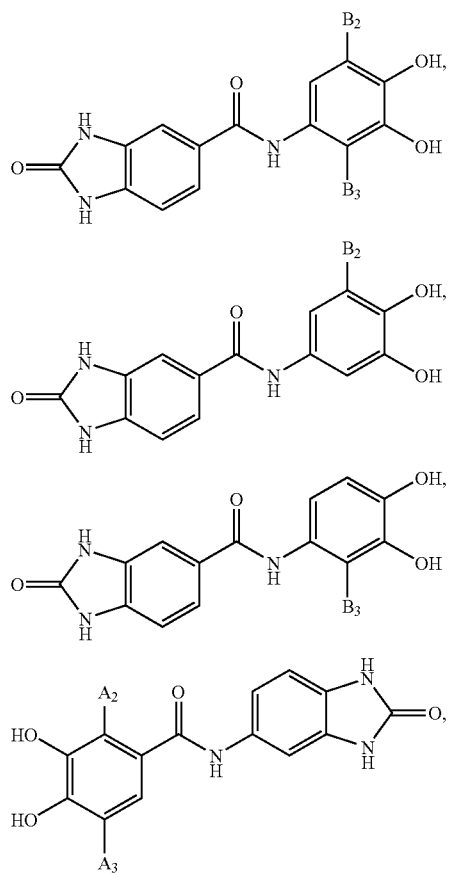

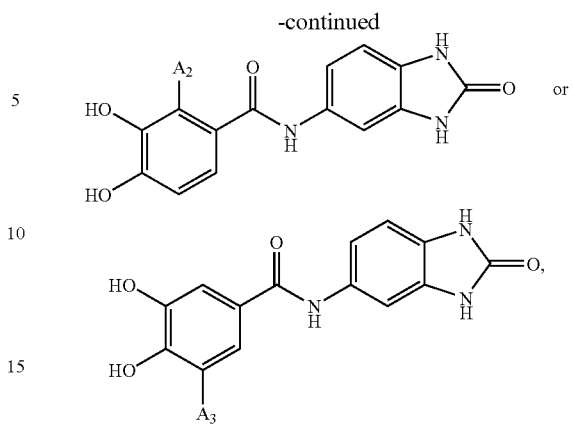

wherein the variables are as described elsewhere herein.

In one embodiment, the compound provided herein is selected from 2-Oxo-N-(2-oxo-2,3-dihydro-1H-benzo[d]imidazol-5-yl)-2,3-dihydro-1H-benzo[d]imidazole-5-carboxide; N-(3,4-dihydroxyphenyl)-2-oxo-2,3-dihydro-1H-benzo[d]imidazole-5-carboxamide and 3,4-dihydroxy-N-(2-oxo-2,3-dihydro-1H-benzo [d]imidazol-5-yl)benzamide.

In one embodiment, the compound is selected from a group of 3,4,3',4'-tetrahydroxybenzoin; 3,4,3',4'-tetrahydroxydesoxybenzoin; 3,4,3',4'-tetrahydroxydiphenylmethane; 1,2-bis (3,4-dihydroxyphenyl)ethane; 1,3-bis(3,4-dihydroxyphenyl) propane; 3,4,3',4'-tetrahydroxychalcone; 3,5-bis(3,4-dihydroxyphenyl)-1-methyl-2-pyrazoline; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-N,N'-dimethylethylenediamine; 2,5-bis(3,4-dihydroxybenzyl)-2,5-diaza[2.2.1]bicycloheptane; N,N'-bis(3,4-dihydroxybenzyl)-trans-1,2-diaminocyclohexane; N,N'-bis(3,4-dihydroxybenzyl)-trans-1,4-diaminocyclohexane; N,N'-bis(3,4-dihydroxybenzyl)-cis-1,3-bis(aminomethyl)cyclohexane; N-(3,4-dihydroxybenzyl)proline 3,4-dihydroxybenzylamide; 2-(3,4-dihydroxybenzyl)isoquinoline-3-carboxylic acid 3,4-dihydroxyphenethylamide; 2,6-bis(3,4-dihydroxybenzyl)cyclohexanone; 3,5-bis(3,4-dihydroxybenzyl)-1-methyl-4-piperidinone; 2,4-bis(3,4-dihydroxybenzyl)-3-tropinone; tris(3,4-dihydroxybenzyl)methane; α-(3,4-dihydroxybenzamido)-3,4-dihydroxycinnamic acid 3,4-dihydroxybenzyl amide; 4-(3,4-dihydroxybenzylaminomethylene)-2-(3,4-dihydroxyphenyl)oxazolin-5-one; 1,4-bis(3,4-dihydroxybenzoyl)piperazine; N,N'-bis(3,4-dihydroxybenzoyl)-N,N'-dimethylethylenediamine; 2,5-bis(3,4-dihydroxybenzoyl)-2,5-diaza[2.2.1]bicycloheptane; N,N'-bis(3,4-dihydroxybenzoyl)-trans-1,2-diaminocyclohexane; N,N'-bis(3,4-dihydroxybenzoyl)-cis-1,3-bis(aminomethyl)cyclohexane; 3,6-bis(3,4-dihydroxybenzyl)-2,5-diketopiperazine; 3,6-bis(3,4-dihydroxybenzylidene)-1,4-dimethyl-2,5-diketopiperazine; N-(3,4-dihydroxyphenylacetyl)proline-3,4-dihydroxyanilide; 2,3-bis(3,4-dihydroxyphenyl)butane; 1,3-bis(3,4-dihydroxybenzyl)benzene; 1,4-bis(3,4-dihydroxybenzyl)benzene; 2,6-bis(3,4-dihydroxybenzyl)pyridine; 2,5-bis(3,4-dihydroxybenzyl)thiophene; 2,3-bis(3,4-dihydroxybenzyl)thiophene; 1,2-bis(3,4-dihydroxyphenyl)cyclohexane; 1,4-bis(3,4-dihydroxyphenyl)cyclohexane; 3,7-bis(3,4-dihydroxyphenyl)bicyclo[3.3.0]octane; 2,3-bis (3,4-dihydroxyphenyl)-1,7,7-trimethyl-bicyclo[2.2.1]heptane; 1,2-bis(3,4-dihydroxyphenoxy)ethane; 1,3-bis(3,4-dihydroxyphenoxy)propane; trans-1,2-bis(3,4-dihydroxyphenoxy)cyclopentane; N-(3,4-dihydroxybenzyl)-

3-(3,4-dihydroxyphenoxy)-2-hydroxypropylamine; 3,4-dihydroxyphenoxyacetic acid 3,4-dihydroxyanilide; 3,4-dihydroxyphenoxyacetic acid 3,4-dihydroxybenzylamide; 3,4-dihydroxyphenoxyacetic acid 3,4-dihydroxyphenethylamide; 3,4-dihydroxybenzoic acid p-(3,4-dihydroxyphenoxy) anilide; 3,4-dihydroxybenzoic acid o-(3,4-dihydroxyphenoxy)anilide; 2,6-bis(3,4-dihydroxyphenoxy)pyridine; 3,4-dihydroxybenzoic acid 3,4-dihydroxyanilide; 3,4-dihydroxybenzoic acid 3,4-dihydroxybenzylamide; 3,4-dihydroxybenzoic acid 3,4-dihydroxyphenethylamide; 3,4-dihydroxyphenyl acetic acid 3,4-dihydroxyanilide; 3,4-dihydroxyphenylacetic acid 3,4-dihydroxybenzylamide; 3,4-dihydroxyphenylacetic acid 3,4-dihydroxyphenethylamide; 3-(3,4-dihydroxyphenyl)propionic acid 3,4-dihydroxyanilide; 3-(3,4-dihydroxyphenyl) propionic acid 3,4-dihydroxybenzylamide; 3-(3,4-dihydroxyphenyl)propionic acid 3,4-dihydroxyphenethylamide; 3,4-dihydroxycinnamic acid 3,4-dihydroxyanilide; 3,4-dihydroxycinnamic acid 3,4-dihydroxybenzylamide; 3,4-dihydroxycinnamic acid 3,4-dihydroxyphenethylamide; oxalic acid bis(3,4-dihydroxyanilide); oxalic acid bis(3,4-dihydroxybenzylamide); oxalic acid bis(3,4-dihydroxyphenethylamide); succinic acid bis(3,4-dihydroxyanilide); succinic acid bis(3,4-dihydroxybenzylamide); succinic acid bis(3,4-dihydroxyphenethylamide); maleic acid bis(3,4-dihydroxyanilide); maleic acid bis(3,4-dihydroxybenzylamide); fumaric acid bis(3,4-dihydroxyanilide); fumaric acid bis(3,4-dihydroxybenzylamide); bis(3,4-dihydroxybenzyl)amine; N-(3,4-dihydroxybenzyl)-3,4-dihydroxyphenethylamine; tris(3,4-dihydroxybenzyl)amine; 1,3-bis(3,4-dihydroxyphenyl)urea; 1-(3,4-dihydroxyphenyl)-3-(3,4-dihydroxybenzyl)urea; 1-(3,4-dihydroxyphenyl)-3-(3,4-dihydroxyphenethyl)urea; 3-deoxy-3-(3,4-dihydroxybenzyl)aminoepicatechin; 3-deoxy-3-(3,4-dihydroxyphenethyl)-aminoepicatechin; 2,3,6,7-tetrahydroxy-9,10-epoxy-9,10-dihydroacridine; 10-aminoanthracene-1,2,7,8-tetraol; acridine-1,2,6,7-tetraol; phenoxazine-2,3,7,8,10-pentaol; dibenzo[c,f][2,7]napthyridine-2,3,10,11-tetraol; and 6-methyl-5,6,6a,7-tetrahydro-4H-dibenzo[de,g]quinoline-2,10,11-triol, wherein at least one of the phenolic hydroxy groups of the compound is replaced by:

i) —$NR^5C(=O)R^6$, —$NR^7S(O_2)R^8$, wherein $R^5$ and $R^7$ are each independently hydrogen, substituted or unsubstituted alkyl, substituted or unsubstituted aryl, substituted or unsubstituted aralkyl, substituted or unsubstituted heteroaryl, substituted or unsubstituted heteroaralkyl, substituted or unsubstituted heterocyclyl or substituted or unsubstituted heterocyclylalkyl; and $R^6$ and $R^8$ are each independently substituted or unsubstituted alkoxy, substituted or unsubstituted aralkoxy, substituted or unsubstituted alkyl, substituted or unsubstituted heteroaryl, substituted or unsubstituted heterocyclyl, substituted or unsubstituted aryl or —$NR^9R^{10}$ where $R^9$ and $R^{10}$ are each independently hydrogen, alkyl, aralkyl, aryl, heteroaryl, heteroaralkyl or heterocyclyl;

ii) $R^1$ and $R^2$ and/or $R^3$ and $R^4$ together form a benzimidazolinone, benzothiadiazolidine-S,S-dioxide or benzoxazolinone; or iii) at least one of $R^1$, $R^2$, $R^3$ and $R^4$ together with an adjacent carbon atom forms a substituted or unsubstituted heterocyclic or substituted or unsubstituted heteroaromatic ring; wherein the substituents when present are selected from one or more substituents, in one embodiment one to three or four substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, imino, hydroxyimino, alkoxyimino, aryloxyimino, aralkoxyimino, alkylazo, arylazo, aralkylazo, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})_2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$, groups, which substitute atoms in a 1,2 or 1,3 arrangement, together form alkylenedioxy (i.e., —O—$(CH_2)_y$—O—), thioalkylenoxy (i.e., —S—$(CH_2)_y$—O—) or alkylenedithioxy (i.e., —S—$(CH_2)_y$—S—) where y is 1 or 2; or two $Q^1$ groups, which substitute the same atom, together form alkylene; wherein $R^{50}$ is hydroxy, alkoxy, aralkoxy, alkyl, heteroaryl, heterocyclyl, aryl or —$NR^{70}R^{71}$, where $R^{70}$ and $R^{71}$ are each independently hydrogen, alkyl, aralkyl, aryl, heteroaryl, heteroaralkyl or heterocyclyl, or $R^{70}$ and $R^{71}$ together form alkylene, azaalkylene, oxaalkylene or thiaalkylene;

$R^{51}$, $R^{52}$ and $R^{53}$ are each independently hydrogen, alkyl, aryl, aralkyl, heteroaryl, heteroaralkyl, heterocyclyl or heterocyclylalkyl;

$R^{60}$ is hydrogen, alkyl, aryl, aralkyl, heteroaryl, heteroaralkyl, heterocyclyl or heterocyclylalkyl; and $R^{63}$ is alkoxy, aralkoxy, alkyl, heteroaryl, heterocyclyl, aryl or —$NR^{70}R^{71}$.

In certain embodiments, the compound is selected from
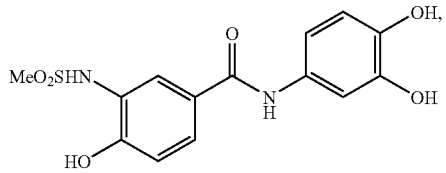
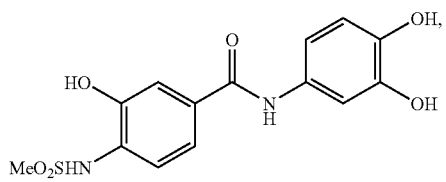
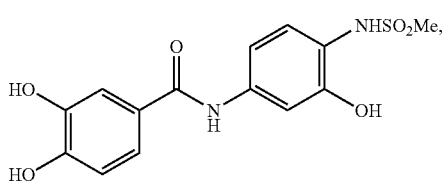
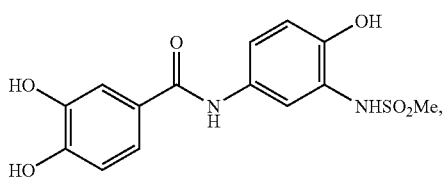
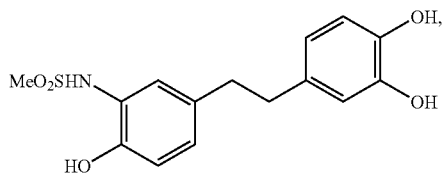
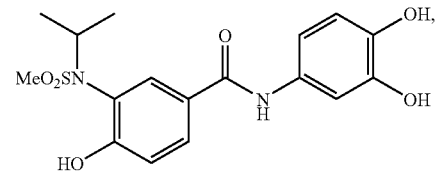
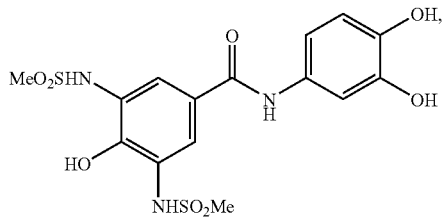
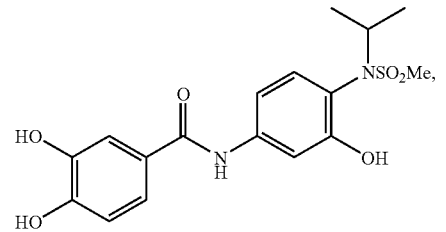
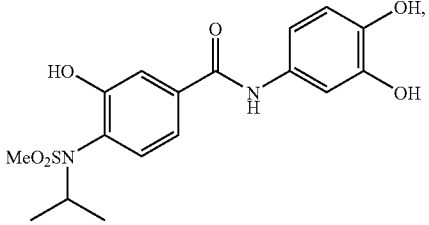
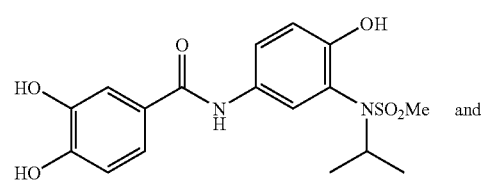 and
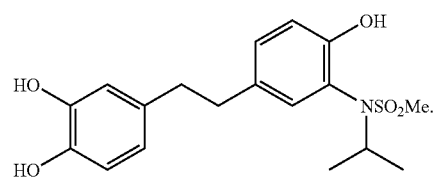
In other embodiments, the compound is selected from
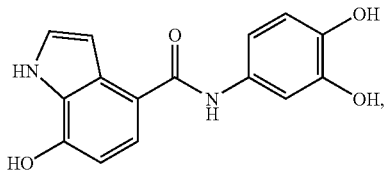
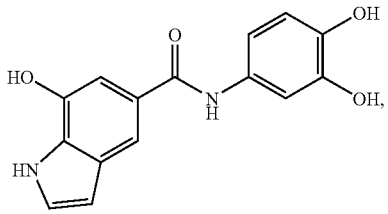
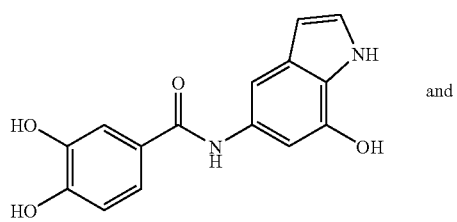 and
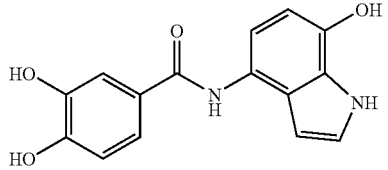

In other embodiments, the compound is selected from
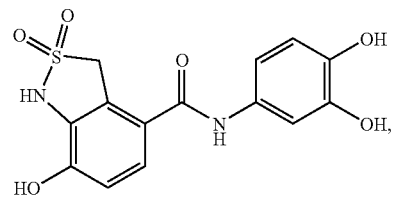
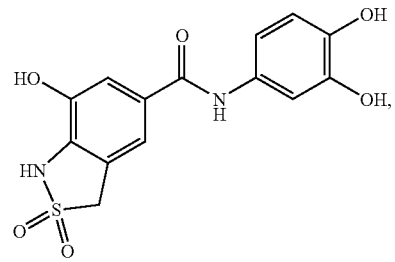
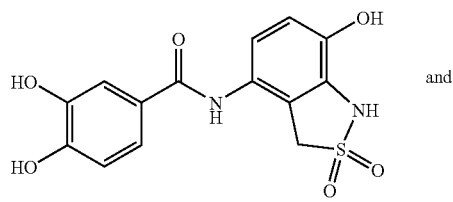
and
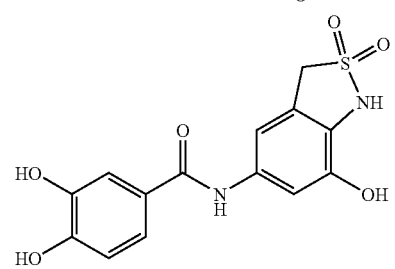
In certain embodiments, the compound is selected from
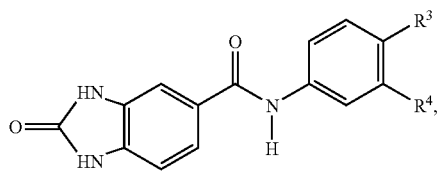
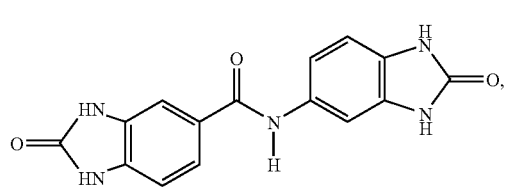
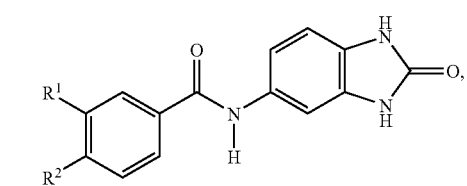
-continued
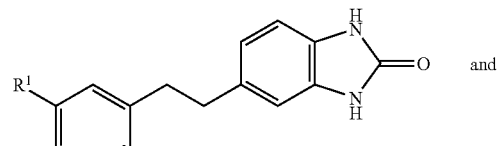
and
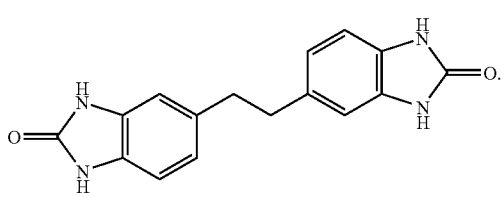
In certain embodiments, the compound is selected from
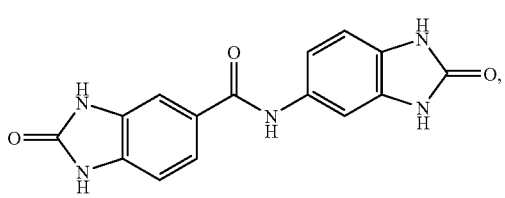
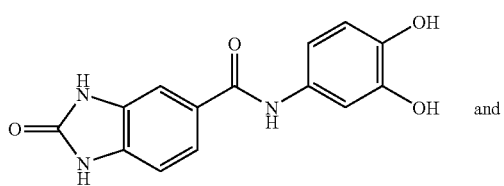
and
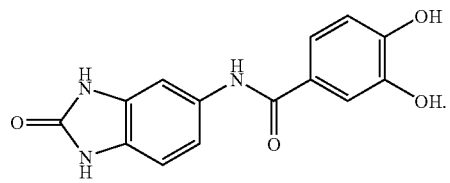
In certain embodiments, the compound is
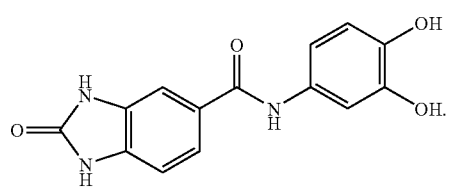
In other embodiments, the compound is selected from
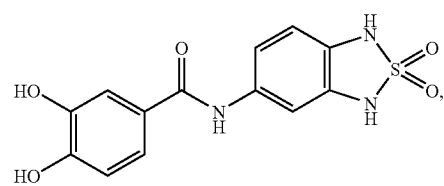

-continued
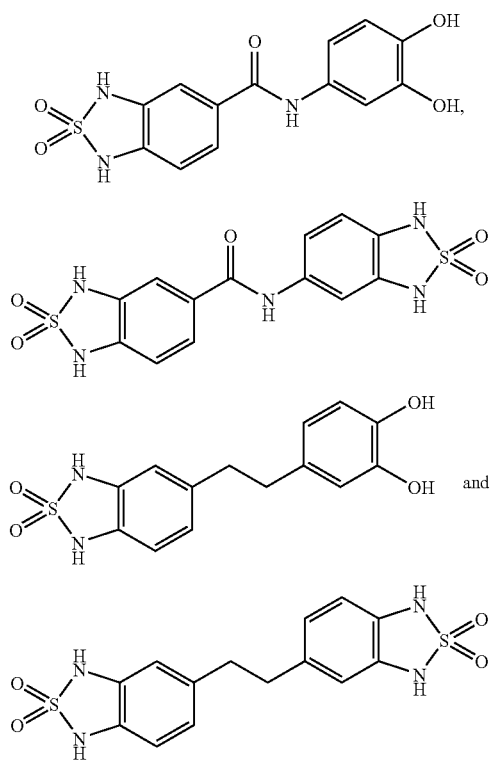
In other embodiments, the compound is selected from
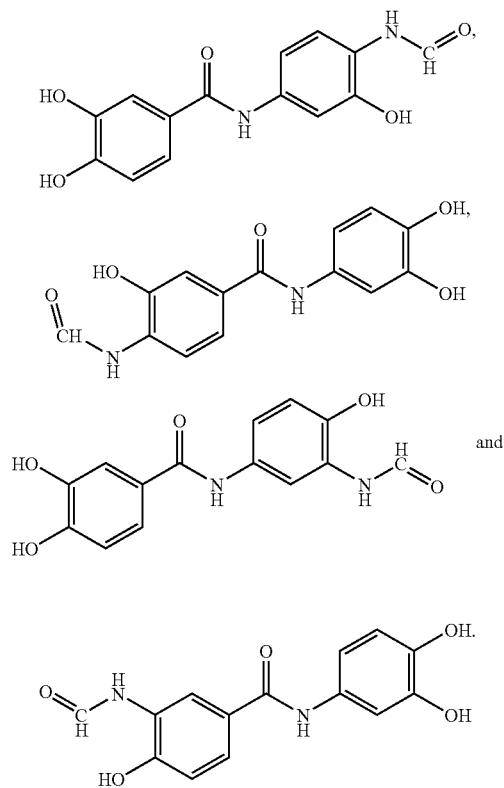
In certain embodiments, the compound is selected from
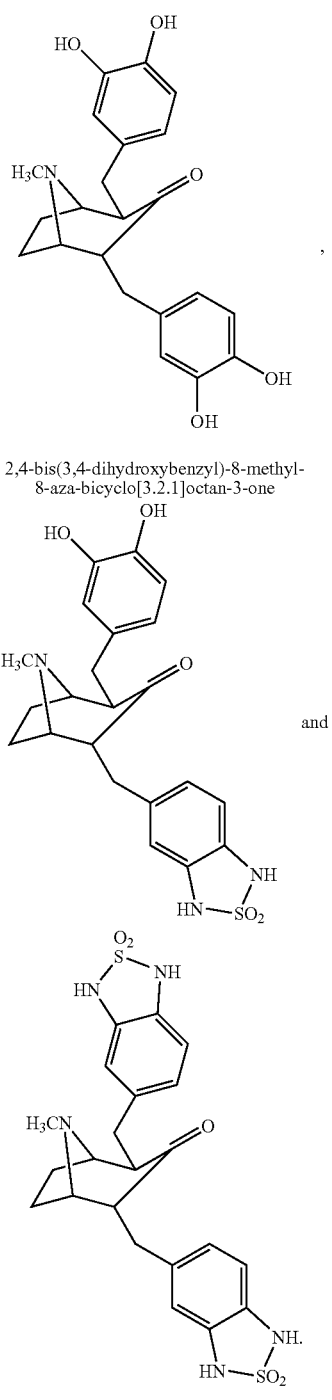
2,4-bis(3,4-dihydroxybenzyl)-8-methyl-8-aza-bicyclo[3.2.1]octan-3-one
In certain embodiments, the compounds provided herein have formula:
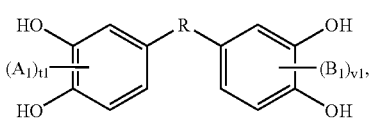
wherein $A_1$ and $B_1$, are each independently selected from halogen, pseudohalo, nitro, $^+NH_3$, $SO_3H$, carboxy and haloalkyl; and $t_1$ and $v_1$ are each independently 1 to 3; and the other variables are as described elsewhere herein.

In certain embodiments, $t_1$ and $v_1$ are each independently 1 or 2. In certain embodiments, $t_1$ is 1. In certain embodiments, $v_1$ is 1.

In certain embodiments, the compound is selected from

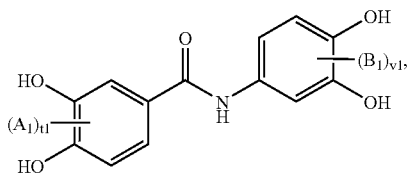

wherein variables are as described elsewhere herein.

In certain embodiments, the compound is selected from

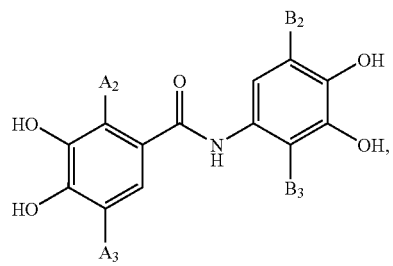

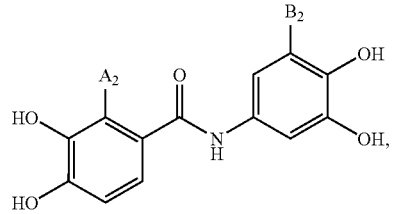

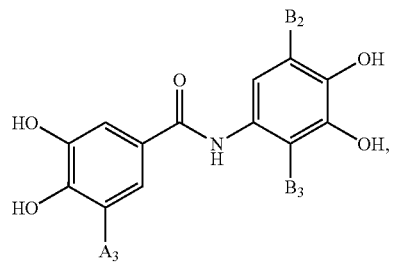

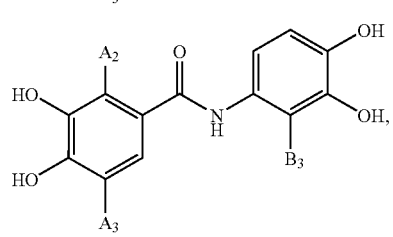

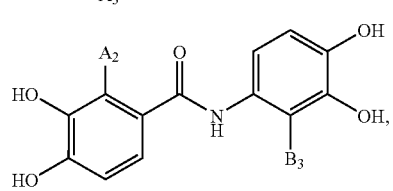

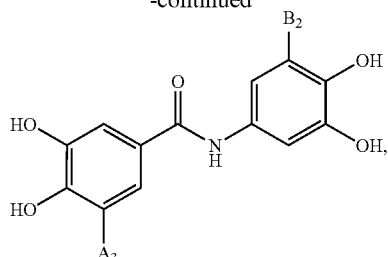

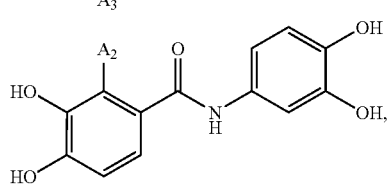

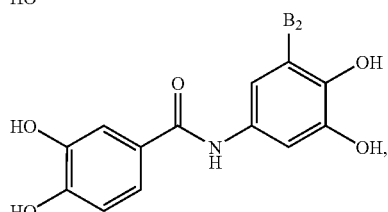

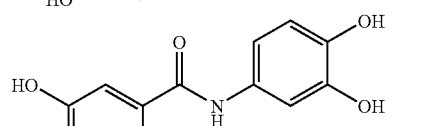

and

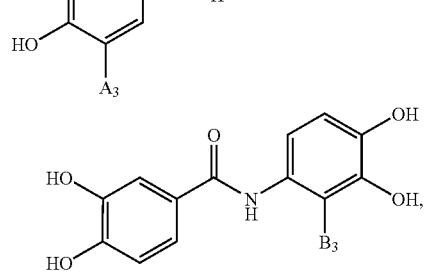

wherein $A_2$, $A_3$, $B_2$ and $B_3$ are each independently selected from Cl, F, cyanide, cyanate, thiocyanate, selenocyanate, trifluoromethoxy, azide, nitro and trifluoromethyl.

C. Preparation of the Compounds

The compounds provided herein can be prepared by standard synthetic methods follow describe the exemplary embodiments and are not purported to limit the scope of the claimed subject matter. It is intended that the specification, together with the following examples, be considered exemplary only, with the scope and spirit of the claimed subject matter being indicated by the claims that follow these examples. Other embodiments within the scope of claims herein will be apparent to one skilled in the art from consideration of the specification as described herein.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or Lancaster Synthesis Inc. (Windham, N.H.) or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In most cases, protective groups for the hydroxy groups are introduced and finally removed. Suitable protective groups are described in Greene et al., *Protective Groups in Organic Synthesis*, Second Edition, John Wiley and Sons, New York, 1991. Other starting materials or early intermediates may be prepared by elaboration of the materials listed above, for example, by methods well known to a person of ordinary skill in the art. The starting materials, intermediates, and compounds provided herein may be isolated and purified using conventional techniques, including precipitation, filtration, distillation, crystallization, chromatography, and the like. The compounds may be characterized using conventional methods, including physical constants and spectroscopic methods.

Provided herein are general reaction schemes for the preparation of exemplary compounds.

i) Achesom et al. J. Med. Chem. (1981) 24, 1300-1304, describe use of thionyl chloride for preparing benxthiadiazolidine S,S-dioxide as follows:

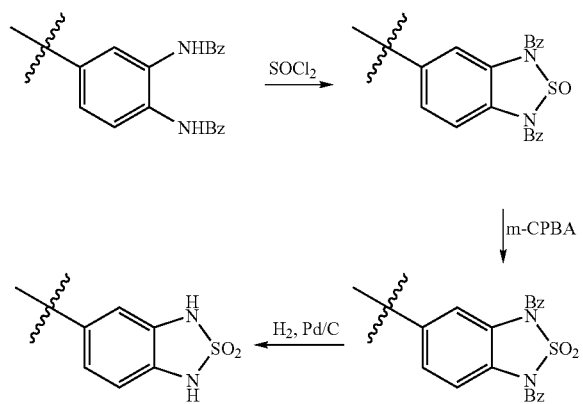

ii) Preparation of nitro benzothiadiazolidine S,S-dioxide is described by Burke et al. in JCS Perkin Transactions (1984) 11, 1851-4, as follows:

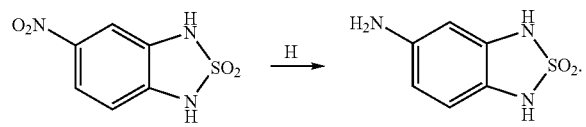

Further compounds provided herein can be prepared by reactions described in the literature as follows:

iii)

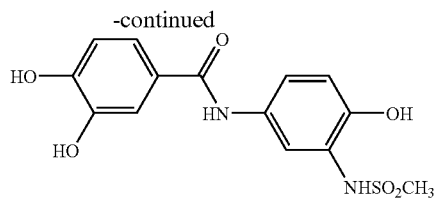

See, Roberts et al., J. O. Chen. (1997) 62, 568-577 iv)

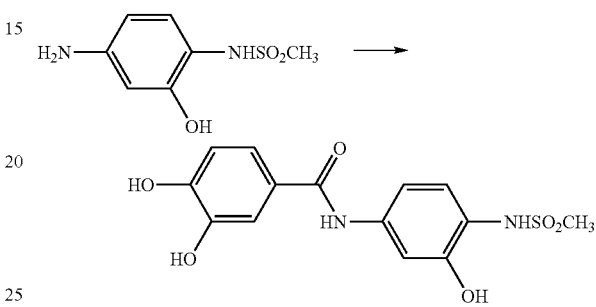

See, Hughes et al., J. Med. Chem. (1957) 18, 1077-1088.

D. Pharmaceutical Compositions and Administration

The compounds provided herein can be used as such, be administered in the form of pharmaceutically acceptable salts derived from inorganic or organic acids, or used in combination with one or more pharmaceutically acceptable excipients. The phrase "pharmaceutically acceptable salt" means those salts which are, within the scope of sound medical judgment, suitable for use in contact with the tissues without undue toxicity, irritation, allergic response, and the like, and are commensurate with a reasonable benefit/risk ratio. Pharmaceutically acceptable salts are well known in the art. The salts can be prepared either in situ during the final isolation and purification of the compounds provided herein or separately by reacting the acidic or basic drug substance with a suitable base or acid respectively. Typical salts derived from organic or inorganic acids salts include, but are not limited to hydrochloride, hydrobromide, hydroiodide, acetate, adipate, alginate, citrate, aspartate, benzoate, bisulfate, gluconate, fumarate, hydroiodide, lactate, maleate, oxalate, palmitoate, pectinate, succinate, tartrate, phosphate, glutamate, and bicarbonate. Typical salts derived from organic or inorganic bases include, but are not limited to lithium, sodium, potassium, calcium, magnesium, ammonium, monoalkylammonium such as meglumine, dialkylammonium, trialkylammonium, and tetralkylammonium.

In certain embodiments, the compositions contain a compound provided herein that is at least substantially pure. In general "pure" means better than 95% pure, and "substantially pure" means a compound synthesized such that the compound, as made as available for consideration into a therapeutic dosage, has only those impurities that can not readily nor reasonably be removed by conventional purification processes.

The mode of administration of the pharmaceutical compositions can be oral, rectal, intravenous, intramuscular, intracisternal, intravaginal, intraperitoneal, bucal, subcutaneous, intrasternal, nasal, or topical. The compositions can also be delivered at the target site through a catheter, an intracoronary stent (a tubular device composed of a fine wire mesh), a biodegradable polymer, or biological carriers including, but are not limited to antibodies, biotin-avidin complexes, and the like. Dosage forms for topical administration of a compound provided herein include powders, sprays, ointments and inhalants. The active compound is mixed under sterile conditions with a pharmaceutically acceptable carrier and any needed preservatives, buffers or propellants. Opthalmic formulations, eye ointments, powders and solutions are also provided herein.

Actual dosage levels of active ingredients and the mode of administration of the pharmaceutical compositions provided herein can be varied in order to achieve the effective therapeutic response for a particular patient. The phrase "therapeutically effective amount" of the compound provided herein means a sufficient amount of the compound to treat disorders, at a reasonable benefit/risk ratio applicable to any medical treatment. It will be understood, however, that the total daily usage of the compounds and compositions of the provided will be decided by the attending physician within the scope of sound medical judgment. The total daily dose of the compounds provided herein may range from about 0.0001 to about 1000 mg/kg/day. For purposes of oral administration, doses can be in the range from about 0.001 to about 5 mg/kg/day. If desired, the effective daily dose can be divided into multiple doses for purposes of administration; consequently, single dose compositions may contain such amounts or submultiples thereof to make up the daily dose. The specific therapeutically effective dose level for any particular patient will depend upon a variety of factors including the disorder being treated and the severity of the disorder; medical history of the patient, activity of the specific compound employed; the specific composition employed, age, body weight, general health, sex and diet of the patient, the time of administration, route of administration, the duration of the treatment, rate of excretion of the specific compound employed, drugs used in combination or coincidental with the specific compound employed; and the like.

The compounds provided can be formulated together with one or more non-toxic pharmaceutically acceptable diluents, carriers, adjuvants, and antibacterial and antifungal agents such as parabens, chlorobutanol, phenol, sorbic acid, and the like. Proper fluidity can be maintained, for example, by the use of coating materials such as lecithin, by the maintenance of the required particle size in the case of dispersions, and by the use of surfactants. In some cases, in order to prolong the effect of the drug, it is desirable to decrease the rate of absorption of the drug from subcutaneous or intramuscular injection. This can be accomplished by suspending crystalline or amorphous drug substance in a vehicle having poor water solubility such as oils. The rate of absorption of the drug then depends upon its rate of dissolution, which, in turn, may depend upon crystal size and crystalline form. Prolonged absorption of an injectable pharmaceutical form can be achieved by the use of absorption delaying agents such as aluminum monostearate or gelatin.

The compound provided herein can be administered enterally or parenterally in solid or liquid forms. Compositions suitable for parenteral injection may comprise physiologically acceptable, isotonic sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar and tragacanth, or mixtures of these substances.

The compounds provided herein can also be administered by injection or infusion, either subcutaneously or intravenously, or intramuscularly, or intrasternally, or intranasally, or by infusion techniques in the form of sterile injectable or oleaginous suspension. The compound may be in the form of a sterile injectable aqueous or oleaginous suspensions. These suspensions may be formulated according to the known art using suitable dispersing of wetting agents and suspending agents that have been described above. The sterile injectable preparation may also be a sterile injectable solution or suspension in a non-toxic parenterally-acceptable diluent or solvent for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oils may be conventionally employed including synthetic mono- or diglycerides. In addition fatty acids such as oleic acid find use in the preparation of injectables. Dosage regimens can be adjusted to provide the optimum therapeutic response. For example, several divided dosages may be administered daily or the dosage may be proportionally reduced as indicated by the exigencies of the therapeutic situation.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. Tablets contain the compound in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia, and lubricating agents, for example, magnesium stearate or stearic acid or talc. The tablets may be uncoated or they may be coated by known techniques to delay disintegration and absorption in the gastrointestinal tract and thereby provide a sustained action over a longer period. For example, a time delay material such as glycerol monostearate or glycerol distearate may be employed. Formulations for oral use may also be presented as hard gelatin capsules wherein the compound is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Aqueous suspensions contain the compound in admixture with excipients suitable for the manufacture of aqueous suspensions. Such excipients are suspending agents, for example, sodium carboxymethylcellulose, methylcellulose, hydroxypropylmethyl cellulose, sodium alginate, polyvinylpyrrolidone, gum tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids such as hexitol such as polyoxyethylene sorbitol monooleate, or condensation products of ethylene oxide with partial esters from fatty acids and a hexitol anhydrides, for example, polyethylene sorbitan monooleate. The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the compound in a vegetable oil, for example arachis oil, olive oil, sesame oil, or coconut oil or in a mineral oil such as liquid paraffin. The oily suspensions may contain a thickening agent, for example beeswax, hard paraffin or cetyl alcohol. Sweetening agents, such as those set forth below, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already described above. Additional excipients, for example sweetening, flavoring and agents, may also be present.

The compounds provided herein may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents. Syrups and elixirs may be formulated with sweetening agents, for example, glycerol, sorbitol or sucrose. Such formulations may also contain a demulcent, a preservative and flavoring and coloring agents.

In one embodiment, the compounds are formulated in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labeled or accompanied by a label indicating the intended method of treatment, such as the treatment of an amyloid disease, for example an amyloidosis such as Alzheimer's disease or a disease associated with α-synuclein/NAC fibril formation such as Parkinson's disease. Compositions for rectal or vaginal administration are preferably suppositories which can be prepared by mixing the compounds provided herein with suitable non-irritating excipients or carriers such as cocoa butter, polyethylene glycol or a suppository wax which are solid at room temperature but liquid at body temperature and therefore melt in the rectum or vaginal cavity and release the active compound.

Compounds provided herein can also be administered in the form of liposomes. Methods to form liposomes are known in the art (Prescott, Ed., *Methods in Cell Biology* 1976, Volume XIV, Academic Press, New York, N.Y.) As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound provided herein, stabilizers, preservatives, excipients and the like. The preferred lipids are natural and synthetic phospholipids and phosphatidyl cholines (lecithins).

The compounds provided herein can also be administered in the form of a 'prodrug' wherein the active pharmaceutical ingredients, represented by Formulas 1-3, are released in vivo upon contact with hydrolytic enzymes such as esterases and phophatases in the body. The term "pharmaceutically acceptable prodrugs" as used herein represents those prodrugs of the compounds provided herein, which are, within the scope of sound medical judgment, suitable for use in contact with the tissues without undue toxicity, irritation, allergic response, and the like, commensurate with a reasonable benefit/risk ratio, and effective for their intended use. A thorough discussion is provided in T. Higuchi and V. Stella (Higuchi, T. and Stella, V. Pro-drugs as Novel Delivery Systems, V. 14 of the A.C.S. Symposium Series; Edward B. Roche, Ed., *Bioreversible Carriers in Drug Design* 1987, American Pharmaceutical Association and Pergamon Press), which is incorporated herein by reference.

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Article of Manufacture

The compounds or pharmaceutically acceptable derivatives may be packaged as articles of manufacture containing packaging material, a compound or pharmaceutically acceptable derivative thereof provided herein, which is effective for treatment, prevention or amelioration of one or more symptoms of amyloidosis and synuclein diseases, within the packaging material, and a label that indicates that the compound or composition, or pharmaceutically acceptable derivative thereof, is used for treatment, prevention or amelioration of one or more symptoms of amyloidosis and synuclein diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for amyloidosis and synuclein diseases.

Sustained Release Formulations

Also provided are sustained release formulations to deliver the compounds to the desired target (i.e. brain or systemic organs) at high circulating levels (between $10^{-9}$ and $10^{-4}$ M).

In a certain embodiment for the treatment of Alzheimer's or Parkinson's disease, the circulating levels of the compounds is maintained up to $10^{-7}$ M. The levels are either circulating in the patient systemically, or in one embodiment, present in brain tissue, and in a another embodiments, localized to the amyloid or α-synuclein fibril deposits in brain or other tissues.

It is understood that the compound levels are maintained over a certain period of time as is desired and can be easily determined by one skilled in the art. In one embodiment, the administration of a sustained release formulation is effected so that a constant level of therapeutic compound is maintained between $10^{-8}$ and $10^{-6}$ M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions provided herein. Thus, single unit dosage forms suitable for oral administration, such as, but not limited to, tablets, capsules, gelcaps, caplets, powders and the like, that are adapted for sustained release are contemplated herein.

In one embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are contemplated herein. The sustained release formulation is encapsulated by coating particles or granules of the pharmaceutical compositions provided herein with varying thickness of slowly soluble polymers or by microencapsulation. In one embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, in one embodiment 20 to 25%, and the amount of coating will be from 10 to 25% of the weight of the active material, and in another embodiment, 15 to 20% of the weight of active material. Any conventional pharmaceutically acceptable plasticizer may be incorporated into the coating.

The compounds provided herein can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations provided herein are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds.

Preparations for oral administration may be suitably formulated to give controlled release of the active compound. In one embodiment, the compounds are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compositions provided herein may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and non-toxic, include but are not limited to hydrogels, silicones, polyethylenes, ethylene-vinyl acetate copolymers, or biodegradable polymers.

E. Evaluation of the Activity of the Compounds

The biological activity of the compounds provided herein as disruptors/inhibitors of Alzheimer's disease β-amyloid protein (Aβ) fibrils, type 2 diabetes IAPP fibrils and Parkinson's disease NAC fibrils was assessed by determining the efficacy of the compounds to cause a disassembly/disruption of pre-formed amyloid fibrils of Alzheimer's disease (i.e. consisting of Aβ 1-42 fibrils), IAPP fibrils and Parkinson's disease NAC fibrils. In one study, Thioflavin T fluorometry was used to determine the effects of the compounds, and of EDTA (as a negative control). In this assay Thioflavin T binds specifically to fibrillar amyloid, and this binding produces a fluorescence enhancement at 485 nm that is directly proportional to the amount of fibrils present. The higher the fluorescence, the greater the amount of fibrils present (Naki et al, $Lab.\ Invest.$ 65:104-110, 1991; Levine III, $Protein\ Sci.$ 2:404-410, 1993; $Amyloid.\ Int.\ J.\ Exp.\ Clin.\ Invest.$ 2:1-6, 1995). The disruption of Aβ 1-42, even in its monomeric form, was confirmed by a study involving the use of SDS-PAGE and Western blotting methods.

In the Congo red binding assay the ability of a given test compound to alter amyloid (Aβ 1-42 fibrils, IAPP fibrils or NAC fibrils) binding to Congo red was quantified. In this assay, Aβ 1-42 fibrils, IAPP fibril or NAC fibrils and test compounds were incubated for 3 days and then vacuum filtered through a 0.2 μm filter. The amount of Aβ 1-42 fibrils, IAPP fibrils or NAC fibrils retained in the filter was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic Aβ 1-42 fibrils, IAPP fibrils or NAC fibrils.

F. Combination Therapy

In another embodiment, the compounds may be administered in combination, or sequentially, with another therapeutic agent. Such other therapeutic agents include those known for treatment, prevention, or amelioration of one or more symptoms of amyloidosis and synuclein diseases. Such therapeutic agents include, but are not limited to, donepezil hydrochloride (Aracept), rivastigmine tartrate (Exelon), tacrine hydrochloride (Cognex) and galantamine hydrobromide (Reminyl).

G. Methods of Use of the Compounds and Compositions

The compounds and compositions provided herein are useful in methods of treatment, prevention, or amelioration of one or more symptoms of amyloid diseases or disorders, including but not limited to diseases associated with the formation, deposition, accumulation, or persistence of amyloid fibrils diseases associated with the formation, deposition, accumulation, or persistence of amyloid fibrils. In one embodiment, the fibrils of an amyloid protein are selected from the group of Aβ amyloid, AA amyloid, AL amyloid, IAPP amyloid, PrP amyloid, $\alpha_2$-microglobulin amyloid, transthyretin, prealbumin, and procalcitonin. In certain embodiments, the fibrils of an amyloid protein are Aβ amyloid and IAPP amyloid. In certain embodiments, the compounds and compositions provided herein are used for treatment, prevention, or amelioration of one or more symptoms of diseases including, but not limited to Alzheimer's disease, Down's syndrome, dementia pugilistica, multiple system atrophy, inclusion body myositosis, hereditary cerebral hemorrhage with amyloidosis of the Dutch type, Nieman-Pick disease type C, cerebral β-amyloid angiopathy, dementia associated with cortical basal degeneration, the amyloidosis of type 2 diabetes, the amyloidosis of chronic inflammation, the amyloidosis of malignancy and Familial Mediterranean Fever, the amyloidosis of multiple myeloma and B-cell dyscrasias, the amyloidosis of the prion diseases, Creutzfeldt-Jakob disease, Gerstmann-Straussler syndrome, kuru, scrapie, the amyloidosis associated with carpal tunnel syndrome, senile cardiac amyloidosis, familial amyloidotic polyneuropathy, and the amyloidosis associated with endocrine tumors. In certain embodiments, the diseases are Alzheimer's disease or type 2 diabetes.

Also provided are methods to inhibit or prevent α-synuclein/NAC fibril formation, methods to inhibit or prevent α-synuclein/NAC fibril growth, and methods to cause disassembly, disruption, and/or disaggregation of preformed α-synuclein/NAC fibrils and α-synuclein/NAC-associated protein deposits.

In certain embodiments, the synuclein diseases or synucleinopathies treated, prevented or whose symptoms are ameliorated by the compounds and compositions provided herein include, but are not limited to diseases associated with the formation, deposition, accumulation, or persistence of synuclein fibrils, including α-synuclein fibrils. In certain embodiments, such diseases include Parkinson's disease, familial Parkinson's disease, Lewy body disease, the Lewy body variant of Alzheimer's disease, dementia with Lewy bodies, multiple system atrophy, and the Parkinsonism-dementia complex of Guam.

The following non-limiting Examples are given by way of illustration only and are not considered a limitation of the subject matter, many apparent variations of which are possible without departing from the spirit or scope thereof.

EXAMPLES

General Experimental Procedures

All solvents were distilled before use and were removed by rotary evaporation at temperatures up to 35°. Merck silica gel 60, 200-400 mesh, 40-63 μm, was used for silica gel flash chromatography. TLC was carried out using Merck DC•plastikfoiien Kieselgel 60 $F_{254}$, first visualised with a UV lamp, and then by dipping in a vanillin solution (1% vanillin, 1% $H_2SO_4$ in EtOH), and heating. Mass spectra were recorded on a Kratos MS-80 instrument. NMR spectra, at 25°, were recorded at 500 or 300 MHz for $^1$H and 125 or 75 MHz for $^{13}$C on Varian INOVA-500 or VXR-300 spectrometers. Chemical shifts are given in ppm on the δ scale referenced to the solvent peaks $CHCl_3$ at 7.25 and $CDCl_3$ at 77.0 ppm or $(CH_3)_2CO$ at 2.15 and $(CD_3)_2CO$ at 30.5 ppm or $CH_3OD$ at 3.30 and $CD_3OD$ at 39.0 ppm.

HPLC Conditions

The analytical HPLC equipment consisted of a Waters 717 autosampler, 600 pump and controller, and a 2487 UV detector controlled by Omega software for method 2, and a Waters 717 autosampler, 600 pump and controller, and a 490 UV detector controlled by Millennium software for method 1. Samples were analysed by using an RP-18 semi-preparative column (Phenomenex Prodigy 5 mm C18 100A, 250×4.6 mm) with a guard column (Phonomenex SecurityGuard cartridge containing a C18 ODS 4×3 mm, 5 mm column) fitted at 30° C. Samples (5 mL) were analysed using a mobile phase flow rate of 5.0 mL/min, with UV detection at 280 nm.

Solvent A—$CH_3CN$

Solvent B—$H_2O$ containing 0.1% TFA

| | Method 1 | |
|---|---|---|
| Time (minutes) | solvent A | solvent B |
| 0 | 11 | 89 |
| 20 | 11 | 89 |
| 30 | 100 | 0 |
| 31 | 11 | 89 |
| 40 | 11 | 89 |

HPLC Method 2 (for Compounds DC-0051-B1 Through DC-0051-B4)

The method 2 constitutes using a C18 column with 2.1×50 mm dimensions. The run time is set at 7 minutes. The mobile phase included (A) acetonitrile with 0.05% TFA, and (B) distilled water with 0.05% TFA. All runs with method 2 employed a gradient elution from 10% to 90% of solvent A.

Example 1

Synthesis of
3-methanesulfonylamino-4-hydroxybenzoic acid
3,4-dihydroxyanilide (DC-0051-S1; also referred to
as DC-0051-CB)

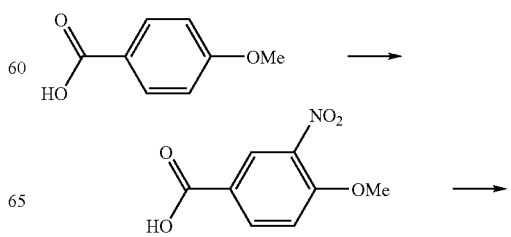

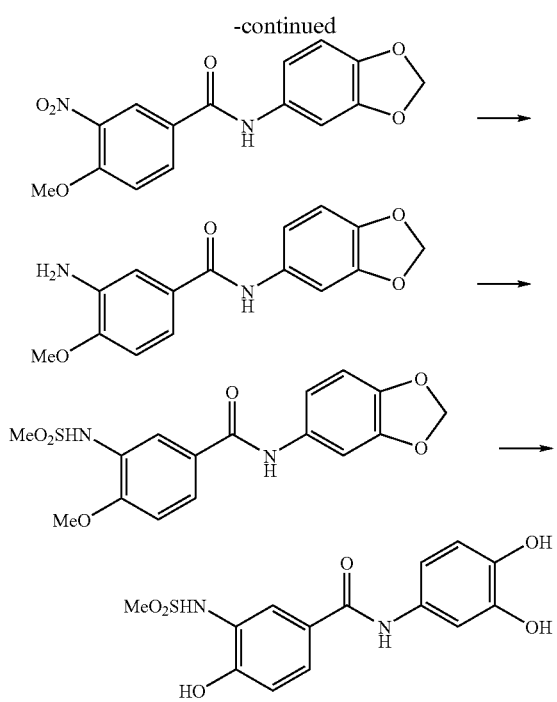

Formation of the methanesulfonylamine derivative of the amide DC-0051 was carried out by initial formation of the known 3-nitro-4-methoxybenzoic acid, then formation of the anilide of with 3,4-methylenedioxyaniline which gave 3-nitro-4-methoxy-amide. Catalytic reduction followed by immediate mesylation gave the mesylamine which was demethylated simply by reaction with borontribromide to give 3-methanesulfonylamino-4-hydroxybenzoic acid 3,4-dihydroxyanilide (DC-0051-S1; also referred to as DC-0051-CB)).

A) 3-Nitro-4-methoxybenzoic acid.

To a suspension of p-anisic acid (3 g) in acetic anhydride (20 ml) at 0° C. was added dropwise conc. nitric acid (6 ml). The resultant clear solution was allowed to come to room temperature, then stood for 30 minutes. The mixture was poured onto ice (100 ml) and the white solid formed filtered off, then washed with more ice cold water to give the product (2.8 g, 72%).

H NMR ((CD$_3$)$_2$CO) 8.44 (1 H, d, J 2 Hz), 8.29 (1 H, dd, J 2, 8 Hz), 7.51 (1 H, d, J 8 Hz) and 4.11 (3H, s).

B) 3-Nitro-4-methoxybenzoic acid 3,4-methylenedioxyanilide.

A suspension of 3-nitro-4-methoxybenzoic acid (1.4 g) in thionyl chloride (10 ml) was heated at reflux for one hour. The solvents were removed in vacuo to give the acid chloride as a white solid, which was redissolved in dry dichloromethane (20 ml) and a mixture of pyridine (1 ml) and 3,4-methylenedioxyaniline (1 g) in dichloromethane (5 ml) was added dropwise. The mixture was left at room temperature for 24 hours, then more dichloromethane (50 ml) and hydrochloric acid (1 M, 50 ml) added and the precipitate filtered off and washed with water to give 3-nitro-4-methoxybenzoic acid 3,4-methylenedioxyanilide (1.72 g, 72%).

$^1$H NMR ((CD$_3$)$_2$CO) 9.79 (1 H, bs, NH), 8.58 ($^1$H, d, J 2 Hz), 8.41 (1 H, dd, J 2, 8 Hz), 7.63 (1 H, d, J 2 Hz), 7.62 (1 H, d, J 8 Hz), 7.35 (1 H, dd, J 2, 8 Hz), 6.96 (1 H, d, J 8 Hz), 6.15 (2H, s) and 4.22 (3H, s).

C) 3-methanesulfonylamino-4-methoxybenzoic acid 3,4-methylenedioxyanilide.

A suspension of 3-Nitro-4-methoxybenzoic acid 3,4-methylenedioxyanilide (0.44 g) in methanol (20 ml) with formic acid (1 ml) was stirred under hydrogen with palladium hydroxide on carbon (10%, 200 mg) for 5 hours. The mixture was filtered through cotton wool and the solvents removed In vacuo. Purification by column chromatography over silica gel eluting with 20 to 100% ethyl acetate in dichloromethane gave the pure amine (270 mg, 68%). This was immediately dissolved in pyridine (5 ml) and methanesulfonyl chloride (0.2 ml) added dropwise, then the mixture left at room temperature overnight. Hydrochloric acid (1 M, 100 ml) and ethyl acetate (100 ml) were added, then the organic layer dried and evaporated in vacuo to give the crude product. Crystallisation from dichloromethane gave 3-methanesulfonylamino-4-methoxybenzoic acid 3,4-methylenedioxyanilide as white crystals (155 mg, 47%).

1H NMR ((CD$_3$)$_2$CO) 9.62 (1 H, bs, NH), 8.07 (1 H, d, J 2 Hz), 7.97 (1 H, bs, NH), 7.87 (1 H, dd, J 2, 8 Hz), 7.55 (1 H, d, J 2 Hz), 7.22 (1 H, dd. J 2, 8 Hz), 7.21 (1 H, d, J 8 Hz), 6.83 (1 H, d, J 8 Hz), 6.13 (2H, s), 4.14 (3H, s) and 3.16 (3H, s).

D) 3-Methanesulfonylamino-4-hydroxybenzoic acid 3,4-dihydroxyanilide (DC0051-S1), see, J. van Alphen. Rec. trav. Chim. 1929, 48, 1112-23.

To a stirred suspension of 3-methanesulfonylamino-4-methoxybenzoic acid 3,4-methylenedioxyanilide (100 mg) in dry CH$_2$Cl$_2$ (20 mL) under nitrogen, was added boron tribromide (0.2 ml) then stirring continued for a further 20 hours. Methanol (50 ml-) was added carefully, then the solvent evaporated in vacuo to a volume of 1 ml, this was repeated 2 more times. Purification by crystallisation from methanol gave 3-methanesulfanylamino-4-hydroxybenzoic acid-3,4-dihydroxyanilide (DC0051-A1) (45 mg, 47%) as pale brown crystals.

H NMR ((CD$_3$)$_2$CO) 9.68 (1 H, bs, NH), 927 (1 H, bs, NH), 8.03 ($^1$H, d, J 2 Hz), 8.02 (1 H, bs, OH), 7.91 (1 H, bs, OH), 7.76 (1 H, dd, J 2, 8 Hz), 7.75 (1 H, bs, OH), 7.49 (1 H, d, J 2 Hz), 7.10 (1 H, dd, J 2, 8 Hz), 7.09 (1 H, d, J 8 Hz), 6.79 (1 H, d, J 8 Hz) and 3.05 (3H, s).

M/z 337 ((M-H), 100%).

Hplc (method 1) 21.1 min.

Example 2

3-Hydroxy-4-methanesulfonylamino-N-(3,4-dihydroxyphenyl)benzamide, (DC0051-S8; also referred to as DC-0051-DB)

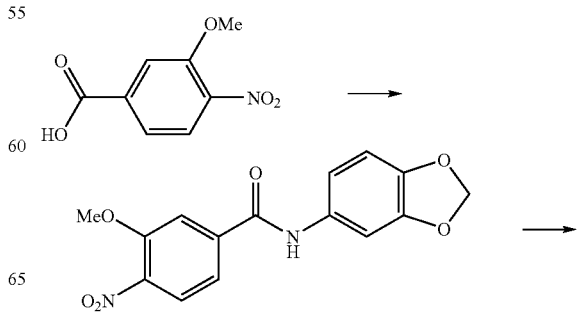

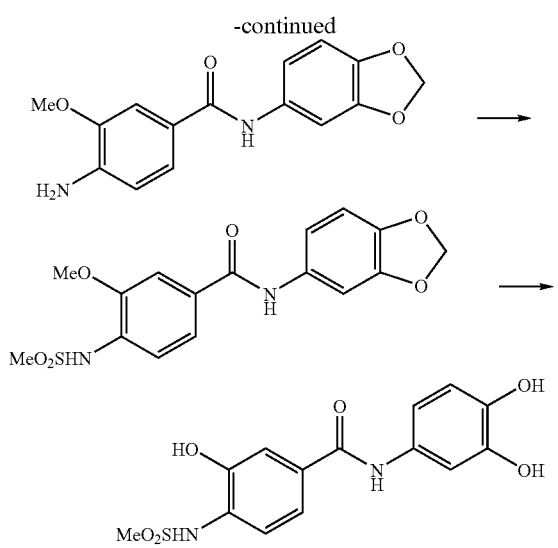

Formation of the anilide of 3-methoxy-4-nitrobenzoic acid with 3,4-methylenedioxyaniline gave 3-nitro-4-methoxy-amide. Reduction by catalytic hydrogenation followed by immediate mesylation gave the mesylamine. This was demethylated by reaction with borontribromide to give 3-Hydroxy-4-methanesulfonylamino-N-(3,4-dihydroxyphenyl)benzamide (DC-0051-S8; also referred to as DC0051-BD).

A) 3-Methoxy-4-nitro-N-(3,4-methylenedioxyphenyl)benzamide

A suspension of 3-methoxy-4-nitrobenzoic acid (0.5 g) in thionyl chloride (10 ml) was heated at reflux for one hour. The solvents were removed in vacuo to give the acid chloride as a white solid. The acid chloride was dissolved in dry dichloromethane (10 ml) and a mixture of pyridine (0.5 ml) and 3,4-methylenedioxyaniline (0.4 g) in dichloromethane (5 ml) was added dropwise. The mixture was left at room temperature for 24 hours, then dichloromethane (50 ml) and hydrochloric acid (1 M, 50 ml) added and the precipitate filtered off and washed with water to give 3-Methoxy-4-nitro-N-(3,4-methylenedioxyphenyl)benzamide (0.43 g, 54%). $^1$H NMR ((CD$_3$)$_2$CO) 9.79 (1 H, bs, NH), 8.03 (1 H, d, J 8 Hz), 7.98 (1 H, d, J 2 Hz), 7.78 (1 H, dd, J 2, 8 Hz), 7.63 (1 H, d, J 2 Hz), 7.32 (1 H, dd, J 2, 5 Hz), 6.93 (1 H, d, J 5Hz), 6.11 (2H, s) and 4.17 (3H, s).

B) 3-Methoxy-4-methanesulfonylamino-N-(3,4-methylenedioxyphenyl)benzamide.

A suspension of 3-Methoxy-4-nitro-N-(3,4-methylenedioxyphenyl)benzamide (100 mg) in methanol (20 ml) was stirred under hydrogen with palladium on carbon (10%, 50 mg) for 18 hours.

The solvents were removed in vacuo to give a brown gum. The residue was dissolved in pyridine (0.5 ml) and cooled to 0° C. when methanesulfonyl chloride (0.1 ml) was added, the mixture was kept at 0° C. for a further 30 minutes then brought to room temperature for 1 h. Dilute hydrochloric acid (10 ml, 1 M) and dichloromethane were added, the organic layer separated, dried and evaporated in vacuo to give the product as a brown gum. Purification by column chromatography over silica gel eluting with dichloromethane containing ethyl acetate (0-100%) gave 3-Methoxy-4-methanesulfonylamino-N-(3,4-methylenedioxyphenyl)benzamide (65 mg, 55%) as a white solid.

$^1$H NMR ((CD$_3$)$_2$CO) 9.52 (1 H, bs, NH), 8.13 (1 H, bs, NH), 7.74 (1 H, d, J 2 Hz), 7.72 (1 H, dd, J 2, 8 Hz), 7.64 (1 H, d, J 8 Hz), 7.62 (1 H, d, J 2 Hz), 7.26 (1 H, dd, J 2, 8 Hz), 6.91 (1 H, d, J=8 Hz), 6.09 (2H, s), 4.07 (3H, s) and 3.16 (3H, s).

C) 3-Hydroxy-4-methanesulfonylamino-N-(3,4-dihydroxyphenyl)benzamide (DC0051-S8).

To a stirred suspension of 3-Methoxy-4-methanesulfonylamino-N-(3,4-methylenedioxyphenyl)benzamide (200 mg) in dry CH$_2$Cl$_2$ (20 ml) under nitrogen, was added boron tribromide (0.3 ml) then stirring continued for a further 20 hours. Methanol (50 ml) was added carefully, then the solvent evaporated in vacuo to a volume of 1 ml, this was repeated 2 more times. Purification by column chromatography over silica gel eluting with chloroform containing methanol (10-20%) gave 3-Hydroxy-4-methanesulfonylamino-N-(3,4-dihydroxyphenyl)benzamide (DC51-DB) (65 mg, 34%) as pale brown crystals.

$^1$H NMR (CD$_3$OD) 7.45 ($^1$H, d, J 8 Hz), 7.40 (1 H, d, J 2 Hz), 7.36 (1 H, dd, J 2, 8 Hz), 7.20 ($^1$H, d, J 2 Hz), 6.88 (1 H, dd, J 2, 8 Hz), 6.73 (1 H, d, J 8 Hz) and 2.98 (3H, s).

M/z 337 ((M-H)$^-$, 100%)

Hplc (method 1) 29.2 min.

Example 3

N-(3-methanesulfonylamino-4-hydroxyphenyl)-3,4-dihydroxybenzamide. (DC0051-S6; also referred to as DC-0051-AE)

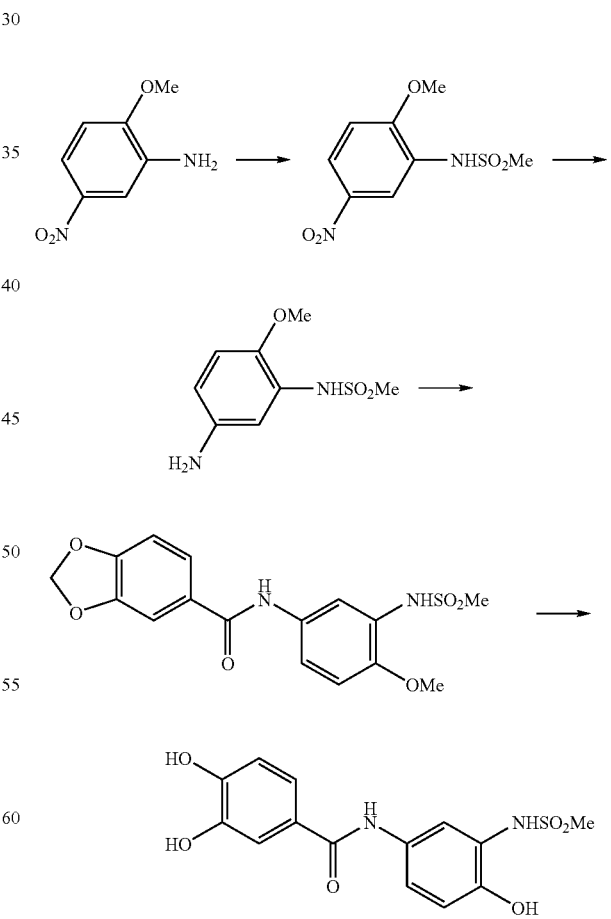

Treatment of commercially available 2-methoxy-5-nitroaniline with methanesulfonyl chloride gave the mesylamine.

Catalytic reduction of the nitro group then gave the required aniline to condense with 3,4-methylenedioxybenzoyl chloride to give the anilide. Removal of the methoxy and methylene dioxy groups with borontribromide then gave N-(3-methanesulfonylamino-4-hydroxyphenyl)-3,4-dihydroxybenzamide (DC0051-S6; also referred to as DC0051-AE).

A) 2-Methoxy-5-nitro-methanesulfonylaminobenzene.

To a solution of 2-methoxy-5-nitroaniline (5 g) in pyridine (25 ml) at 0° C. was added dropwise methanesulfonyl chloride (3.5 ml) then pyridine (0.5 ml). The mixture was left at 0° C. for 1 hour, then brought to room temperature for 2 h. The mixture was poured onto ice (100 g) and dilute hydrochloric acid (3M, 100 ml), the solid formed was filtered then washed with water to give 2-Methoxy-5-nitromethanesulfonylaminobenzene (5.2 9,71%) as an off-white crystalline solid.

¹H NMR (CDCl₃ 8.39 (1 H, d, J 2 Hz), 8.05 (¹H, dd, J 2, 8 Hz), 6.99 (1H, d, J 8 Hz) and 6.98 (1H, bs, NH), B) 2-Methoxy-5-amino-methanesulfonylaminobenzene A solution of 2-Methoxy-5-nitro-methanesulfonylaminobenzene (1 g) in methanol (20 ml) containing palladium on carbon (10%, 100 mg) was stirred at room temperature under hydrogen for 48 h. The mixture was filtered through celite then evaporated to give 2-methoxy-5-aminomethanesulfonylaminobenzene as a brown gum. This was used without purification in the following reaction.

C) N-(3-methanesulfonylamino-4-methoxyphenyl)3,4-methylenedioxybenzamide

A suspension of 3,4-methylenedioxybenzoic acid' (300 mg) in thionyl chloride (10 ml) was heated at reflux for one hour. The solvents were removed in vacuo to give the acid chloride as a white solid. 2-Methoxy-5-aminomethanesulfonylaminobenzene (from the previous reaction) was dissolved in pyridine (20 ml) and added dropwise to the acid chloride. The mixture was left at room temperature for 24 hours, then poured onto ice (50 g) and hydrochloric acid (3M, 100 ml) and the precipitate filtered off and washed with water to give N-(3-methanesulfonylamino-4-methoxyphenyl)-3,4-methylenedioxybenzamide (1.37 g, 93%).

¹H NMR ((CD₃)₂CO) 9.52 (1 H, bs, NH), 7.88 (1 H, dd, J 2, 8 Hz), 7.87 (1 H, d, J 2 Hz), 7.71 (1 H, dd, J 2, 8 Hz). 7.59 (1 H, d, J 2 Hz), 7.14 (1 H, d, J 8 Hz), 7.04 (1 H, d, J 8 Hz), 6.20 (2H, s), 4.00 (3H, s) and 3.10 (3H, s).

D) N-(3-methanesulfonylamino-4-hydroxyphenyl)-3,4-dihydroxybenzamide.

To a stirred suspension of N-(3-methanesulfonylamino-4-methoxyphenyl)-3,4 methylenedioxybenzamide (200 mg) in dry CH₂Cl₂ (20 ml) under nitrogen, was added boron tribromide (0.3 ml) then stirring continued for further 20 hours. Methanol (50 ml) was added carefully, then the solvent evaporated in vacuo to a volume of 1 ml, this was repeated 2 more times. Purification by column chromatography over silica gel eluting with chloroform containing methanol (10-20%) gave N-(3-methanasulfonylamino-4-hydroxyphenyl)-3,4-dihydroxybenzamide (62 mg, 33%) as pale brown crystals.

¹H NMR ((CD₃)₂CO) 7.87 (1 H, d, J 2 Hz), 7.70 (1 H, dd, J 2, 8 Hz), 7.65 (1 H, d, J 2 Hz), 7.05 (1 H, d, J 8 Hz), 7.00 (1 H, d, J 8 Hz) and 3.12 (3H, s).

M/z 337 ((M-H)⁻, 100%)

Hplc (method 1) 22.1 min,

Example 4

N-(3-hydroxy-4-methanesulfonylaminophenyl)-3,4-dihydroxybenzamide (DC-0051-S7; also referred to as DC-0051-AF)

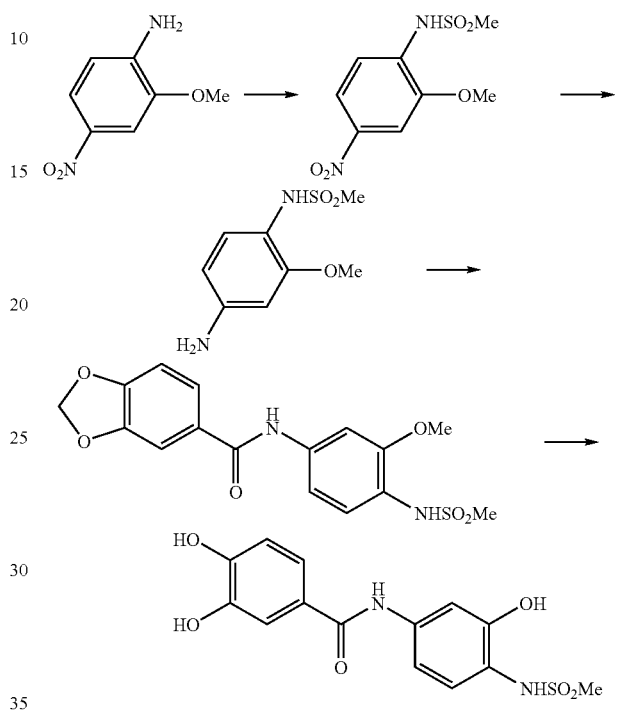

Treatment of commercially available 2-methoxy-4-nitroaniline with methanesulfonyl chloride gave the mesylamine. Reduction by catalytic hydrogenation of the nitro group then gave the required aniline to condense with 3,4-methylenedioxybenzoyl acid chloride to give the anilide. Removal of the methoxy and methylene dioxy groups with borontribromide then gave N-(3-hydroxy-4-methanesulfonylaminophenyl)-3,4-dihydroxybenzamide. (DC-0051-S7; also referred to as DC-0051-AF).

A) 2-Methoxy-4-nitro-methanesulfonylaminobenzene.

To a solution of 2-methoxy-4-nitroaniline (5 g) in pyridine (25 ml) at 0° C. was added dropwise methanesulfonyl chloride (3.5 ml) then pyridine (0.5 ml). The mixture was left at 0° C. for 1 hour, then brought to room temperature for 2 h. The mixture was poured onto ice (100 g) and dilute hydrochloric acid (3M, 100 ml), the solid formed was filtered, then washed with water to give 2-Methoxy-4-nitromethanesulfonylaminobenzene (7.32 g, 98%) as an off-white crystalline solid.

1H NMR (CDCl₃) 7.92 (1 H, dd, J 2, 8 Hz), 7.78 (1H, d, J 2 Hz), 7.64 (1 H, d, J 8 Hz) and 7.23 (¹H, bs, NH).

B) 2-Methoxy-4-aminomethanesulfonylaminobenzene.

A solution of 2-Methoxy-4-nitro-methanesulfonylaminobenzene (1 g) in methanol (20 ml) containing palladium on carbon (10%, 100 mg) was stirred at room temperature under hydrogen for 48 h. The mixture was filtered through celite then evaporated to give 2-methoxy-4-aminomethanesulfonylaminobenzene as a brown gum. This was used without purification in the following reaction.

C) N-(3-methoxy methanesulfonylaminophenyl)-3,4-methylenedioxybenzamide

A suspension of 3,4-methylenedioxybenzoic acid (300 mg) in thionyl chloride (10 ml) was heated at reflux for one hour. The solvents were removed in vacuo to give the acid chloride as a white solid. 2-Methoxy-4-amino-methanesulfonylaminobenzene (from the previous reaction) was dissolved in pyridine (20 ml) and added dropwise to the acid chloride. The mixture was left at room temperature for 24 hours, then poured onto ice (50 g) and hydrochloric acid (3M, 100 ml) and the precipitate filtered off and washed with water to give N-(3-methoxy-4-methanesulfonylaminophenyl)-3,4-methylenedioxybenzamide (1.37 g, 93%).

1H NMR (CDCl$_3$) 7.81 (1 H, d, J 2 Hz), 7.70 (1 H, bs, NH), 7.47 (1 H, d, J 8 Hz), 7.38 ($^1$H dd, J 2, 8 Hz), 7.34 (1 H, d, J 2 Hz), 6.88 (1 H, d, J 8 Hz), 6.79 (1 H, dd, J 2, 8 Hz), 6.63 (1 H, bs, NH), 6.06 (2H, s) 3.92 (3H, s) and 2.91 (3H, s).

D) N-(3-hydroxy-4-methanesulfonylaminophenyl)-3,4-dihydroxybenzamide.

To a stirred suspension of N-(3-methoxy-4-methanesulfonylaminophenyl)-3,4-methylenedioxybenzamide (200 mg) in dry CH$_3$Cl$_2$ (20 ml) under nitrogen, was added boron tribromide (0.3 ml) then stirring continued for a further 20 hours. Methanol (50 ml) was added carefully, then the solvent evaporated in vacuo to a volume of 1 ml, this was repeated 2 more times. Purification by column chromatography over silica gel eluting with chloroform containing methanol (10-20%) gave N-(3-hydroxy-4-methanesulfonylaminophenyl)-3,4-dihydroxybenzamide (62 mg, 33%) as pale brown crystals.

1H NMR ((CD$_3$)$_2$CO) 7.86 (1 H, d, J 2 Hz), 7.60 (1 H, d, J 2 Hz), 7.51 (1 H, dd, J 2, 8 Hz), 7.40 (1 H, d, J 8 Hz), 7.30 (1 H, dd, J 2, 8 Hz), 7.00 (1 H, d. J 8 Hz) and 3.06 (3H, s).

M/z 337 ((M-H)$^-$, 100%)

Hplc (method 1) 29.5 min.

Example 5

3,4-Dimethanesulfonylamino-N-(3,4-dimethanesulfonylaminophenyl)benzamide, (referred to as DC0051-GH)

Acid catalysed formation of the methyl ester of 3,4-diaminobenzoic acid followed by mesylation gave the dimesylaminobenzoate. Basic hydrolysis of the ester then gave the required 3,4-dimethanesulfonylaminobenzoic acid. Mesylation of 4-nitro-1,2-phenylenediamine gave the dimesylamino product which after catalytic hydrogenation gave the required aniline. Condensation of the acid with the amine in the presence of DCC then gave the tetramesylamino-amide.

A) Methyl-3,4-diaminobenzoate

To dry methanol (20 ml) was carefully added thionyl chloride (1 ml) dropwise with stirring. The 3,4-diaminobenzoic acid (1 g) was added in portions at R.T. with stirring then the mixture heated at reflux for 3 h. Saturated sodium bicarbonate was added until the mixture was basic, then the mixture extracted into chloroform containing 25% methanol. The extract was dried and evaporated in vacuo to give the product (0.88 g, 81%) as a brown crystalline solid.

$^1$H NMR (CDCl$_3$) 7.46 (1H, dd, J 2, 8 Hz), 7.40(1H, d, J 2 Hz), 6.67 (1H, d, J 8 Hz) and 3.84 (3H, s).

B) Methyl-3,4-dimethanesulfonylaminobenzoate.

A solution of the diamine (0.88 g) in pyridine (10 ml) at 0° C. was treated with methanesulfonyl chloride (2 ml). The mixture was left at RT for 12 hours, then poured onto ice and hydrochloric acid (3M, 50 ml) and the mixture filtered to give the product as a white crystalline solid (0.54 g, 32%).

$^1$H NMR ((CD$_3$)$_2$SO) 9.39 (2H, bs), 8.11 (1H, d, J 2 Hz), 7.95(1H, dd, J 2, 8 Hz), 7.75 (1H, d, J 8 Hz), 3.97 (3H, s), 3.28 (3H, s) and 3.17 (3H, s).

C) 3,4-Dimethanesulfonylaminobenzoic acid.

A suspension of the ester (0.5 g) in acetone (25 ml) was treated with sodium hydroxide solution (3M, 5 ml) and the resultant orange solution left at R.T. for 2 hours. Aqueous hydrochloric acid (3M) was added until the solution was acidic then extraction into ethyl acetate containing 25% methanol gave the acid as a brown solid (0.36 g, 75%).

$^1$H NMR ((CD$_3$)$_2$SO) 9.30 (2H, bs), 8.10 (1H, d, J 2 Hz), 7.93 (1H, dd, J 2, 8 Hz), 7.72 (1H, d, J 8 Hz), 3.27 (3H, s) and 3.17 (3H, s).

D) 3,4-Dimethanesulfonylamino-nitrobenzene.

A solution of the diamine (2 g) in pyridine (10 ml) at 0° C. was treated with methanesulfonyl chloride (3 ml). The mix-

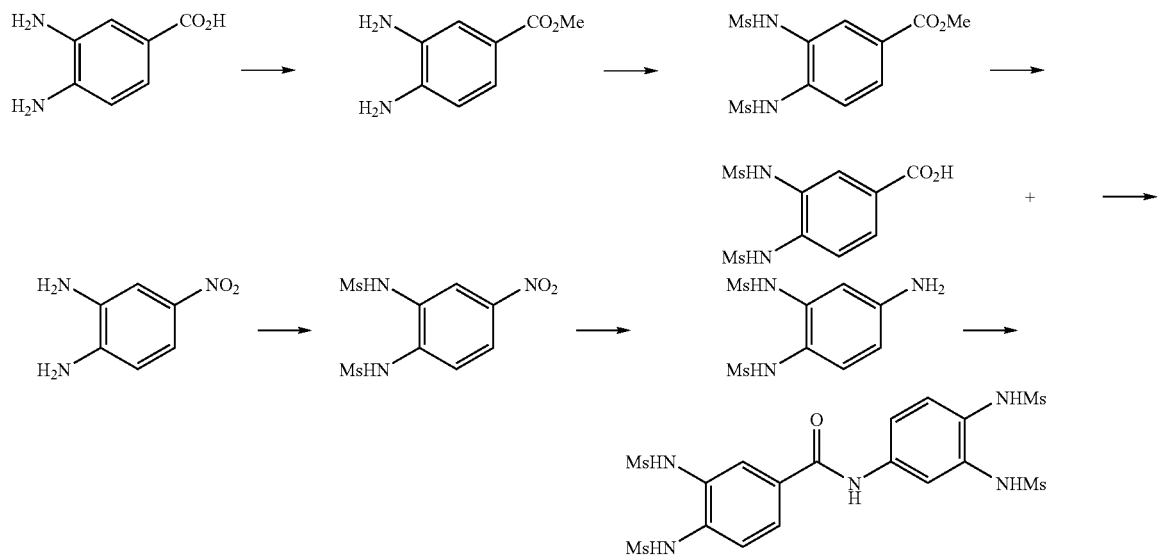

ture was left at RT for 12 hours, then poured onto ice and hydrochloric acid (3M, 50 ml) and the mixture filtered to give the product as a white crystalline solid (1.21 g, 30%).

$^1$H NMR ((CD$_3$)$_2$SO) 8.37 (1H, d, J 2 Hz), 8.24 (1H, dd, J 2, 8 Hz), 7.86 (1H, d, J 8 Hz), 3.34 (3H, s) and 3.24 (3H, s).

E) 3,4-Dimethanesulfonylamino-aniline.

A suspension of 3,4-Dimethanesulfonylamino-nitrobenzene (1.2 g) in methanol (50 ml) and ethyl acetate (50 ml) was stirred under a hydrogen atmosphere with palladium on carbon (10%, 10 mg) for 18 hours. The catalyst was removed by filtration through celite and the solvent removed in vacuo to give the amine (1.0 g) as a brown gum. This was used without further purification.

F) N-(3,4-dimethanesulfonylaminophenyl)-3,4-dimethanesulfonylaminobenzamide (referred to as DC0051-GH)

A suspension of the acid (1.5 g) and the amine (1.5 g) with DCC (1.5 g) in dry THF (100 ml) were stirred together for 12 hours, then the solvent removed in vacuo. Methanol (50 ml) was added to the residue and the white solid filtered. Suspension of the residue in more methanol (50 ml) followed by filtration gave the crude product as the residue as an off-white solid. Suspension of the solid in acetone (4×50 ml), filtration and removal of the solvent in vacuo gave the pure product in the filtrate as a white solid.

$^1$H NMR ((CD$_3$)$_2$CO) 10.03 (1H, bs), 8.45 (2H, bs), 8.28 (1H, d, J 2 Hz), 8.12 (1H, d, J 2 Hz), 8.09 (1H, dd, J 2, 8 Hz), 7.93 (1H, dd, J 2, 8 Hz), 7.85 (1H, d, J 8 Hz), 7.63 (1H, d, J 8 Hz), 3.24 (3H, s), 3.23 (3H, s), 3.19 (3H, s) and 3.17 (3H, s).

hplc 30.3 minutes.

Example 6

4-Hydroxy-3-methanesulfonylamino-N-(3-hydroxy-4-methanesulfonylaminophenyl)benzamide, (referred to as DC0051-CF)

to give the anilide. Reduction by catalytic hydrogenation followed by immediate mesylation gave the mesylamine. This was demethylated by reaction with borontribromide to give 4-Hydroxy-3-methanesulfonylamino-N-(3-hydroxy-4-methanesulfonylaminophenyl)benzamide (DC0051-CF).

A) 2-Methoxy-4-nitro-methanesulfonylaminobenzene.

To a solution of 2-methoxy-4-nitroaniline (5 g) in pyridine (25 ml) at 0° C. was added dropwise methanesulfonyl chloride (3.5 ml). The mixture was left at 0° C. for 1 hour, then brought to RT for 2 h. The mixture was poured onto ice (100 g) and dilute hydrochloric acid (3M, 100 ml), the solid formed was filtered then washed with water and dried to give 2-methoxy-4-nitro-methanesulfonylaminobenzene (7.32 g, 98%) as an off-white crystalline solid.

$^1$H NMR (CDCl$_3$) 7.93 (1H, dd, J 2, 8 Hz), 7.78 (1H, d, J 2 Hz), 7.65 (1H, d, J 8 Hz), 7.23 (1H, bs), 4.00 (3H, s) and 3.09 (3H, s).

B) 2-Methoxy-4-amino-methanesulfonylaminobenzene.

A solution of 2-methoxy-4-nitro-methanesulfonylaminobenzene (1 g) in methanol (20 ml) containing palladium on carbon (10%, 100 mg) was stirred at RT under hydrogen for 48 h. The mixture was filtered through celite then evaporated to give 2-methoxy-4-amino-methanesulfonylaminobenzene as a brown gum. This was used without purification in the following reaction.

C) 4-Methoxy-3-nitro-N-(4-methanesulfonylamino-3-methoxyphenyl)benzamide

A suspension of 4-methoxy-3-nitrobenzoic acid (1 g) in thionyl chloride (20 ml) was heated at reflux for two hours. Excess thionyl chloride removed in vacuo to give the acid chloride as a white solid. The acid chloride was dissolved in dry dichloromethane (25 ml) and added to a mixture of pyridine (1 ml) and 2-methoxy-4-amino-methanesulfonylaminobenzene (0.4 g) in dichloromethane (5 ml) dropwise. The mixture was left at room temperature for 24 hours, then

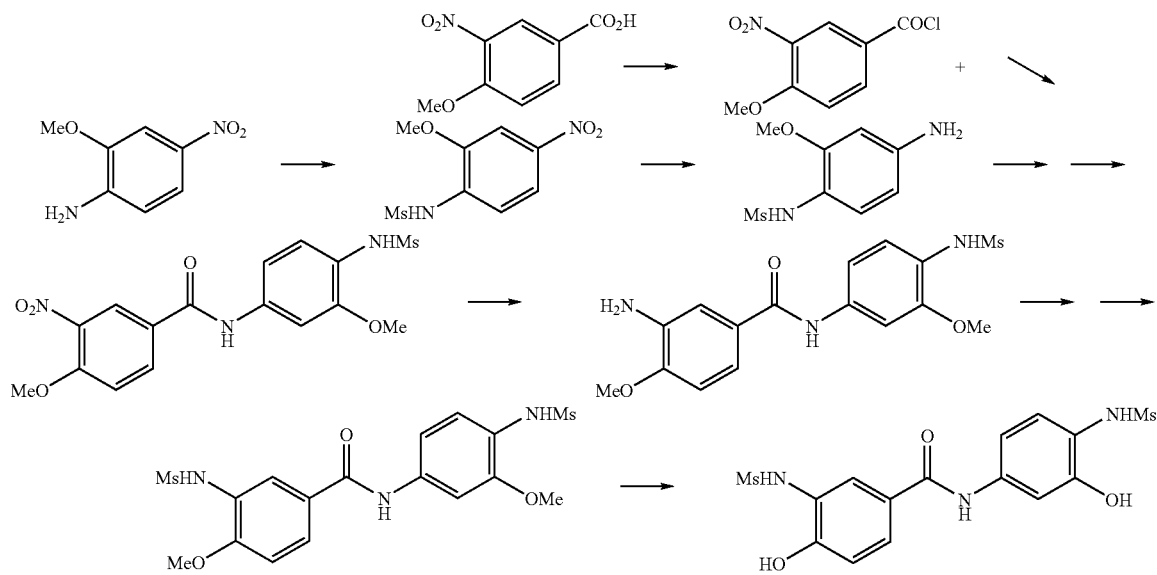

Treatment of commercially available 2-methoxy-4-nitroaniline with methanesulfonyl chloride gave the mesylamine. Catalytic reduction of the nitro group then gave the required aniline to condense with 4-methoxy-3-nitrobenzoyl chloride dichloromethane (50 ml) and hydrochloric acid (1M, 50 ml) added and the precipitate filtered off and washed with water to give 4-methoxy-3-nitro-N-(4-methanesulfonylamino-3-methoxyphenyl)benzamide (0.43 g, 54%).

¹H NMR ((CD₃)₂CO) 8.57 (1H, d, J 2 Hz), 8.41 (1H, dd, J 2, 8 Hz), 7.89 (1H, d, J 2 Hz), 7.61 (1H, d, J 8 Hz), 7.47 (1H, d, J 8 Hz), 7.40 (1H, dd, J 2, 8 Hz), 4.18 (3H, s), 4.02 (3H, s) and 3.03 (3H, s).

D) 4-Methoxy-3-methanesulfonylamino-N-(3-methoxy-4-methanesulfonylaminophenyl)-benzamide A suspension of 4-methoxy-3-nitro-N-(4-methanesulfonylamino-3-methoxyphenyl)benzamide (100 mg) in methanol (20 ml) was stirred under hydrogen with palladium on carbon (10%, 50 mg) for 18 hours. The solvents were removed in vacuo to give a brown gum. The residue was dissolved in pyridine (0.5 ml) and cooled to 0° C. when methanesulfonyl chloride (0.1 ml) was added, the mixture was kept at 0° C. for a further 30 minutes then brought to R.T. for 1 h. Dilute hydrochloric acid (10 ml, 1M) and dichloromethane were added, the organic layer separated, dried and evaporated in vacuo to give the product as a brown gum. Purification by column chromatography over silica gel eluting with dichloromethane containing ethyl acetate (0-100%) gave 3-methanesulfonylamino-4-methoxy-N-(3-methanesulfonylamino-4-methoxyphenyl)benzamide (65 mg, 56%) as a white solid.

¹H NMR ((CD₃)₂CO) 9.61 (1H, bs, NH), 8.11 (1H, d, J 2 Hz), 7.96 (1H, bs, NH), 7.90 (1H, dd, J 2, 8 Hz), 7.85 (1H, d, J 2 Hz), 7.67 (1H, bs, NH), 7.39 (1H, d, J 8 Hz), 7.34 (1H, dd, J 2, 8 Hz), 7.23 (1H, d, J 8 Hz), 4.02 (3H, s), 3.94 (3H, s), 3.04 (3H, s) and 2.95 (3H, s).

E) 4-Hydroxy-3-methanesulfonylamino-N-(3-hydroxy-4-methanesulfonylaminophenyl)-benzamide To a stirred suspension of 3-methanesulfonylamino-4-methoxy-N-(3-methanesulfonylamino-4-methoxyphenyl) benzamide (200 mg) in dry CH₂Cl₂ (20 ml) under nitrogen, was added boron tribromide (0.3 ml) then stirring continued for a further 20 hours. Methanol (50 ml) was added carefully, then the solvent evaporated in vacuo to a volume of 1 ml, this was repeated 2 more times. Purification by column chromatography over silica gel eluting with chloroform containing methanol (10-20%) gave 4-hydroxy-3-methanesulfonylamino-N-(3-hydroxy-4-methanesulfonylaminophenyl)-benzamide (62 mg, 33%) as pale brown crystals.

¹H NMR (CD₃OD) 7.92 (1H, d, J 2 Hz), 7.68 (1H, dd, J 2, 8 Hz), 7.51 (1H, d, J 2 Hz), 7.26 (1H, d, J 8 Hz), 6.99 (1H, dd, J 2, 8 Hz), 6.98 (1H, d, J 8 Hz), 2.99 (3H, s) and 2.92 (3H, s). Hplc (method 1) 29.0 min.

Example 7

3-Hydroxy-4-methanesulfonylamino-N-(4-hydroxy-3-methanesulfonylaminophenyl)benzamide, (referred to as DC0051-DE)

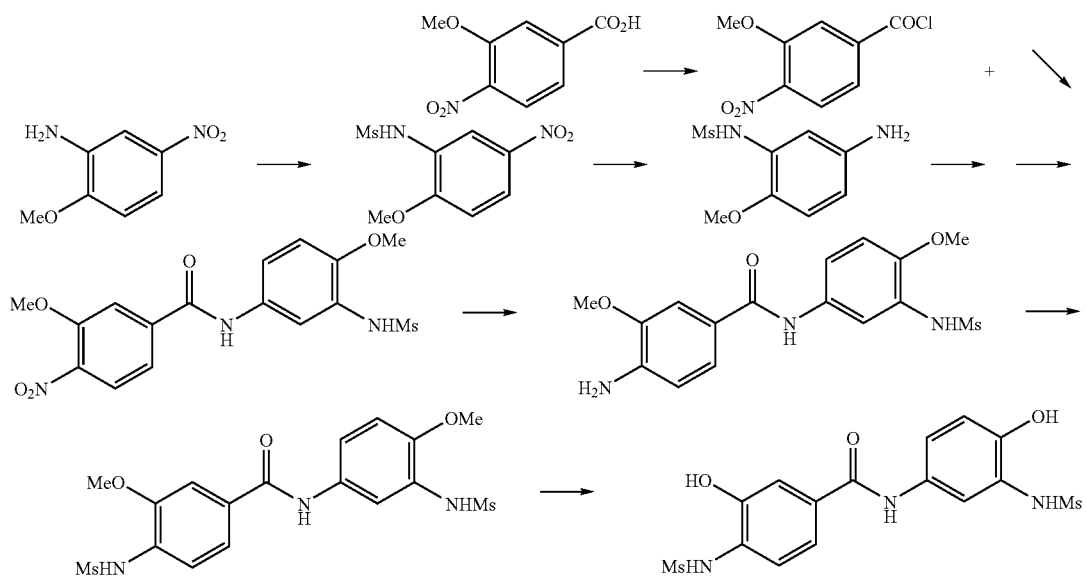

Treatment of commercially available 2-methoxy-5-nitroaniline with methanesulfonyl chloride gave the mesylamine. Catalytic reduction of the nitro group then gave the required aniline to condense with 3-methoxy-4-nitrobenzoyl chloride to give the anilide. Reduction by catalytic hydrogenation followed by immediate mesylation gave the mesylamine. This was demethylated by reaction with borontribromide to give a low yield of 3-Hydroxy-4-methanesulfonylamino-N-(4-hydroxy-3-methanesulfonylaminophenyl)benzamide (DC0051-DE), with a large amount of a stable borate complex.

A) 2-Methoxy-5-nitro-methanesulfonylaminobenzene

To a solution of 2-methoxy-5-nitroaniline (5 g) in pyridine (25 ml) at 0° C. was added dropwise methanesulfonyl chloride (3.5 ml) then pyridine (0.5 ml). The mixture was left at 0° C. for 1 hour, then brought to RT for 2 h. The mixture was poured onto ice (100 g) and dilute hydrochloric acid (3M, 100 ml), the solid formed was filtered then washed with water to give 2-Methoxy-5-nitro-methanesulfonylaminobenzene (5.2 g, 71%) as an off-white crystalline solid.

¹H NMR (CDCl₃) 8.39 (1H, d, J 2 Hz), 8.05 (1H, dd, J 2, 8 Hz), 6.99 (1H, d, J 8 Hz), 6.97 (1H, bs, NH), 4.01 (3H, s) and 3.07 (3H, s).

B) 2-Methoxy-5-amino-methanesulfonylaminobenzene

A solution of 2-Methoxy-5-nitro-methanesulfonylaminobenzene (1 g) in methanol (20 ml) containing palladium on carbon (10%, 100 mg) was stirred at RT under hydrogen for 48 h. The mixture was filtered through celite then evaporated to give 2-methoxy-5-amino-methanesulfonylaminobenzene as a brown gum. This was used without purification in the following reaction.

C) 3-Methoxy-4-nitro-N-(3-methanesulfonylamino-4-methoxyphenyl)benzamide

A suspension of 3-methoxy-4-nitrobenzoic acid (1.5 g) in thionyl chloride (25 ml) was heated at reflux for two hours. Excess thionyl chloride removed in vacuo to give the acid chloride as a white solid. The acid chloride was dissolved in dry dichloromethane (50 ml) then added to a mixture of pyridine (1.5 ml) and 4-methoxy-3-methanesulfonylamino-aniline (1.8 g) in dichloromethane (50 ml) dropwise. The mixture was left at room temperature for 24 hours, then dichloromethane (100 ml) and hydrochloric acid (1M, 100 ml) added and the precipitate filtered off and washed with water to give 3-methoxy-4-nitro-N-(3-methanesulfonylamino-4-methoxyphenyl)benzamide (2.41 g, 80%).

$^1$H NMR (($CD_3$)$_2$CO) 9.88 (1H, bs, NH), 8.03 (1H, d, J 8 Hz), 7.99 (1H, d, J 2 Hz), 7.87 (1H, dd, J 2, 8 Hz), 7.86 (1H, d, J 2 Hz), 7.81 (1H, dd, J 2, 8 Hz), 7.19 (1H, d, J 8 Hz), 4.17 (3H, s), 4.02 (3H, s) and 3.11 (3H, s).

D) 3-Methoxy-4-methanesulfonylamino-N-(3-methanesulfonylamino-4-methoxyphenyl)benzamide A suspension of 3-methoxy-4-nitro-N-(3-methanesulfonylamino-4-methoxyphenyl)benzamide (1.4 g) in methanol (20 ml) was stirred under hydrogen with palladium on carbon (10%, 50 mg) for 18 hours. The solvents were removed in vacuo to give a brown gum. The residue was dissolved in pyridine (5 ml) and cooled to 0° C. when methanesulfonyl chloride (0.5 ml) was added, the mixture was kept at 0° C. for a further 2 hours then brought to R.T. for 1 h. The mixture was poured onto ice (50 g) and hydrochloric acid (3M, 50 g), the resultant brown solid filtered and washed with water to give 4-methanesulfonylamino-3-methoxy-N-(3-methanesulfonylamino-4-methoxyphenyl)benzamide (1.26 g, 86%) as a brown solid.

$^1$H NMR (($CD_3$)$_2$CO) 9.66 (1H, bs, NH), 8.11 (1H, bs, NH), 7.88 (1H, dd, J 2, 8 Hz), 7.87 (1H, d, J 2 Hz), 7.84 (1H, bs, NH), 7.79 (1H, d, J 2 Hz), 7.76 (1H, dd, J 2, 8 Hz), 7.65 (1H, d, J 8 Hz), 7.17 (1H, d, J 8 Hz), 4.08 (3H, s), 4.01 (3H, s), 3.16 (3H, s) and 3.11 (3H, s).

E) 3-Hydroxy-4-methanesulfonylamino-N-(3-methanesulfonylamino-4-hydroxyphenyl)benzamide To a stirred suspension of 4-methanesulfonylamino-3-methoxy-N-(3-methanesulfonylamino-4-methoxyphenyl)benzamide (1.25 g) in dry $CH_2Cl_2$ (50 ml) under nitrogen, was added boron tribromide (1.5 ml) then stirring continued for a further 20 hours. Methanol (50 ml) was added carefully, then the solvent evaporated in vacuo to a volume of 1 ml, this was repeated 2 more times. Purification by column chromatography over silica gel eluting with chloroform containing methanol (10-20%) gave 3-hydroxy-4-methanesulfonylamino-N-(3-methanesulfonylamino-4-hydroxyphenyl)benzamide (143 mg, 15%) as an off-white solid.

$^1$H NMR (($CD_3$)$_2$CO) 9.55 (1H, bs), 8.82 (1H, bs), 7.87 (1H, d, J 2 Hz), 7.73 (1H, dd, J 2, 8 Hz), 7.69 (1H, d, J 2 Hz), 7.64 (1H, dd, J 2, 8 Hz), 7.59 (1H, d, J 8 Hz), 7.04 (1H, d, J=8 Hz), 3.16 (3H, s) and 3.12 (3H, s).

Hplc (method 1) 29.5 min.

Example 8

3-Hydroxy-4-methanesulfonylamino-N-(3-hydroxy-4-methanesulfonylaminophenyl)benzamide, (referred to as DC0051-DF)

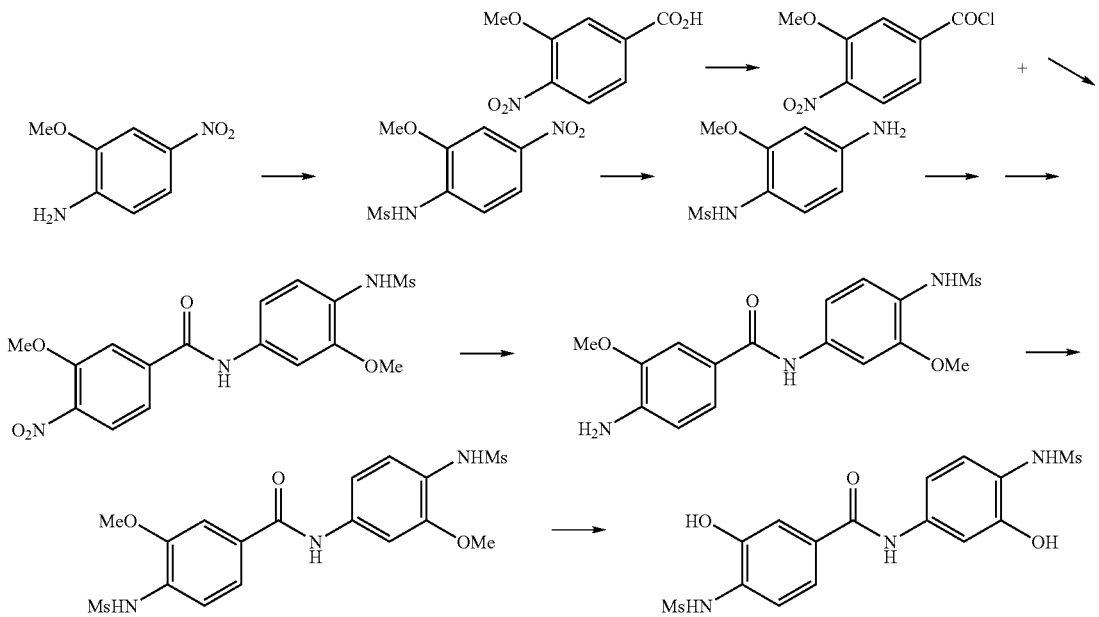

Treatment of commercially available 2-methoxy-4-nitroaniline with methanesulfonyl chloride gave the mesylamine. Catalytic reduction of the nitro group then gave the required aniline to condense with 3-methoxy-4-nitrobenzoyl chloride to give the anilide. Reduction by catalytic hydrogenation followed by immediate mesylation gave the mesylamine. This was demethylated by reaction with borontribromide to give 3-Hydroxy-4-methanesulfonylamino-N-(3-hydroxy-4-methanesulfonylaminophenyl)benzamide (DC0051-DF).

A) 2-Methoxy-4-nitro-methanesulfonylaminobenzene

To a solution of 2-methoxy-4-nitroaniline (5 g) in pyridine (25 ml) at 0° C. was added dropwise methanesulfonyl chloride (3.5 ml). The mixture was left at 0° C. for 1 hour, then brought to RT for 2 h. The mixture was poured onto ice (100 g) and dilute hydrochloric acid (3M, 100 ml), the solid formed was filtered then washed with water and dried to give 2-methoxy-4-nitro-methanesulfonylaminobenzene (7.32 g, 98%) as an off-white crystalline solid.

$^1$H NMR (CDCl$_3$) 7.93 (1H, dd, J 2, 8 Hz), 7.78 (1H, d, J 2 Hz), 7.65 (1H, d, J 8 Hz), 7.23 (1H, bs), 4.00 (3H, s) and 3.09 (3H, s).

B) 2-Methoxy-4-amino-methanesulfonylaminobenzene.

A solution of 2-methoxy-4-nitro-methanesulfonylaminobenzene (1 g) in methanol (20 ml) containing palladium on carbon (10%, 100 mg) was stirred at RT under hydrogen for 48 h. The mixture was filtered through celite then evaporated to give 2-methoxy-4-amino-methanesulfonylaminobenzene as a brown gum. This was used without purification in the following reaction.

C) 3-Methoxy-4-nitro-N-(4-methanesulfonylamino-3-methoxyphenyl)benzamide

A suspension of 3-methoxy-4-nitrobenzoic acid (1.5 g) in thionyl chloride (20 ml) was heated at reflux for two hours. Excess thionyl chloride removed in vacuo to give the acid chloride as a white solid. A solution of the acid chloride (1.64 g) in dichloromethane (50 ml) was added to a suspension of 4-mesylamino-3-methoxyaniline (1.75 g) in dichloromethane (50 ml) and then pyridine (1.5 ml) was added. The mixture was refluxed together for 2 hours, then left at RT overnight. The resultant mixture was added to dichloromethane (100 ml) and hydrochloric acid (3M, 50 ml), the resultant precipitate was filtered off, washed with water (100 ml) then dried to give 3-Methoxy-4-nitro-N-(4-methanesulfonylamino-3-methoxyphenyl)benzamide (2.03 g, 67%).

$^1$H NMR ((CD$_3$)$_2$CO) 9.91 (1H, bs, NH), 8.05 (1H, d, J 8 Hz), 7.98 (1H, d, J 2 Hz), 7.90 (1H, d, J 2 Hz), 7.81 (1H, bs, NH), 7.80 (1H, dd, J 2, 8 Hz), 7.50 (1H, d, J 8 Hz), 7.39 (1H, dd, J 2, 8 Hz), 4.18 (3H, s), 4.02 (3H, s) and 3.04 (3H, s).

D) 4-Methanesulfonylamino-3-methoxy-N-(4-methanesulfonylamino-3-methoxyphenyl)benzamide.

A suspension of 3-methoxy-4-nitro-N-(4-methanesulfonylamino-3-methoxyphenyl)benzamide (2.03 g) in methanol (50 ml) and ethyl acetate (50 ml) was stirred under hydrogen with palladium on carbon (10%, 50 mg) for 18 hours. The solvents were removed in vacuo to give a brown gum. The residue was dissolved in pyridine (5 ml) and cooled to 0° C. when methanesulfonyl chloride (1 ml) was added, the mixture was kept at 0° C. for a further 2 hours then brought to R.T. for 1 h. The mixture was poured onto ice (50 g) and hydrochloric acid (3M, 50 g), the resultant brown solid filtered and washed with water to give 4-methanesulfonylamino-3-methoxy-N-(4-methanesulfonylamino-3-methoxyphenyl)benzamide (2.1 g, 100%) as a pale brown solid.

$^1$H NMR ((CD$_3$)$_2$CO) 9.69 (1H, bs, NH), 8.15 (1H, bs, NH), 7.93 (1H, d, J 2 Hz), 7.78 (1H, d, J 2 Hz), 7.76 (1H, bs, NH), 7.74 (1H, dd, J 2, 8 Hz), 7.66 (1H, d, J 8 Hz), 7.47 (1H, d, J 8 Hz), 7.40 (1H, dd, J 2, 8 Hz), 4.09 (3H, s), 4.02 (3H, s), 3.17 (3H, s) and 3.03 (3H, s).

E) 4-Methanesulfonylamino-3-hydroxy-N-(4-methanesulfonylamino-3-hydroxyphenyl)benzamide To a stirred suspension of 4-methanesulfonylamino-3-methoxy-N-(3-methanesulfonylamino-4-methoxyphenyl) benzamide (2 g) in dry CH$_2$Cl$_2$ (50 ml) under nitrogen, was added boron tribromide (2 ml) and the resultant orange suspension left for 3 hours. Methanol (50 ml) was added carefully and the solution stood overnight. The solvent was evaporated in vacuo to a volume of 1 ml, then methanol (50 ml) added, this was repeated 2 more times. Purification by column chromatography over silica gel eluting with chloroform containing methanol (10-20%) gave 4-methanesulfonylamino-3-hydroxy-N-(4-methane sulfonylamino-3-hydroxyphenyl) benzamide (DC0051-DF) (0.74 g, 40%) as a pale brown gum.

$^1$H NMR ((CD$_3$)$_2$SO) 10.37 (1H, bs, NH), 10.21 (1H, bs, NH), 10.01 (1H, bs, NH), 9.05 (1H, bs, OH), 8.76 (1H, bs, OH), 7.68 (1H, bs), 7.53 (1H, bs), 7.51 (1H, dd, J 2, 8 Hz), 7.45 (1H, d, J 8 Hz), 7.21 (2H, bs), 3.14 (3H, s) and 3.03 (3H, s).

Hplc (method 1) 29.4 min.

Example 9

2-Oxo-N-(2-oxo-2,3-dihydro-1H-benzo[d]imidazol-5-yl)-2,3-dihydro-1H-benzo[d]imidazole-5-carboxide (referred to as DC-0051-B1)

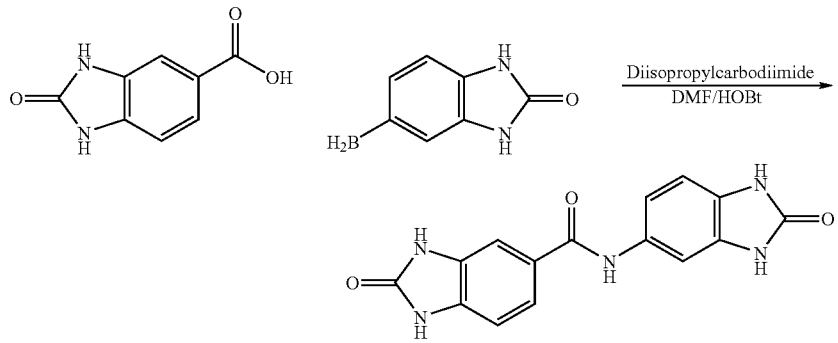

The amide was synthesized by reacting 2-oxo-2,3-dihydro-1H-benzoimidazolyl-5-carboxylic acid with 5-amino-2,3-dihydro-1H-benzoimidazol-5-one in the presence of 1,3-N,N-diisopropylcarbodiimide and 1-hydroxybenzotriazole.

1,3-N,N-Diisopropylcarbodiimde (0.504 g; 4 mmol) was added to a solution of 2-oxo-2,3-dihydro-1H-benzoimidazole-5-carboxylic acid (0.448 g; 2.5 mmol), 5-amino-2-oxo-2,3-dihydro-1H-benzoimidazole and 1-hydroxybenzotriazole (0.34 g; 2.5 mmol) in anhydrous N,N-dimethylformamide (10 ml). The reaction mixture was stirred at 40° C. for 12 hours. The precipitated product was isolated by filtration of the reaction mixture followed by washing three more times with N,N-dimethylformamide (3 ml). The product was dissolved in dimethylsulfoxide (5 ml) and precipitated by diluting the solution with acetonitrile (60 ml). Filtration and drying under vacuum gave 2-Oxo-N-(2-oxo-2,3-dihydro-1H-benzo[d]imidazol-5-yl)-2,3-dihydro-1H-benzo[d]imidazole-5-carboxide (also referred to as DC-0051-B1) (0.22 g; 28%).

$^1$H NMR ((CD3)$_2$SO 10.62 (1H, s, NH), 10.53 (1H, s, NH), 9.98 (1H, s, NH) 7.65 (1H, d, J 8 Hz) 7.55 (2H, bs) 7.23 (1H, d, J 8 Hz) 7.05 (1H, d, J 8 Hz) 7.85 (1H, d, J 8 Hz).

Example 10

N-(3,4-dihydroxyphenyl)-2-oxo-2,3-dihydro-1H-benzo[d]imidazole-5-carboxamide (referred to as DC-0051-B2)

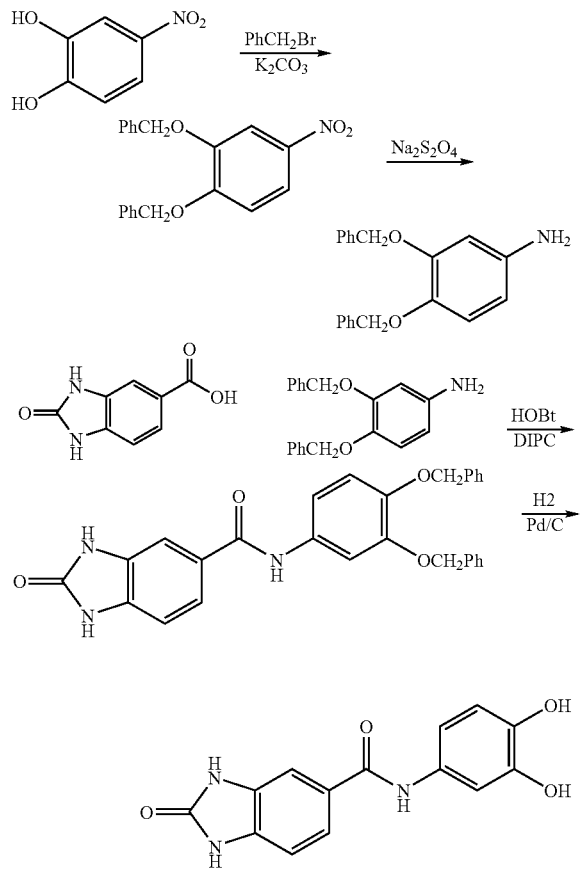

3,4-Dihydroxy-1-nitrobenzene was benzylated by refluxing with benzyl bromide with potassium carbonate as a base in acetone which on reduction with sodium dithionite gave 3,4-dibenzyloxy aniline. This was coupled to 2-oxo-2,3-dihydro-1H-benzoimidazole-5-carboxylic acid using N,N-1,3-diisopropylcarbodiimide in the presence of 1-hydroxybenzotriazole to provide the amide. The amide was then debenzylated by hydrogenation in presence of palladium on carbon.

A) 3,4-Dibenzyloxy-1-nitro benzene

Potassium carbonate (4.14 g; 30 mmol) was added to a solution of 3,4-dihydroxy-1-nitrobenzene (1.55 g; 10 mmol) and benzyl bromide (3.42 g; 20 mmol) in acetone (100 ml). The reaction mixture was refluxed for 12 hours. After the removal of the solvent under reduced pressure, the residue was partitioned between ethyl acetate (150 ml) and water (50 ml). The ethyl acetate layer was washed with water (100 ml) and dried over anhydrous magnesium sulfate. Removal of the solvent under reduced pressure provided 2.37 g of 3,4-Dibenzyloxy-1-nitro benzene. (Yield=70%)

$^1$H NMR CDCl$_3$ 7.85 (1H, d, J 8 Hz) 7.8 (1H, s) 7.28-7.50 (m, 10H) 6.95 (1H, d, J 8 Hz) 5.24 (s, 2H) 5.21 (s, 2H)

B) 3,4-Dibenzyloxy aniline

Sodium dithionite (2 g) was added to a solution of 3,4-Dibenzyloxy-1-nitro benzene (2.37 gm) in a mixture of methanol (30 ml)/aqueous ammonia (5 ml). After stirring for 12 hrs at room temperature, the solvent was removed under reduced pressure. The residue was partitioned between ethyl acetate (75 ml) and water (75 ml). The ethyl acetate layer was washed with water (25 ml), brine solution (25 ml), dried over anhydrous magnesium sulfate and concentrated under reduced pressure. Purification by flash chromatography over silica gel eluting with ethyl acetate/hexane (1:1) provided 1.0 g of 1-Benzyloxy-2-methoxy-5-aminobenzene (Yield=47%).

$^1$H NMR CDCl$_3$ 7.27-7.47 (10H, m) 6.8 (1H, d, J 8 Hz) 6.37 (1H, s) 6.22 (1H, d, J 8 Hz) 5.13 (2H, s) 5.06 (2H, s) 3.49 (2H, bs, NH$_2$)

C) 2-Oxo-2,3-dihydro-1H-benzoimidazolyl-5-carboxyl (1-N-3,4-dibenzyloxy phenyl)amide 1,3-N,N-Diisopropylcarbodiimde (0.412 g; 3.27 mmol) was added to a solution of 2-oxo-2,3-dihydro-1H-benzoimidazole-5-carboxylic acid (0.584 g; 3.27 mmol) 3,4-dibenzyloxy aniline (1.0 g, 3.27 mmol) and 1-hydroxybenzotriazole (0.442 g, 3.27 mmol) in anhydrous N,N-dimethylformamide (15 ml). After stirring for 16 hrs at room temperature the reaction mixture was poured in water (150 ml). The pH of the mixture was adjusted to 2 with 1N hydrochloric acid and stirred for 30 minutes. Filtration and washing the product with ethyl acetate (3×10 ml) provided 1.12 grams of 2-Oxo-2,3-dihydro-1H-benzoimidazolyl-5-carboxyl(1-N-3,4-dibenzyloxy phenyl)amide.

Yield=73.6%.

$^1$H NMR (CD$_3$)$_2$SO 10.5 (1H, s, NH) 7.65 (1H, d, J 8 Hz) 7.6 (1H, s) 7.2-7.6 (m, 12H) 7.0 (2H, d, J 8 Hz) 5.15 (4H, s).

D) N-(3,4-dihydroxyphenyl)-2-oxo-2,3-dihydro-1H-benzo[d]imidazole-5-carboxamide

A solution of 2-Oxo-2,3-dihydro-1H-benzoimidazolyl-5-carboxyl(1-N-3,4-dibenzyloxy phenyl)amide. (1.10 g) in a mixture of acetic acid (100 ml) and N,N-dimethylformamide (25 ml) was hydrogenated at 40 Psi in presence of 10% palladium on carbon for 12 hrs at room temperature. After removal of the catalyst by filtration, the solvent was removed under reduced pressure. The residue was dissolved in N,N-dimethylformamide (15 ml) and the product was precipitated by diluting with a mixture of hexane/ethyl acetate (1:1) (100 ml). Filtration provided 0.550 g of N-(3,4-dihydroxyphenyl)-2-oxo-2,3-dihydro-1H-benzo[d]imidazole-5-carboxamide. Yield=81%.

$^1$H NMR (CD$_3$)$_2$SO 10.94 (1H, bs) 9.86 (1H, s) 8.85 (1H, bs) 7.61 (1H, d J 8 Hz) 7.59(1H, s) 7.3 (1H, s) 7.0 (1H, d, J 8 Hz) 6.96 (1H, d, J 8 Hz) 6.66 (1H, d, J 8 Hz)

M/z (286 (M+H$^+$), 308 (M+Na$^+$ 100%). HPLC (method 2) 3.256 min.

Example 11

3,4-dihydroxy-N-(2-oxo-2,3-dihydro-1H-benzo[d]imidazol-5-yl)benzamide (referred to as DC-0051-B3)

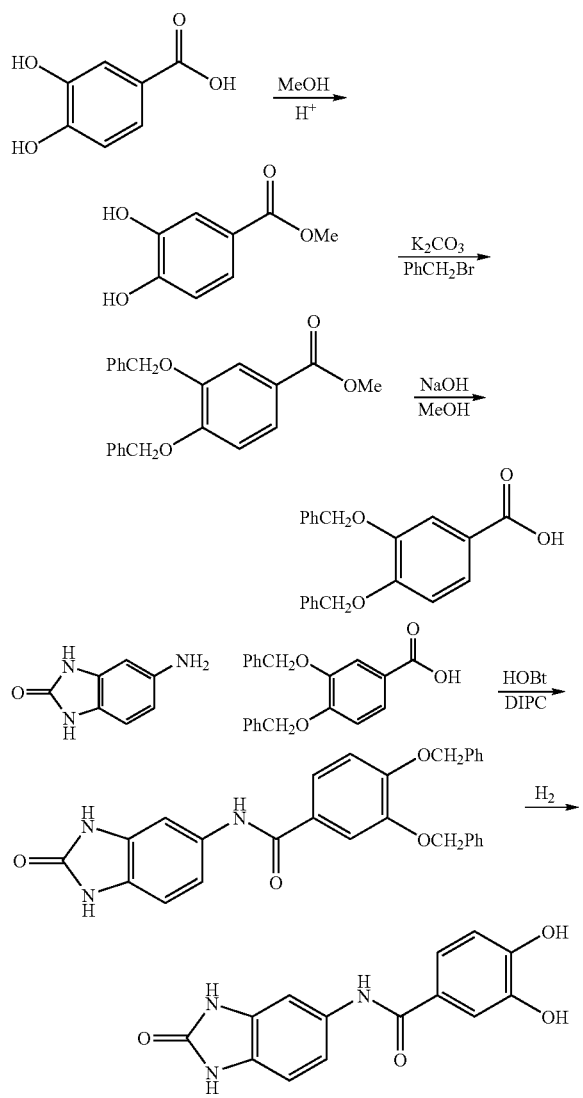

3,4-Dihydroxybenzoic acid was converted to its methyl ester by refluxing in methanol in presence of acid. The dihydroxy group was protected as its benzyl ether by treating with benzyl bromide and potassium carbonate. Hydrolysis of the ester using sodium hydroxide provided the acid which was coupled to 5-amino-2,3-dihydro-1H-benzoimidazol-5-one using N,N-1,3-diisopropylcarbodiimide in presence of 1-hydroxybenzotriazole to provide the amide. The amide was debenzylated by hydrogenation in presence of palladium on carbon.

A) 3,4-Dihydroxy benzoic acid methyl ester

A solution of 3,4-dihydroxy benzoic acid (2.8 g) in methanol (150 ml) was refluxed in presence of concentrated hydrochloric acid (0.5 ml) for 12 hrs. After concentrating under reduced pressure, the residue was dissolved in ethyl acetate (150 ml) and washed with water (50 ml) 10% sodium bicarbonate solution (50 ml), brine solution (50 ml) and dried over anhydrous magnesium sulfate. Removal of the solvent under reduced pressure provided 2.64 g of 3,4-dihydroxybenzoic acid methyl ester. (Yield 86.5%).

$^1$H NMR CDCl$_3$ 7.7 (1H, s) 7.63 (1H, d, J 8 Hz) 6.92 (1H, d, J 8 Hz) 5.7(2H, bs) 3.92 (3H, s)

B) 3,4-Dibenzyloxy benzoic acid methyl ester

Potassium carbonate (6.5 g; 47 mmol) was added to a solution of 3,4-dihydroxybenzoic acid methyl ester (2.6 g; 15.7 mmol) and benzyl bromide (5.37 g; 31.4 mmol) in acetone (100 ml). The reaction mixture was refluxed for 12 hrs. After the removal of the solvent under reduced pressure, the residue was partitioned between ethyl acetate (150 ml) and water (50 ml). The ethyl acetate layer was washed with water (50 ml) and dried over anhydrous magnesium sulfate. Removal of the solvent under reduced pressure provided 3.36 g of 3,4-Dibenzyloxy benzoic acid methyl ester (Yield=86.6%)

$^1$H NMR CDCl$_3$ 7.67 (1H, s) 7.65 (1H, d, J 8 Hz) 7.28-7.50 (m, 10H) 6.95 (1H, d, J 8 Hz) 5.24 (s, 2H) 5.21 (s, 2H) 3.89 (s, 3H)

C) 3,4-Dibenzyloxy benzoic acid

A solution of sodium hydroxide (1.2 g) in methanol (100 ml) was added to a solution of 3,4-dibenzyloxy benzoic acid methyl ester (4.64 g) in methanol (50 ml) and refluxed for 4 hrs. After removal of methanol under reduced pressure the residue was dissolved in water (100 ml) and washed with ethyl acetate (2×50 ml). The aqueous layer was acidified with 2N hydrochloric acid to pH 2. The precipitated product was collected by filtration which on drying under vacuum provided 2.4 g of 3,4-benzyloxy benzoic acid. (Yield=74%)

$^1$H NMR CDCl$_3$ 7.7 (2H, b, s) 7.27-7.5 (10H, m) 6.98 (1H, d, J 8 Hz) 5.26 (2H, s) 5.22 (2H, s)

D) 3,4-Dibenzyloxy-(5-N-2-oxo-2,3-dihydro-1H-benzoimidazolyl)benzamide.

1,3-N,N-Diisopropylcarbodiimde (0.945 g; 7.5 mmol) was added to a solution of 3,4-dibenzyloxy benzoic acid (1.67 g, 5 mmol), 5-amino-2,3-dihydro-1H-benzoimidazol-5-one (0.745 g, 5 mmol) and 1-hydroxybenzotriazole (0.675 g, 5 mmol) in anhydrous N,N-dimethylformamide (20 ml). After stirring for 16 hrs at room temperature the reaction mixture was poured in water (100 ml). The pH of the mixture was adjusted to 2 with 1N hydrochloric acid and stirred for 30 minutes. Filtration and washing the product with ethyl acetate (3×10 ml) provided 1.06 grams of 3,4-dibenzyloxy-(5-N-2-oxo-2,3-dihydro-1H-benzoimidazolyl)benzamide. (Yield=45.7%).

$^1$H NMR (CD$_3$)$_2$SO 9.94 (1H, s) 7.65-7.2 (14H, m) 7.09 (2H, d, J 8 Hz) 5.1 (4H, s).

E) 3,4-dihydroxy-N-(2-oxo-2,3-dihydro-1H-benzo[d]imidazol-5-yl)benzamide

A solution of 3,4-dibenzyloxy-(5-N-2-oxo-2,3-dihydro-1H-benzoimidazolyl) benzamide (1.06 g; 2.28 mmol) in acetic acid (120 ml) was hydrogenated at 40 Psi in presence of 10% palladium on carbon for 12 hrs at room temperature. After removal of the catalyst by filtration, the solvent was removed under reduced pressure. The residue was dissolved in N,N-dimethylformamide (15 ml) and the product was precipitated by diluting with a mixture of hexane/ethyl acetate (1:1) (100 ml). Filtration provided 0.334 g of 3,4-dihydroxy-N-(2-oxo-2,3-dihydro-1H-benzo[d]imidazol-5-yl)benzamide. Yield=50%.

$^1$H NMR (CD$_3$)$_2$SO 10.54 (1H, bs) 9.78 (1H, s) 9.41 (1H, bs) 7.54 (1H, s) 7.37 (1H, s) 7.32 (1H, d, J 8 Hz) 7.23 (1H, d, J 8 Hz) 6.85 (1H, d, J 8 Hz) 6.80 (1H, d, J 8 Hz).

M/z (286 (M+H$^+$) 100%, 308 (M+Na$^+$). HPLC (method 2) 2.34 min.

Example 12

3-hydroxy-N-(3-hydroxy-4-methoxyphenyl)-4-methoxybenzamide (referred to as DC-0051-B4)

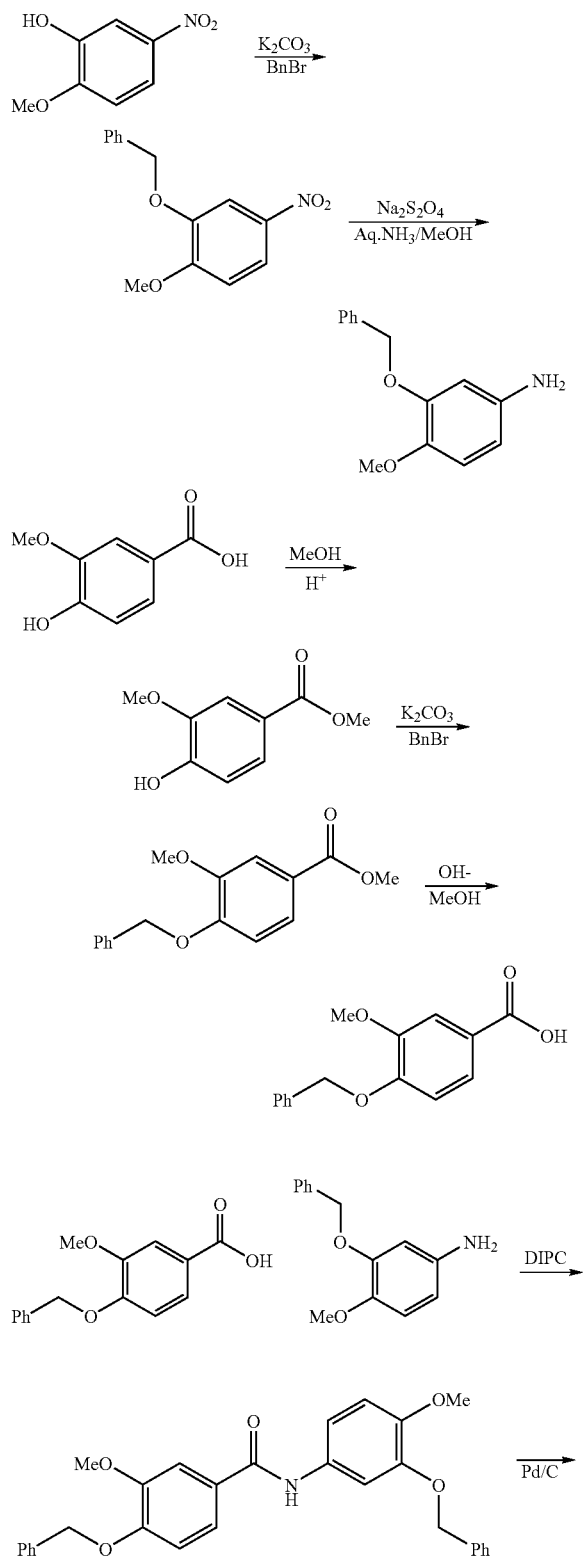

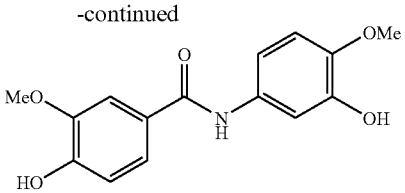

3-Hydroxy-4-methoxy-1-nitrobenzene was benzylated by refluxing with benzyl bromide with potassium carbonate as a base in acetone which on reduction with sodium dithionite gave 3-benzyloxy-4-methoxy aniline. 4-Hydroxy-3-methoxy benzoic acid was converted to its methyl ester by refluxing in methanol in presence of an acid. The hydroxyl was benzylated using benzyl bromide and potassium carbonate. The ester was hydrolyzed with sodium hydroxide to provide the acid. The aniline and acid were coupled using N,N-1,3-diisopropylcarbodiimide in presence of 1-hydroxybenzotriazole to provide the amide. Finally the benzyl group was removed by hydrogenation in presence of palladium on carbon.

A) 1-Benzyloxy-2-methoxy-5-nitrobenzene

Potassium carbonate (1.65 gm; 12 mmol) was added to a solution of 2-methoxy-5-nitro phenol (1.69 g; 10 mmol) and benzyl bromide (1.71 gm; 10 mmol) in acetone (60 ml). The reaction mixture was refluxed for 12 hours. The solvent was removed under reduced pressure and the residue was partitioned between ethyl acetate (150 ml) and water (50 ml). The ethyl acetate layer was separated, washed with water (2×50 ml), dried over anhydrous magnesium sulfate. Removal of the solvent under reduced pressure provided 2.5 g of 1-Benzyloxy-2-methoxy-5-nitrobenzene (Yield=96.5%)

$^1$H NMR CDCl$_3$ 7.95 (1H, d, J 8 Hz) 7.81 (1H, s) 7.3-7.5 (5H, m) 6.92 (1H, d, J 8 Hz) 5.15 (2H, s) 3.95 (3H, s).

B) 1-Benzyloxy-2-methoxy-5-aminobenzene

Sodium dithionite (1.5 g) was added to a solution of 1-benzyloxy-2-methoxy-5-nitrobenzene (2.5 gm) in a mixture of methanol (20 ml)/aqueous ammonia (4 ml). After stirring for 12 hrs at room temperature, the solvent was removed under reduced pressure. The residue was partitioned between ethyl acetate (75 ml) and water (50 ml). The ethyl acetate layer was washed with water (25 ml), brine solution (25 ml), dried over anhydrous magnesium sulfate and concentrated under reduced pressure. Purification by flash chromatography over silica gel eluting with ethyl acetate/hexane (1:1) provided 0.771 g of 1-Benzyloxy-2-methoxy-5-aminobenzene (Yield=35%).

$^1$H NMR CDCl$_3$ 7.25-7.5 (5H, m) 6.78 (1H, d, J 8 Hz) 6.35 (1H, s) 6.28 (1H, d, J 8 Hz) 5.1 (2H, s) 3.8 (3H, s)

C) 4-Hydroxy-3-methoxy benzoic acid methyl ester

A solution of 4-hydroxy-3methoxy benzoic acid (7.2 g) in methanol (150 ml) was refluxed in presence of concentrated hydrochloric acid (0.5 ml) for 12 hrs. After concentrating under reduced pressure, the residue was dissolved in ethyl acetate (200 ml) and washed with water (50 ml) 10% sodium bicarbonate solution (2×50 ml), water (50 ml) and dried over anhydrous magnesium sulfate. Removal of the solvent under reduced pressure provided 7.25 g of 4-hydroxy-3-methoxy benzoic acid methyl ester. (Yield=91.5%).

$^1$H NMR CDCl$_3$ 7.65 (1H, d, J 8 Hz) 7.55 (1H, s) 6.95 (1H, d, J 8 Hz) 6.15 (1H, bs, —OH) 3.95 (3H, s) 3.9 (3H, s).

D) 4-Benzyloxy-3-methoxy benzoic acid methyl ester

Potassium carbonate (3.45 g; 25 mmol) was added to a solution of 4-hydroxy-3-methoxy benzoic acid methyl ester (3.6 g; 20 mmol) and benzyl bromide (3.42 g; 20 mmol) in acetone (100 ml). The reaction mixture was refluxed for 12 hrs. After the removal of the solvent under reduced pressure, the residue was partitioned between ethyl acetate (150 ml) and water (50 ml). The ethyl acetate layer was washed with water (50 ml) and dried over anhydrous magnesium sulfate. Removal of the solvent under reduced pressure provided 4.64 g of 4-benzyloxy-3-methoxy benzoic acid methyl ester (Yield=86.6%)

E) 4-Benzyloxy-3-methoxy benzoic acid

A solution of sodium hydroxide (2.0 g) in methanol (50 ml) was added to a solution of 4-benzyloxy-3-methoxy benzoic acid methyl ester (4.64 g) in methanol (50 ml) and refluxed for 4 hrs. After removal of methanol under reduced pressure the residue was dissolved in water (150 ml) and washed with ethyl acetate (2×50 ml). The aqueous layer was acidified with 2N hydrochloric acid to pH 2. The precipitated product was collected by filtration which on drying under vacuum provided 4.17 g of 4-benzyloxy-3-methoxy benzoic acid. (Yield=74%)

$^1$H NMR CDCl$_3$ 7.7 (1H, d, J 8 Hz) 7.63 (1H, s) 7.3-7.5 (5H, m) 6.92 (1H, d, J 8 Hz) 5.25 (2H, s) 3.98 (3H, s)

F) 4-Benzyloxy-3-methoxy-N-(3-benzyloxy-4-methoxyphenyl)benzamide

N,N-1,3-Diisopropyl carbodiimide (0.40 g, 3.36 mmol) was added to a solution of 1-benzyloxy-2-methoxy-5-aminobenzene (0.771 g, 3.36 mmol), 4-benzyloxy-3-methoxy benzoic acid (0.87 g, 3.36 mmol) and 1-hydroxybenzotriazole (0.454 g, 3.36 mmol) in N,N-dimethylformamide (15 ml) and stirred for 12 hrs. The product was precipitated by diluting with a mixture of ethyl acetate/hexane (1:1) (120 ml). Filtration of the reaction mixture provided 1.12 g of 4-Benzyloxy-3-methoxy-N-(3-benzyloxy-4-methoxyphenyl)benzamide. Yield 69%.

$^1$H NMR (CD$_3$)$_2$SO 9.93 (1H, s) 7.29-7.59 (14H, m) 7.16 (1H, d, J 8 Hz) 6.96 (1H, d, J=8 Hz) 5.18 (2H, s) 5.06 (2H, s) 3.85 (3H, s) 3.76 (3H, s)

G) 3-hydroxy-N-(3-hydroxy-4-methoxyphenyl)-4-methoxybenzamide

A solution of the 4-Benzyloxy-3-methoxy-N-(3-benzyloxy-4-methoxyphenyl)benzamide (1.05 g) in a mixture of N,N-dimethylformamide/methanol (1:5, 120 ml) was hydrogenated in presence of 10% palladium on carbon at 40 Psi at room temperature for 12 hrs. Removal of the catalyst by filtration and purification by flash chromatography over silica gel eluting with 65% ethyl acetate/hexane provided 0.26 g of 3-hydroxy-N-(3-hydroxy-4-methoxyphenyl)-4-methoxybenzamide. Yield=41.6%

$^1$H NMR (CD$_3$)$_2$SO 9.73 (1H, s) 9.62 (1H, bs) 8.99 (1H, bs) 7.5 (1H, s) 7.45 (1H, d, J 8 Hz) 7.29 (1H, s) 7.09 (1H, d, J 8 Hz) 6.85 (1H, d, J 8 Hz) 3.84 (3H, s) 3.74 (3H, s)

M/z (290 (M+H$^+$), 312 (M+Na$^+$), 100%). HPLC (method 2) 3.86 min.

Example 13

The following compounds were prepared using procedures similar those described herein:

i) DC-0051-A2 also referred as DC-0051-S2

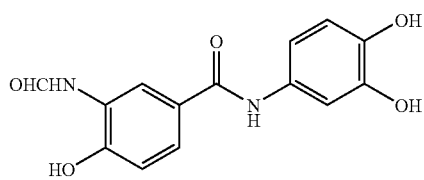

ii) DC-0051-A3 also referred as DC-0051-S3

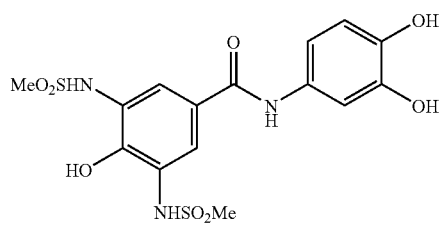

iii) DC-0051-A4 also referred as DC-0051-S4

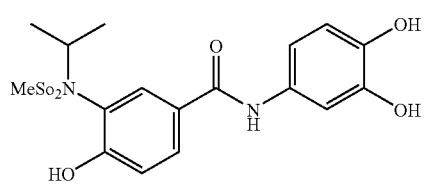

iv) DC-0051-A5 also referred as DC-0051-S5

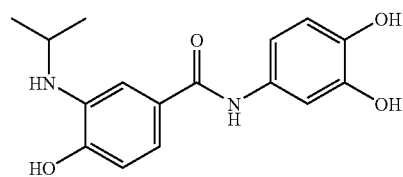

v)

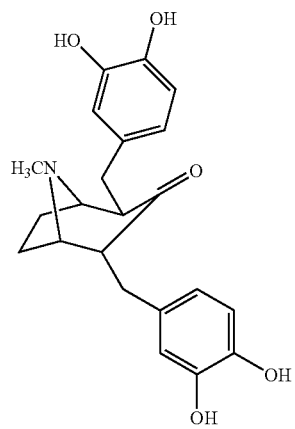

2,4-bis(3,4-dihydroxybenzyl)-8-methyl-8-aza-bicyclo[3.2.1]octan-3-one

-continued vi)
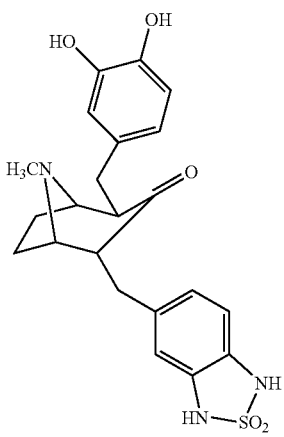

vii)
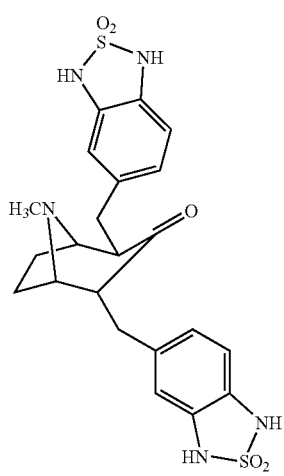

viii)
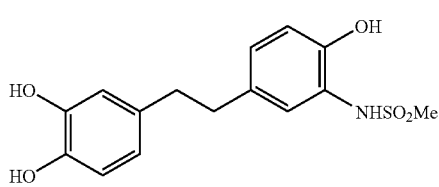

ix)
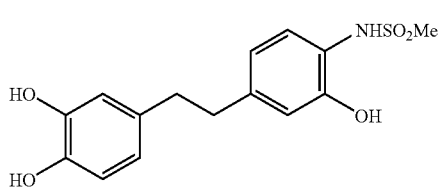

x)
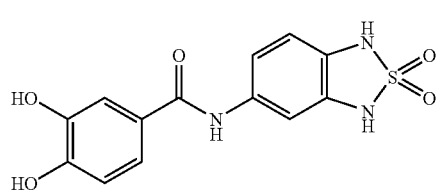

-continued xi)
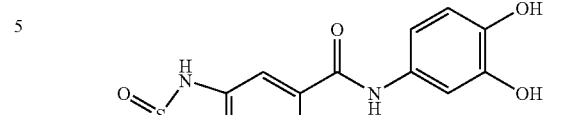

xii)
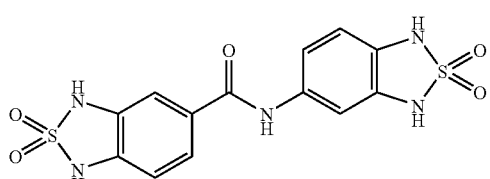

xiii)
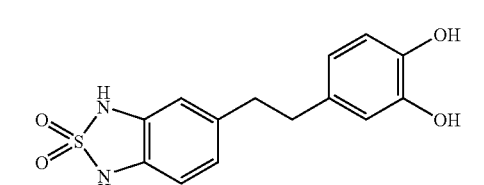

xiv)
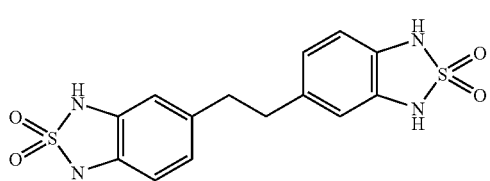

xv)
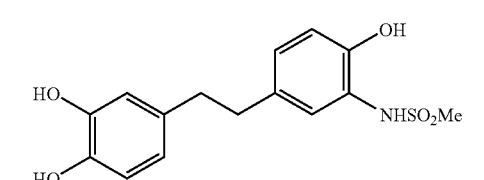

xvi)
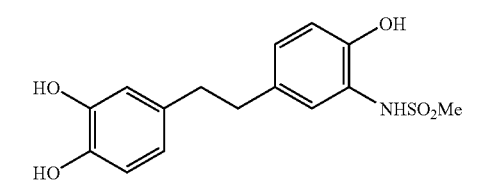

Example 14

4-Hydoxy-3-methanesulfonylamino-N-(4-hydroxy-3-methanesulfonylaminophenyl)-benzamide borate complex (referred to as DC0051-CE borate complex)

Treatment of commercially available 2-methoxy-5-nitroaniline with methanesulfonyl chloride gave the mesylamine. Catalytic reduction of the nitro group then gave the required aniline to condense with 4-methoxy-3-nitrobenzoyl chloride to give the anilide. Reduction by catalytic hydrogenation followed by immediate mesylation gave the mesylamine. Demethylation under usual conditions gave a stable borate complex of the required product.

Example 15

Compounds Provided Herein are Potent Disrupters of Alzheimer's Aβ 1-42 Fibrils

The compounds prepared in the preceding Examples were found to be potent disrupters/inhibitors of Alzheimer's disease Aβ fibrils. In a set of studies, the efficacy of certain compounds provided herein to cause a disassembly/disruption of pre-formed amyloid fibrils of Alzheimer's disease (i.e. consisting of Aβ 1-42 fibrils) was analyzed.

Part A—Thioflavin T Fluorometry Data

In one study, Thioflavin T fluorometry was used to determine the effects of the compounds, and of EDTA (as a negative control). In this assay Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al., Lab. Invest. 65:104-110, 1991; Levine III, Protein Sci. 2:404-410, 1993; Amyloid:Int. J. Exp. Clin. Invest. 2:1-6, 1995).

In this study, 25 μM of pre-fibrillized Aβ 1-42 (Bachem Inc) was incubated at 37° C. for 3 days, either alone, or in the presence of one of the compounds or EDTA (at Aβ:test compound weight ratios of 1:1, 1:0.1, 1:0.01 or 1:0.001). Following 3 days of co-incubation, 50 μl of each incubation mixture was transferred into a 96-well microtiter plate containing 150 μl of distilled water and 50 μl of a Thioflavin T solution (i.e. 500 mM Thioflavin T in 250 mM phosphate buffer, pH 6.8). The fluorescence was read at 485 nm (444 nm excitation wavelength) using an ELISA plate fluorometer after subtraction with buffer alone or compound alone, as blank).

The results of the 3-day incubations are presented below. For example, whereas EDTA caused no significant inhibition/disruption of Aβ 1-42 fibrils at all concentrations tested, the compounds (DC-0051, DC-0051-S1, S3, S4, S5, S6, S7, S8 and S9) all caused a dose-dependent disruption/disassembly of preformed Aβ 1-42 fibrils to some extent (Table 1). For example, compound DC-0051-S8 caused a significant (p<0.01) 87.9+/−0.78% inhibition when used at an Aβ:test compound wt/wt ratio of 1:0.1, and a significant 56.0+/−11.32% inhibition when used at an Aβ:test compound wt/wt ratio of 1:0.01 (Table 1). Under the same conditions (i.e. Aβ:test compound wt/wt ratio of 1:0.01), compound DC-0051 caused an 89.5+/−3.26% disruption, compound DC-0051-S5 caused an 80.0+/−0.63% disruption, and compound DC-0051-S9 caused an 84.1+/−4.28% disruption. This study indicated that the compound provided herein are disrupters/inhibitors of Alzheimer's disease type Aβ fibrils, and usually exert their effects in a dose-dependent manner.

Part B: SDS-PAGE/Western Blot Data

The disruption of Aβ 1-42, even in its monomeric form, was confirmed by a study involving the use of SDS-PAGE and Western blotting methods (not shown). In this latter study, triplicate samples of pre-fibrillized Aβ 1-42 (25 μM) was incubated at 37° C. for 3 days, alone or in the presence of the compounds or EDTA. Five micrograms of each sample was then filtered through a 0.2 μm filter. Protein recovered from the filtrate was then loaded, and ran on a 10-20% Tris-Tricine SDS-PAGE, blotted to nitrocellulose and detected using an Aβ-antibody (clone 6E10; Senetek). In this study, Aβ 1-42 was detected as a ~4 kilodalton band (i.e. monomeric Aβ) following incubation alone, or in the presence of EDTA, at 3 days. For example, Aβ 1-42 monmers were not detected following incubation of Aβ 1-42 with compounds DC-0051, DC-0051-S1, DC-0051-S5, DC-0051-S8 and DC-0051-S9, correlating nicely with the Thioflavin T fluorometry data (described above) and suggesting that these compounds were capable of causing a disappearance of monomeric Aβ 1-42. This study confirms that these compounds are also capable of causing a disruption/removal of monomeric Aβ 1-42.

Part C: Congo Red Binding Data

In the Congo red binding assay the ability of a test compound to alter amyloid (in this case, Aβ) binding to Congo redc is quantified. In this assay, Aβ 1-42 and test compounds were incubated for 3 days and then vacuum filtered through a 0.2 μm filter. The amount of Aβ 1-42 retained in the filter was then quantified following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic Aβ. This particular assay appears to be more stringent in character than Thioflavin T fluorometry, and it is more difficult to remove Congo red binding to Aβ 42 fibrils than assessed by other assays, so the % inhibitions observed even with potent compounds is usually lower than that observed as determined by other assays such as Thioflavin T fluometry.

In one study, the ability of Aβ fibrils to bind Congo red in the absence or presence of increasing amounts of the compounds or EDTA (at Aβ:test compound weight ratios of 1:0.001, 1:0.01, 1:0.1 and 1:1) was determined. The results of the 3-day incubations are presented in Table 2 below. Wheras EDTA caused no significant inhibition of Aβ 1-42 fibril binding to Congo red, the compounds (DC-0051, DC-0051-S1, S3, S4, S5, S6, S7, S8 and S9) caused a dose-dependent inhibition of Aβ binding to Congo red (Table 2). For example,

TABLE 1

Thioflavin T Fluorometry Data-Disruption of Aβ 1-42 Fibrils by Test Compounds (% inhibition of Aβ; for Aβ:test compound at given wt/wt ratio)

| Test Compound # | 1:1 (wt/wt) | 1:0.1 (wt/wt) | 1:0.01 (wt/wt) | 1:0.001 (wt/wt) |
| --- | --- | --- | --- | --- |
| EDTA (control) | 0.0 ± 3.59% | 0.0 ± 4.41% | 0.2 ± 3.03% | 0.0 ± 1.54% |
| DC-0051 | 98.7 ± 0.07% | 89.5 ± 3.26% | 32.0 ± 4.31% | 10.9 ± 2.24% |
| DC0051-S1 | 96.4 ± 0.58% | 74.6 ± 3.71% | 20.8 ± 4.63% | 9.0 ± 3.53% |
| DC0051-S3 | 92.5 ± 0.47% | 59.9 ± 1.34% | 16.1 ± 2.04% | 14.6 ± 2.90% |
| DC0051-S4 | 95.2 ± 0.42% | 70.2 ± 7.01% | 18.2 ± 3.68% | 16.6 ± 4.14% |
| DC0051-S5 | 99.0 ± 0.25% | 80.0 ± 0.63% | 28.4 ± 0.74% | 20.3 ± 6.71% |
| DC0051-S6 | 95.4 ± 0.72% | 53.5 ± 14.88% | 4.0 ± 4.33% | 9.5 ± 1.64% |
| DC0051-S7 | 92.8 ± 1.92% | 50.2 ± 6.94% | 10.1 ± 5.82% | 13.4 ± 3.42% |
| DC0051-S8 | 96.7 ± 0.73% | 87.9 ± 0.78% | 56.0 ± 11.32% | 32.9 ± 2.70% |
| DC0051-S9 | 98.8 ± 0.26% | 84.1 ± 4.28% | 60.7 ± 12.57% | 13.6 ± 2.08% | compound DC-0051-S5 caused a significant 82.3+/−0.59% inhibition of Congo red binding to Aβ 1-42 fibrils when used at an Aβ:test compound wt/wt ratio of 1:1, and a 40.3+/−5.81% inhibition when used an an Aβ:test compound wt/wt ratio of 1:0.1 (Table 2). Other good inhibitors as compared to the Aβ:test compound wt/wt ratio (of 1:0.1 appeared to be DC-0051-S1 (19.7+/−2.97% inhibition), DC-0051 (40.3+/−5.81% inhibition), DC-0051-S6 (17.1+/−4.94% inhibition), DC-0051-S8 (19.8+/−2.43% inhibition) and DC-0051-S9 (17.4+/−6.11% inhibition).

TABLE 2

Congo red Binding Data-Disruption of Aβ 1-42 Fibrils by Test Compounds (% inhibition of Aβ; for Aβ:test compound at given wt/wt ratio)

| Test Compound # | 1:1 (wt/wt) | 1:0.1 (wt/wt) | 1:0.01 (wt/wt) | 1:0.001 (wt/wt) |
| --- | --- | --- | --- | --- |
| EDTA (control) | 3.9 +/− 1.37% | 0.0 ± 0.76% | 0.0 +/− 0.49% | 0.0 ± 0.62% |
| DC-0051 | 76.7 +/− 1.22% | 40.3 +/− 5.81% | 3.3 +/− 0.95% | 1.7 +/− 0.10% |
| DC0051-S1 | 48.6 +/− 2.01% | 19.7 +/− 2.97% | 2.4 +/− 0.92% | 1.0 +/− 2.11% |
| DC0051-S3 | 36.2 +/− 2.51% | 16.6 +/− 1.87% | 0.0 +/− 2.11% | 0.0 +/− 2.12% |
| DC0051-S4 | 48.8 +/− 2.29% | 15.1 +/− 4.17% | 0.0 +/− 2.13% | 1.5 +/− 1.42% |
| DC0051-S5 | 82.3 +/− 0.59% | 17.5 +/− 1.23% | 0.2 +/− 1.97% | 0.0 +/− 1.37% |
| DC0051-S6 | 48.5 +/− 3.58% | 17.1 +/− 4.94% | 2.1 +/− 1.14% | 3.1 +/− 0.97% |
| DC0051-S7 | 44.6 +/− 4.59% | 8.8 +/− 1.70% | 0.0 +/− 0.29% | 2.4 +/− 2.23% |
| DC0051-S8 | 41.2 +/− 6.83% | 19.8 +/− 2.43% | 3.9 +/− 0.54% | 2.3 +/− 3.16% |
| DC0051-S9 | 60.8 +/− 2.12% | 17.4 +/− 6.11% | 3.8 +/− 3.90% | 0.0 +/− 1.27% |

Example 16

Additional Compounds Provided Herein are Potent Disrupters of Alzheimer's Aβ 1-42 Fibrils The compounds prepared in the preceding Examples were found to be potent disrupters/inhibitors of Alzheimer's disease Aβ fibrils. In another set of studies, the efficacy of certain compounds provided herein (and referred to as DC-0051-B2, DC-0051-B3 and DC-0051-B4) to cause a disassembly/disruption of pre-formed amyloid fibrils of Alzheimer's disease (i.e. consisting of Aβ 1-42 fibrils) was analyzed.

Thioflavin T Fluorometry Data

In one study, Thioflavin T fluorometry was used to determine the effects of the compounds, and of EDTA (as a negative control). In this assay Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al., Lab. Invest. 65:104-110, 1991; Levine III, Protein Sci. 2:404-410, 1993; Amyloid:Int. J. Exp. Clin. Invest. 2:1-6, 1995).

In this study, 25 µM of pre-fibrillized Aβ 1-42 (Bachem Inc) was incubated at 37° C. for 3 days, either alone, or in the presence of one of the compounds (DC-0051-B2, DC-0051-B3 or DC-0051-B4). Following 3 days of co-incubation, 50 µl of each incubation mixture was transferred into a 96-well microtiter plate containing 150 µl of distilled water and 50 µl of a Thioflavin T solution (i.e. 500 mM Thioflavin T in 250 mM phosphate buffer, pH 6.8). The fluorescence was read at 485 nm (444 nm excitation wavelength) using an ELISA plate fluorometer after subtraction with buffer alone or compound alone, as blank).

The results of the 3-day incubations are presented below. For example, whereas EDTA caused no significant inhibition/disruption of Aβ 1-42 fibrils at all concentrations tested, the compounds (DC-0051-B2, DC-0051-B3, and DC-0051-B4) all caused a dose-dependent disruption/disassembly of pre-formed Aβ 1-42 fibrils to some extent (Table 3). The most efficacious compounds to disrupt pre-formed Aβ 1-42 fibrils as assessed by the Thioflavin T fluometry assay appeared to be DC-0051-B2. For example, compound DC-0051-B2 caused a significant (p<0.01) 65.8+/−2.01% inhibition when used at an Aβ:test compound wt/wt ratio of 1:0.1, and a significant 85.5+/−1.27% inhibition when used at an Aβ:test compound wt/wt ratio of 1:1 (Table 3). This study indicated that the additional compounds provided herein are disrupters/inhibitors of Alzheimer's disease type Aβ fibrils, and usually exert their effects in a dose-dependent manner.

TABLE 3

Thioflavin T Fluorometry Data-Disruption of Aβ 1-42 Fibrils by Test Compounds (% inhibition of Aβ; for Aβ:test compound at given wt/wt ratio)

| Test Compound # | 1:1 (wt/wt) | 1:0.1 (wt/wt) | 1:0.01 (wt/wt) | 1:0.001 (wt/wt) |
| --- | --- | --- | --- | --- |
| EDTA (control) | 5.0 +/− 11.39% | 0.0 +/− 1.18% | 0.0 +/− 2.26% | 10.3 +/− 10.81% |
| DC-0051 | 98.5 +/− 0.56% | 88.8 +/− 0.76% | 41.1 +/− 2.52% | 18.6 +/− 8.89% |
| DC0051-B2 | 85.5 +/− 1.27% | 65.8 +/− 2.01% | 19.2 +/− 6.18% | 10.2 +/− 9.49% |
| DC0051-B3 | 17.9 +/− 16.85% | 22.2 +/− 2.63% | 1.0 +/− 1.62% | 15.7 +/− 7.34% |
| DC0051-B4 | 28.1 +/− 3.06% | 21.1 +/− 4.00% | 3.6 +/− 4.96% | 17.2 +/− 4.32% |

Example 17

Compounds Provided Herein are Potent Disrupters of Type 2 Diabetes IAPP Fibrils

The compounds prepared in the preceding Examples were also found to be potent disrupters/inhibitors of type 2 diabetes IAPP fibrils. In a set of studies, the efficacy of certain compounds provided herein to cause a disassembly/disruption of pre-formed amyloid fibrils of type 2 diabetes (i.e. consisting of IAPP fibrils) was analyzed.

Part A—Thioflavin T Fluorometry Data

In one study, Thioflavin T fluorometry was used to determine the effects of the compounds, and of EDTA (as a negative control). In this assay Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al., Lab. Invest. 65:104-110, 1991; Levine III, Protein Sci. 2:404-410, 1993; Amyloid:Int. J. Exp. Clin. Invest. 2:1-6, 1995).

In this study, 25 µM of IAPP (Bachem Inc) was incubated at 37° C. for 3 days, either alone, or in the presence of one of the compounds or EDTA (at Aβ:test compound weight ratios of 1:1, 1:0.1, 1:0.01 or 1:0.001). Following 3 days of co-incubation, 50 µl of each incubation mixture was transferred into a 96-well microtiter plate containing 150 µl of distilled water and 50 µl of a Thioflavin T solution (i.e. 500 mM Thioflavin T in 250 mM phosphate buffer, pH 6.8). The fluorescence was read at 485 nm (444 nm excitation wavelength) using an ELISA plate fluorometer after subtraction with buffer alone or compound alone, as blank).

The results of the 3-day incubations are presented below. For example, whereas EDTA caused no significant inhibition/disruption of IAPP fibrils at all concentrations tested, the compounds (DC-0051, DC-0051-S1, S3, S4, S5, S6, S7, S8 and S9) all caused a dose-dependent disruption/disassembly of preformed Aβ 1-42 fibrils to some extent (Table 4). For example, compound DC-0051-S8 caused a significant ($p<0.01$) 91.4+/−1.06% inhibition when used at an Aβ:test compound wt/wt ratio of 1:0.1, and a significant 52.2+/−0.45% inhibition when used at an Aβ:test compound wt/wt ratio of 1:0.01 (Table 4). Under the same conditions (i.e. Aβ:test compound wt/wt ratio of 1:0.01), compound DC-0051 caused a 63.9+/−0.56% disruption, compound DC-0051-S1 caused a 47.2+/−5.48% disruption, and compound DC-0051-S3 caused a 49.3+/−0.65% disruption. This study indicated that the compound provided herein are also potent disrupters/inhibitors of type 2 diabetes IAPP fibrils, and usually exert their effects in a dose-dependent manner.

Part B: Congo Red Binding Data

In the Congo red binding assay the ability of a test compound to alter amyloid (in this case, IAPP) binding to Congo redc is quantified. In this assay, IAPP and test compounds were incubated for 3 days and then vacuum filtered through a 0.2 µm filter. The amount of IAPP retained in the filter was then quantified following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic IAPP. This particular assay appears to be more stringent in character than Thioflavin T fluorometry, and it is more difficult to remove Congo red binding to IAPP fibrils than assessed by other assays, so the % inhibitions observed even with potent compounds is usually lower than that observed as determined by other assays such as Thioflavin T fluometry.

In one study, the ability of IAPP fibrils to bind Congo red in the absence or presence of increasing amounts of the compounds or EDTA (at IAPP:test compound weight ratios of 1:0.001, 1:0.01, 1:0.1 and 1:1) was determined. The results of the 3-day incubations are presented in Table 5 below. Wheras EDTA caused no significant inhibition of IAPP fibril binding to Congo red, the compounds (DC-0051, DC-0051-S1, S3, S4, S5, S6, S7, S8 and S9) caused a dose-dependent inhibition of APP binding to Congo red (Table 5). For example, compound DC-0051-S8 caused a significant 41.0+/−4.15% inhibition of Congo red binding to IAPP fibrils when used at an IAPP:test compound wt/wt ratio of 1:1, and a 26.7+/−0.82% inhibition when used an an IAPP:test compound wt/wt ratio of 1:0.1 (Table 5). Other good inhibitors as compared to the IAPP:test compound wt/wt ratio of 1:0.1 appeared to be DC-0051 (51.+/−0.63% inhibition), DC-0051-S1 (24.1+/−1.99% inhibition), DC-0051-S4 (22.0+/−0.26% inhibition), and DC-0051-S9 (21.2+/−2.70% inhibition)

TABLE 4

Thioflavin T Fluorometry Data-Disruption of IAPP Fibrils by Test Compounds
(% inhibition of Aβ; for Aβ:test compound at given wt/wt ratio)

| Test Compound # | 1:1 (wt/wt) | 1:0.1 (wt/wt) | 1:0.01 (wt/wt) | 1:0.001 (wt/wt) |
|---|---|---|---|---|
| EDTA (control) | 0.0 ± 1.31% | 1.6 +/− 5.86% | 4. +/− 3.152% | 0.0 +/− 0.56% |
| DC-0051 | 99.6 +/− 0.12% | 95.6 +/− 0.31% | 63.9 +/− 0.56% | 32.5 +/− 1.51% |
| DC0051-S1 | 98.5 +/− 0.12% | 86.2 +/− 1.95% | 47.2 +/− 5.48% | 6.7 +/− 0.64% |
| DC0051-S3 | 98.7 +/− 0.24% | 87.2 +/− 1.48% | 49.3 +/− 0.65% | 19.0 +/− 2.70% |
| DC0051-S4 | 97.5 +/− 0.11% | 80.2 +/− 1.59% | 36.7 +/− 0.74% | 14.3 +/− 1.57% |
| DC0051-S5 | 99.3 +/− 0.21% | 87.1 +/− 1.46% | 36.1 +/− 1.29% | 15.0 +/− 2.38% |
| DC0051-S6 | 98.7 +/− 0.52% | 74.4 +/− 12.17% | 19.7 +/− 1.64% | 0.0 +/− 1.68% |
| DC0051-S7 | 98.6 +/− 0.18% | 77.7 +/− 2.68% | 30.3 +/− 6.06% | 7.7 +/− 2.60% |
| DC0051-S8 | 99.5 +/− 0.32% | 91.4 +/− 1.06% | 52.2 +/− 0.45% | 8.8 +/− 0.55% |
| DC0051-S9 | 99.5 +/− 0.15% | 82.8 +/− 4.28% | 34.8 +/− 1.07% | 7.0 +/− 2.49% |

TABLE 5

Congo red Binding Data-Disruption of IAPP Fibrils by Test Compounds
(% inhibition of IAPP; for IAPP:test compound at given wt/wt ratio)

| Test Compound # | 1:1 (wt/wt) | 1:0.1 (wt/wt) | 1:0.01 (wt/wt) | 1:0.001 (wt/wt) |
|---|---|---|---|---|
| EDTA (control) | 13.9 +/− 4.71% | 0.0 +/− 2.40% | 0.0 +/− 1.65% | 0.0 ± 1.82% |
| DC-0051 | 73.6 +/− 2.15% | 51.0 +/− 0.63% | 8.7 +/− 2.60% | 0.0 +/− 4.07% |
| DC0051-S1 | 44.1 +/− 1.03% | 24.1 +/− 1.99% | 0.0 +/− 2.55% | 0.0 +/− 3.60% |
| DC0051-S3 | 52.5 +/− 1.84% | 17.4 +/− 2.21% | 3.4 +/− 3.63% | 0.0 +/− 1.94% |
| DC0051-S4 | 30.0 +/− 1.38% | 22.0 +/− 0.26% | 2.4 +/− 3.24% | 0.0 +/− 2.89% |
| DC0051-S5 | 59.3 +/− 0.93% | 11.0 +/− 3.94% | 0.0 +/− 1.50% | 0.0 +/− 2.26% |
| DC0051-S6 | 46.0 +/− 0.65% | 7.7 +/− 5.15% | 0.0 +/− 4.57% | 0.0 +/− 1.41% |
| DC0051-S7 | 42.7 +/− 2.82% | 3.6 +/− 1.15% | 3.0 +/− 3.54% | 1.8 +/− 3.25% |
| DC0051-S8 | 41.0 +/− 4.15% | 26.7 +/− 0.82% | 0.0 +/− 5.19% | 0.3 +/− 2.37% |
| DC0051-S9 | 52.3 +/− 1.00% | 21.2 +/− 2.70% | 1.1 +/− 5.40% | 2.5 +/− 5.02% |

Example 18

Compounds Provided Herein are Potent Disrupters of Alpha-Synuclein Fibrils

The compounds prepared in the preceding Examples were also found to be potent disrupters/inhibitors of alpha-synuclein fibrils. In a set of studies, the efficacy of certain compounds provided herein to cause a disassembly/disruption of pre-formed amyloid-like fibrils of Parkinson's disease (i.e. consisting of alpha-synuclein fibrils) was analyzed.

Thioflavin T Fluorometry Data

In one study, Thioflavin T fluorometry was used to determine the effects of the compounds, and of EDTA (as a negative control). In this assay Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al., Lab. Invest. 65:104-110, 1991; Levine III, Protein Sci. 2:404-410, 1993; Amyloid:Int. J. Exp. Clin. Invest. 2:1-6, 1995).

In this study, 25 μM of alpha-synuclein (Recombinant Peptide) was first incubated at 55° C. for 2 days with heparin (Sigma) to cause alpha-synuclein aggregation and fibril formation. Heparin, is a highly sulfated glycosaminoglycan known to cause aggregation of amyloid proteins. Following initial alpha-synuclein fibrillization, alpha-synuclein+heparin was incubated at 37° C. for 3 days, either alone, or in the presence of one of the compounds or EDTA (at Aβ:test compound weight ratios of 1:1, 1:0.1, 1:0.01 or 1:0.001). Following 3 days of co-incubation, 50 μl of each incubation mixture was transferred into a 96-well microtiter plate containing 150 μl of distilled water and 50 μl of a Thioflavin T solution (i.e. 500 mM Thioflavin T in 250 mM phosphate buffer, pH 6.8). The fluorescence was read at 485 nm (444 nm excitation wavelength) using an ELISA plate fluorometer after subtraction with buffer alone or compound alone, as blank).

The results of the 3-day incubations are presented below. The compounds (DC-0051, DC-0051-S1, S3, S4, S5, S6, S7, S8 and S9) all caused a dose-dependent disruption/disassembly of preformed akpha-synuclein fibrils to some extent (Table 6). For example, compound DC-0051-S1 caused a significant ($p<0.01$) 94.5+/−2.11% inhibition when used at an Aβ:test compound wt/wt ratio of 1:0.1, and a significant 99.1+/−0.12% inhibition when used at an Aβ:test compound wt/wt ratio of 1:1 (Table 6). On the other hand, compounds DC-0051-S8 caused a significant ($p<0.01$) 84.6+/−0.47% inhibition when used at an Aβ:test compound wt/wt ratio of 1:0.1, and a significant 96.1+/−1.14% inhibition when used at an Aβ:test compound wt/wt ratio of 1:1 (Table 6). This study indicated that the compounds provided herein are also potent disrupters/inhibitors of Parkinson's disease alpha-synuclein fibrils, and usually exert their effects in a dose-dependent manner.

TABLE 6

Thioflavin T Fluorometry Data-Disruption of Apha-Synuclein Fibrils by Test Compounds
(% inhibition of Aβ; for Aβ:test compound at given wt/wt ratio)

| Test Compound # | 1:1 (wt/wt) | 1:0.1 (wt/wt) | 1:0.01 (wt/wt) | 1:0.001 (wt/wt) |
|---|---|---|---|---|
| DC-0051 | 99.7 +/− 0.09% | 98.6 +/− 0.26% | 82.7 +/− 2.40% | 64.5 +/− 1.64% |
| DC0051-S1 | 99.1 +/− 0.12% | 94.5 +/− 2.11% | 55.9 +/− 13.31% | 52.9 +/− 1.34% |
| DC0051-S3 | 97.0 +/− 0.85% | 87.6 +/− 4.07% | 43.6 +/− 11.73% | 37.6 +/− 5.18% |
| DC0051-S4 | 96.0- +/− 0.50% | 86.8 +/− 1.55% | 53.7 +/− 10.98% | 41.1 +/− 6.53% |
| DC0051-S5 | 98.5 +/− 0.09% | 91.6 +/− 0.37% | 65.0 +/− 4.42% | 49.1 +/− 2.61% |
| DC0051-S6 | 96.0 +/− 1.65% | 66.6 +/− 5.77% | 46.9 +/− 5.52% | 53.3 +/− 1.70% |
| DC0051-S7 | 96.0 +/− 0.78% | 82.1 +/− 8.94% | 33.4 +/− 4.77% | 47.9 +/− 6.32% |
| DC0051-S8 | 96.1 +/− 1.14% | 84.6 +/− 0.47% | 44.1 +/− 2.19% | 38.7 +/− 4.76% |
| DC0051-S9 | 99.6 +/− 0.19% | 96.1 +/− 0.65% | 64.5 +/− 5.56% | 50.9 +/− 1.86% |

Example 19

Compositions of Compounds Provided Herein

The compounds provided herein, as mentioned previously, are desirably administered in the form of pharmaceutical compositions. Suitable pharmaceutical compositions, and the method of preparing them, are well-known to persons of ordinary skill in the art and are described in such treatises as *Remington: The Science and Practice of Pharmacy*, A. Gennaro, ed., 20th edition, Lippincott, Williams & Wilkins, Philadelphia, Pa.

Representative compositions are as follows:

Oral Tablet Formulation

An oral tablet formulation of a compound provided herein is prepared as follows:

|  | % w/w |
| --- | --- |
| Compound provided herein | 10.0 |
| Magnesium stearate | 0.5 |
| Starch | 2.0 |
| Hydroxypropylmethylcellulose | 1.0 |
| Microcrystalline cellulose | 86.5 |

The ingredients are mixed to homogeneity, then granulated with the aid of water, and the granulates dried. The granulate is then compressed into tablets sized to give a suitable dose of the compound. The tablet is optionally coated by applying a suspension of a film forming agent (e.g. hydroxypropylmethylcellulose), pigment (e.g. titanium dioxide), and plasticizer (e.g. diethyl phthalate), and drying the film by evaporation of the solvent. The film coat may comprise, for example, 2-6% of the tablet weight.

Oral Capsule Formulation

The granulate from the previous section of this Example is filled into hard gelatin capsules of a size suitable to the intended dose. The capsule is banded for sealing, if desired.

Softgel Formulation

A softgel formulation is prepared as follows:

|  | % w/w |
| --- | --- |
| Compound provided herein | 20.0 |
| Polyethylene glycol 400 | 80.0 |

The compound is dissolved or dispersed in the polyethylene glycol, and a thickening agent added if required. A quantity of the formulation sufficient to provide the desired dose of the compound is then filled into softgels.

Parenteral Formulation

A parenteral formulation is prepared as follows:

|  | % w/w |
| --- | --- |
| Compound provided herein | 1.0 |
| Normal saline | 99.0 |

The compound is dissolved in the saline, and the resulting solution is sterilized and filled into vials, ampoules, and pre-filled syringes, as appropriate.

Controlled-Release Oral Formulation

A sustained release formulation may be prepared by the method of U.S. Pat. No. 4,710,384, as follows:

One Kg of a compound provided herein is coated in a modified Uni-Glatt powder coater with Dow Type 10 ethyl cellulose. The spraying solution is an 8% solution of the ethyl cellulose in 90% acetone to 10% ethanol. Castor oil is added as plasticizer in an amount equal to 20% of the ethyl cellulose present. The spraying conditions are as follows: 1) speed, 1 liter/hour; 2) flap, 10-15%; 3) inlet temperature, 50° C., 4) outlet temperature, 30° C., 5) percent of coating, 17%. The coated compound is sieved to particle sizes between 74 and 210 microns. Attention is paid to ensure a good mix of particles of different sizes within that range. Four hundred mg of the coated particles are mixed with 100 mg of starch and the mixture is compressed in a hand press to 1.5 tons to produce a 500 mg controlled release tablet.

The claimed subject matter is not limited in scope by the specific embodiments described herein. Indeed, various modifications of the specific embodiments in addition to those described will become apparent to those skilled in the art from the foregoing descriptions. Such modifications are intended to fall within the scope of the appended claims. Various publications are cited herein, the disclosures of which are incorporated by reference in their entireties.

What is claimed is:

1. A compound selected from:

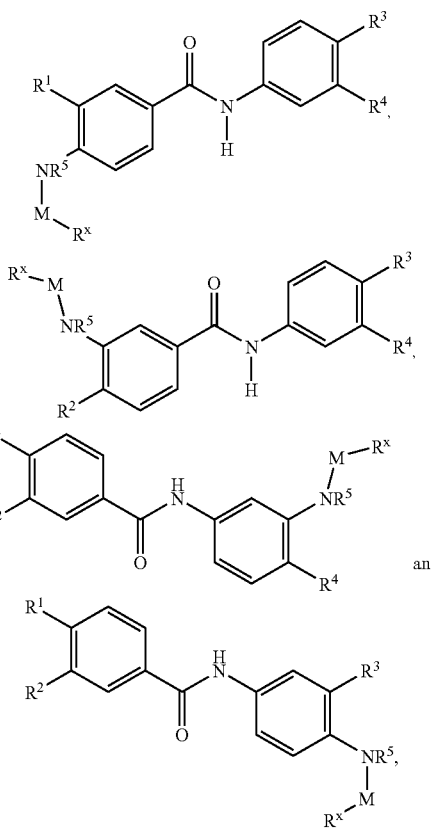

and

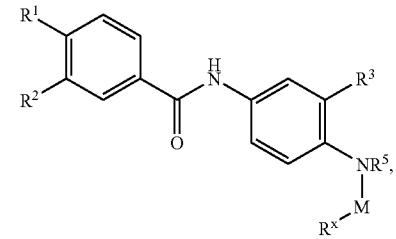

or a pharmaceutically-acceptable salt thereof, wherein M is $S(O)_2$, $R^x$ is alkyl, and $R^1$, $R^2$, $R^3$ and $R^4$ are each independently selected from OH, —$NR^5C(=O)R^6$ and —$NR^7S(O_2)R^8$, wherein $R^5$ and $R^7$ are each independently hydrogen or alkyl, and $R^6$ and $R^8$ are alkyl.

2. The compound of claim 1, wherein, $R^5$ is isopropyl.

3. The compound of claim 1, wherein $R^x$ is methyl.

4. The compound of claim 1 selected from
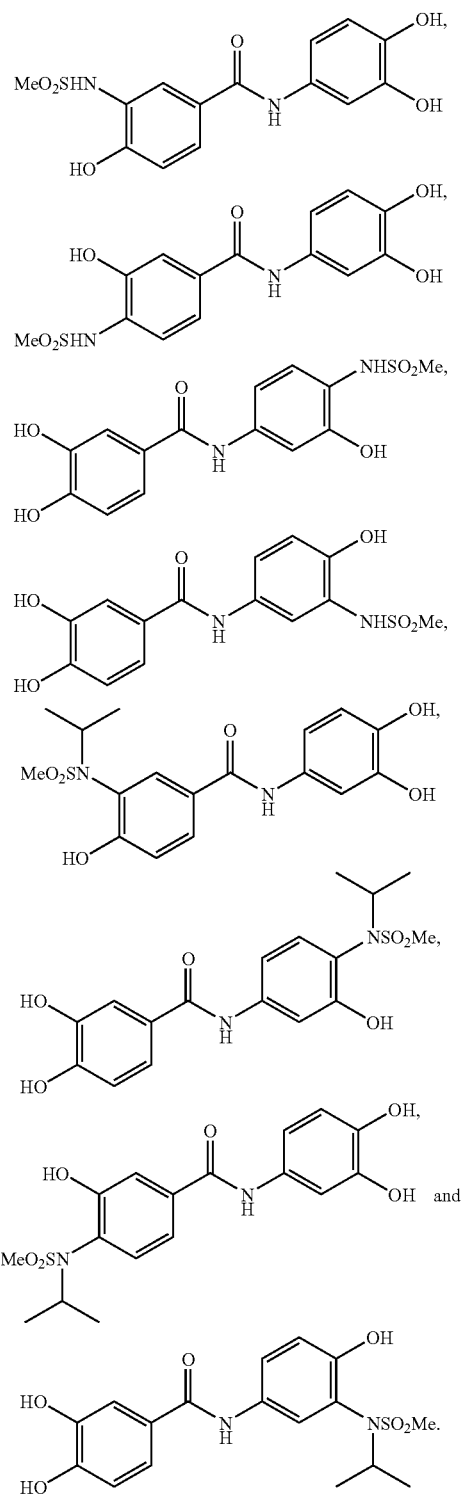
5. A pharmaceutical composition comprising the compound of claim 1, and a pharmaceutically acceptable excipient.
6. The compound of claim 1 selected from:
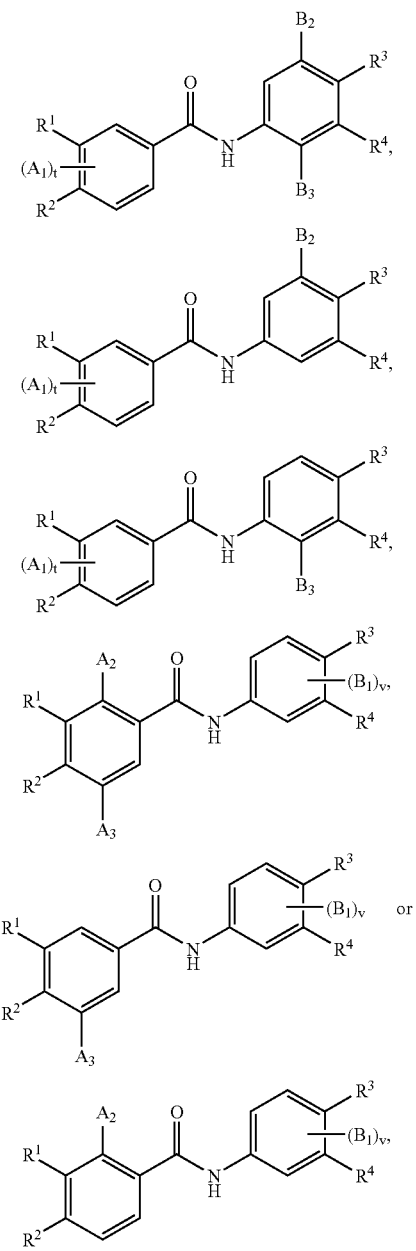
7. The compound of claim 1, wherein $R^1$, $R^2$, $R^3$ and $R^4$ are OH.
8. The compound of claim 1, wherein $R^5$ is hydrogen.
* * * * *

UNITED STATES PATENT AND TRADEMARK OFFICE
CERTIFICATE OF CORRECTION

PATENT NO.        : 7,745,490 B2
APPLICATION NO.   : 11/328748
DATED             : June 29, 2010
INVENTOR(S)       : Snow et al.

Page 1 of 1

It is certified that error appears in the above-identified patent and that said Letters Patent is hereby corrected as shown below:

Please insert the following claim in place of claim 6.

Column 86:
--6. The compound of claim 1 selected from:

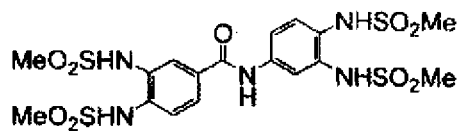 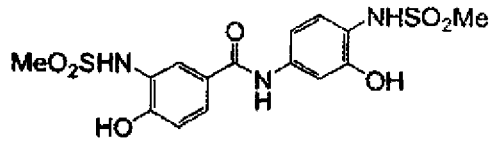

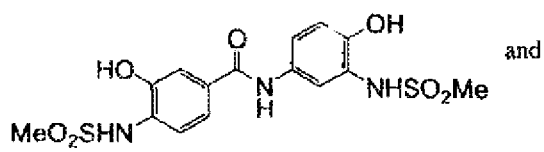 and 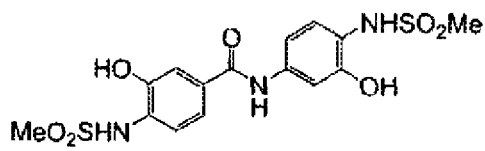

--.

Signed and Sealed this
Eighth Day of May, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,745,490 B2 | Page 1 of 1 |
| APPLICATION NO. | : 11/328748 | |
| DATED | : June 29, 2010 | |
| INVENTOR(S) | : Snow et al. | |

It is certified that error appears in the above-identified patent and that said Letters Patent is hereby corrected as shown below:

Column 88, lines 4-54, please insert the following claim in place of claim 6.

--6. The compound of claim 1 selected from:

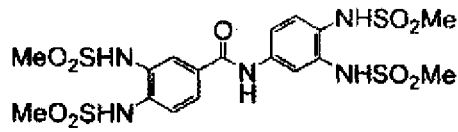   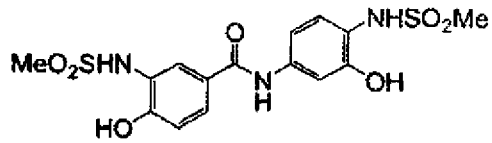

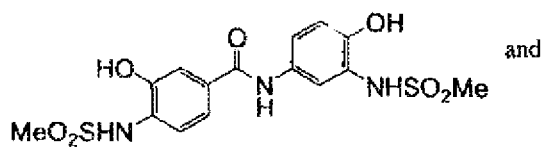 and 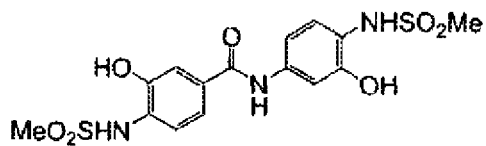

--.

This certificate supersedes the Certificate of Correction issued May 8, 2012.

Signed and Sealed this
Twelfth Day of June, 2012

David J. Kappos
*Director of the United States Patent and Trademark Office*